United States Patent
Antony et al.

(10) Patent No.: US 10,093,706 B2
(45) Date of Patent: Oct. 9, 2018

(54) DOMINANT POSITIVE HNRNP-E1 POLYPEPTIDE COMPOSITIONS AND METHODS

(71) Applicant: Indiana University Research and Technology Corporation, Indianapolis, IN (US)

(72) Inventors: Asok C. Antony, Indianapolis, IN (US); Ying-Sheng Tang, Zionsville, IN (US)

(73) Assignee: Indiana University Research and Technology Corporation, Indianapolis, IN (US)

(*) Notice: Subject to any disclaimer, the term of this patent is extended or adjusted under 35 U.S.C. 154(b) by 0 days.

(21) Appl. No.: 15/419,655

(22) Filed: Jan. 30, 2017

(65) Prior Publication Data

US 2018/0215800 A1    Aug. 2, 2018

(51) Int. Cl.

| | |
|---|---|
| A61K 38/16 | (2006.01) |
| C07K 14/47 | (2006.01) |
| C12N 15/11 | (2006.01) |
| C12N 7/00 | (2006.01) |
| A61K 48/00 | (2006.01) |
| C12P 21/02 | (2006.01) |
| A61K 38/00 | (2006.01) |

(52) U.S. Cl.
CPC .............. *C07K 14/47* (2013.01); *C12N 7/00* (2013.01); *C12N 15/11* (2013.01); *A61K 38/00* (2013.01); *C07K 2319/85* (2013.01)

(58) Field of Classification Search
None
See application file for complete search history.

(56) References Cited

U.S. PATENT DOCUMENTS

| | | | |
|---|---|---|---|
| 5,652,122 A | 7/1997 | Frankel et al. | |
| 5,674,980 A | 10/1997 | Frankel et al. | |
| 6,333,195 B1 | 12/2001 | Respess et al. | |
| 6,881,825 B1 | 4/2005 | Robbins et al. | |
| 2006/0088599 A1 | 4/2006 | Prasad et al. | |

FOREIGN PATENT DOCUMENTS

| | | |
|---|---|---|
| WO | WO200200871 | 1/2002 |
| WO | WO2002086129 | 10/2002 |
| WO | WO2002086134 | 10/2002 |
| WO | WO2012045075 | 10/2011 |
| WO | WO2012019168 | 2/2012 |
| WO | WO2012135805 | 10/2012 |
| WO | WO2012158736 | 11/2012 |
| WO | WO2013039857 | 3/2013 |
| WO | WO2013039861 | 3/2013 |
| WO | WO2013052523 | 4/2013 |

OTHER PUBLICATIONS

Olsen, et al. Trypsin cleaves exclusively C-terminal to arginine and lysine residues. Mol Cell Proteomics. Jun. 2004;3(6):608-14.

Ostareck, et al. mRNA silencing in erythroid differentiation: hnRNP K and hnRNP E1 regulate 15-lipoxygenase translation from the 3' end. Cell. May 16, 1997;89(4):597-606.

Ostareck-Lederer. et al. Translation of 15-lipoxygenase mRNA is inhibited by a protein that binds to a repeated sequence in the 3' untranslated region. Embo J. Mar. 15, 1994;13(6):1476-81.

Ostareck-Lederer, et al. Cytoplasmic regulatory functions of the KH-domain proteins hnRNPs K and E1/E2. Trends Biochem Sci. Nov. 1998;23(11):409-11.

Paulding, et al. Regulation of tyrosine hydroxylase mRNA stability by protein-binding, pyrimidine-rich sequence in the 3'-untranslated region. J Biol Chem. Jan. 22, 1999;274(4):2532-8.

Philpott CC. Coming into view: eukaryotic iron chaperones and intracellular iron delivery. J Biol Chem. Apr. 20, 2012;287(17):13518-23.

Pickering, et al. Polypyrimidine tract binding protein and poly r(C) binding protein 1 interact with the BAG-1 IRES and stimulate its activity in vitro and in vivo. Nucleic Acids Res. Jan. 15, 2003;31(2):639-46.

Pillai, et al. Expression of folate receptors and heterogeneous nuclear ribonucleoprotein E1 in women with human papillomavirus mediated transformation of cervical tissue to cancer. J Clin Pathol. Aug. 2003;56(8):569-74.

Rondon, et al., Hypoxia up-regulates the activity of a novel erythropoietin mRNA binding protein. J Biol Chem. Sep. 5, 1991;266(25):16594-8.

Rossolini, et al., Use of deoxyinosine-containing primers vs degenerate primers for polymerase chain reaction based on ambiguous sequence information. Mol Cell Probes. Apr. 1994;8(2):91-8.

Schlotz, et al., Lower maternal folate status in early pregnancy is associated with childhood hyperactivity and peer problems in offspring. J Child Psychol Psychiatry. May 2010;51(5):594-602.

Shi, et al., A cytosolic iron chaperone that delivers iron to ferritin. Science. May 30, 2008;320(5880):1207-10.

Sidiqi, et al., Structure and RNA binding of the third KH domain of poly(C)-binding protein 1. Nucleic Acids Res. 2005;33(4):1213-21.

Stabler, et al., Elevation of total homocysteine in the serum of patients with cobalamin or folate deficiency detected by capillary gas chromatography-mass spectrometry. J Clin Invest. Feb. 1998;81(2):466-74.

(Continued)

*Primary Examiner* — Nancy J Leith
(74) *Attorney, Agent, or Firm* — Quarles & Brady LLP

(57) ABSTRACT

Described herein are compositions relating to engineered hnRNP-E1 variant polypeptides, nucleic acids encoding such polypeptides, engineered hnRNP-E1 compositions, and methods of use thereof. In some embodiments, the engineered hnRNP-E1 polypeptide contains a C293S substitution and retains the ability to bind to a poly(rC)- and poly(U)-rich 5'-UTR element in its cognate mRNA targets in the absence of homocysteine. In some cases, the engineered hnRNP-E1 compositions provided herein are useful to increase the translation of a subset of mRNAs or to treat certain health conditions as described herein.

13 Claims, 15 Drawing Sheets
(5 of 15 Drawing Sheet(s) Filed in Color)
Specification includes a Sequence Listing.

(56) References Cited

OTHER PUBLICATIONS

Stabler SP. Clinical practice. Vitamin B12 deficiency. N Engl J Med. Jan. 10, 2013;368(2):149-60.
Steenweg-de Graaff, et al., Maternal folate status in early pregnancy and child emotional and behavioral problems: the Generation R Study. Am J Clin Nutr. Jun. 2012;95(6):1413-21.
Strand, et al. Cobalamin and folate status predicts mental development scores in North Indian children 12-18 mo of age. Am J Clin Nutr. Feb. 2013;97(2):310-7.
Sun, et al. Transduction of folate receptor cDNA into cervical carcinoma cells using recombinant adeno-associated virions delays cell proliferation in vitro and in vivo. J Clin Invest. Sep. 1995;96(3):1535-47.
Sun, et al. Evidence that a specific interaction between an 18-base cis-element in the 5'-untranslated region of human folate receptor-alpha mRNA and a 46-kDa cytosolic trans-factor is critical for translation. J Biol Chem. Oct. 11, 1996;271(41):25539-47.
Suren, et al. Association between maternal use of folic acid supplements and risk of autism spectrum disorders in children. JAMA. Feb. 13, 2013;309(6):570-7.
Tang, et al. Incrimination of heterogeneous nuclear ribonucleoprotein E1 (hnRNP-E1) as a candidate sensor of physiological folate deficiency. J Biol Chem. Nov. 11, 2011;286(45):39100-15.
Thyagarajan, et al. Phylogenetically conserved binding of specific K homology domain proteins to the 3'-untranslated region of the vertebrate middle neurofilament mRNA. J Biol Chem. Nov. 26, 2004;279(48):49680-8.
Thyagarajan, et al. Dynamic endogenous association of neurofilament mRNAs with K-homology domain ribonucleoproteins in developing cerebral cortex. Brain Res. Jan. 16, 2008;1189:33-42.
Thyagarajan, et al. Post-transcriptional control of neurofilaments in development and disease. Exp Cell Res. Jun. 10, 2007;313(10):2088-97.
Torheim, et al. Women in resource-poor settings are at risk of inadequate intakes of multiple micronutrients. J Nutr. Nov. 2010;140(11):2051S-8S.
Tran, et al. Fetal iron deficiency alters the proteome of adult rat hippocampal synaptosomes. Am J Physiol Regul Integr Comp Physiol. Dec. 2013;305(11):R1297-306.
Trompeter, et al. Rapid and highly efficient gene transfer into natural killer cells by nucleofection. J Immunol Methods. Mar. 1, 2003;274(1-2):245-56.
Ule, et al. Clip identifies Nova-regulated RNA networks in the brain. Science. Nov. 14, 2003;302(5648):1212-5.
Veena, et al. Higher maternal plasma folate but not vitamin B-12 concentrations during pregnancy are associated with better cognitive function scores in 9—to 10—year-old children in South India. J Nutr. May 2010;140(5):1014-22.
Waggoner, et al. Identification of mRNAs associated with alphaCP2-containing RNP complexes. Mol Cell Biol. Oct. 2003;23(19):7055-67.
Waggoner, et al. Depletion of the poly(C)-binding proteins alphaCP1 and alphaCP2 from K562 cells leads to p53-independent induction of cyclin-dependent kinase inhibitor (CDKN1A) and G1 arrest. J Biol Chem. Apr. 3, 2009;284(14):9039-49.
Wang, et al. Detection and characterization of a 3' untranslated region ribonucleoprotein complex associated with human alpha-globin mRNA stability. Mol Cell Biol. Mar. 1995;15(3):1769-77.
Wong, et al. Increasing neurofilament subunit NF-M expression reduces axonal NF-H, inhibits radial growth, and results in neurofilamentous accumulation in motor neurons. J Cell Biol. Sep. 1995;130(6):1413-22.
Xiao, et al. Influence of physiologic folate deficiency on human papillomavirus type 16 (HPV16)-harboring human keratinocytes in vitro and in vivo. J Biol Chem. Apr. 6, 2012;287(15):12559-77.
Xiao, et al. Isolation and characterization of a folate receptor mRNA-binding trans-factor from human placenta. Evidence favoring identity with heterogeneous nuclear ribonucleoprotein E1. J Biol Chem. Nov. 2, 2001;276(44):41510-7.
Xiao, et al. Maternal folate deficiency results in selective upregulation of folate receptors and heterogeneous nuclear ribonucleoprotein-E1 associated with multiple subtle aberrations in fetal tissues. Birth Defects Res A Clin Mol Teratol. Jan. 2005;73(1):6-28.
Xu, et al. Subunit composition of neurofilaments specifies axonal diameter. J Cell Biol. Jun. 1996;133(5):1061-9.
Xu, et al. Overexpression of neurofilament subunit M accelerates axonal transport of neurofilaments. Brain Res. Jun. 2, 2000;866(1-2):326-32.
Zhang, et al. Human traumatic brain injury induces autoantibody response against glial fibrillary acidic protein and its breakdown products. PLoS One. 2014, 9(3):e92698.
Szaro, et al. Post-transcriptional control of neurofilaments: New roles in development, regeneration and neurodegenerative disease. Trends Neurosci. Jan. 2010;33(1):27-37.
GenBank Accession No. CAA55016, NCBI Oct. 7, 2008.
Altschul, et al., Gapped BLAST and PSI-BLAST: A new generation of protein database search programs. Nucleic Acids Res. Sep. 1, 1997;25(17):3389-402.
Antony, et al., Hypothesis: folate-responsive neural tube defects and neurocristopathies. Teratology. Jul. 2000;62(1):42-50.
Antony, et al., Identification of high affinity folate binding proteins in human erythrocyte membranes. J Clin Invest. Sep. 1987;80(3):711-23.
Antony, et al., Isolation and characterization of a folate receptor from human placenta. J Biol Chem. Sep. 25, 1981;256(18):9684-92.
Antony, et al., Effect of perturbation of specific folate receptors during in vitro erythropoiesis. J Clin Invest. Dec. 1987;80(6):1618-23.
Antony, et al., Translational upregulation of folate receptors is mediated by homocysteine via RNA-heterogeneous nuclear ribonucleoprotein E1 interactions. J Clin Invest. Jan. 2004;113(2):285-301.
Baker, et al., Diagnosis and prevention of iron deficiency and iron-deficiency anemia in infants and young children (0-3 years of age). Pediatrics. Nov. 2010;126(5):1040-50.
Batzer, et al., Enhanced evolutionary PCR using oligonucleotides with inosine at the 3'-terminus. Nucleic Acids Res. Sep. 25, 1991;19(18):5081.
Boshnjaku, et al., Nuclear localization of folate receptor alpha: a new role as a transcription factor. Sci Rep.2012, 2:980.
Brunette, et al., Gestational and neonatal iron deficiency alters apical dendrite structure of CA1 pyramidal neurons in adult rat hippocampus. Dev Neurosci. Aug. 2010;32(3):238-48.
Chang, et al., Iron-deficiency anemia in infancy and social emotional development in preschool-aged Chinese children. Pediatrics. Apr. 2011;127(4):e927-33.
Chappell, et al., A mutation in the c-myc-IRES leads to enhanced internal ribosome entry in multiple myeloma: a novel mechanism of oncogene de-regulation. Oncogene. Sep. 7, 2000;19(38):4437-40.
Chaudhury, et al, Heterogeneous nuclear ribonucleoproteins (hnRNPs) in cellular processes: Focus on hnRNP E1's multifunctional regulatory roles. RNA. Aug. 2010;16(8):1449-62.
Chkheidze, et al. Assembly of the alpha-globin mRNA stability complex reflects binary interaction between the pyrimidine-rich 3' untranslated region determinant and poly(C) binding protein alphaCP. Mol Cell Biol. Jul. 1999;19(7):4572-81.
Christian, et al. Prenatal micronutrient supplementation and intellectual and motor function in early school-aged children in Nepal. Jama. Dec. 22, 2010;304(24):2716-23.
Collier, et al. Translational inhibition in vitro of human papillomavirus type 16 L2 mRNA mediated through interaction with heterogenous ribonucleoprotein K and poly(rC)-binding proteins 1 and 2. J Biol Chem. Aug. 28, 1998;273(35):22648-56.
Ohtsuka, et al. An alternative approach to deoxyoligonucleotides as hybridization probes by insertion of deoxyinosine at ambiguous codon positions. J Biol Chem. Mar. 10, 1985;260(5):2605-8.
Czyzyk-Krzeska, et al. Characterization of the hypoxia-inducible protein binding site within the pyrimidine-rich tract in the 3'-untranslated region of the tyrosine hydroxylase mRNA. J Biol Chem. Feb. 9, 1996;271(6):3293-9.

(56) References Cited

OTHER PUBLICATIONS

Czyzyk-Krzeska, et al. Post-transcriptional regulation of tyrosine hydroxylase gene expression by oxygen in PC12 cells. Kidney Int. Feb. 1997;51(2):585-90.

Czyzyk-Krzeska, et al. Identification of the poly(C) binding protein in the complex associated with the 3' untranslated region of erythropoietin messenger RNA Blood. Mar. 15, 1999;93(6):2111-20.

Darnell, et al. Paraneoplastic syndromes affecting the nervous system. Semin Oncol. Jun. 2006;33(3):270-98.

Darnell RB. Onconeural antigens and the paraneoplastic neurologic disorders: at the intersection of cancer, immunity, and the brain. Proc Natl Acad Sci U S A. May 14, 1996;93(10):4529-36.

Dejgaard, et al. Characterisation of the nucleic-acid-binding activity of KH domains. Different properties of different domains. Eur J Biochem. Oct. 15, 1996;241(2):425-31.

Dobbyn, et al. Regulation of BAG-1 IRES-mediated translation following chemotoxic stress. Oncogene. Feb. 14, 2008;27(8):1167-74.

Ferguson, et al. Behavioral effects of prenatal folate deficiency in mice. Birth Defects Res A Clin Mol Teratol. Apr. 2005;73(4):249-52.

Georgieff MK. Long-term brain and behavioral consequences of early iron deficiency. Nutr Rev. Nov. 2011;69 Suppl 1: S43-8.

Ghanem, et al. Specific enrichment of the RNA-binding proteins PCBP1 and PCBP2 in chief cells of the murine gastric mucosa. Gene Expr Patterns. Mar. 2014;14(2):78-87.

Giles, et al. The 3'-untranslated region of p21WAF1 mRNA is a composite cis-acting sequence bound by RNA-binding proteins from breast cancer cells, including HuR and poly(C)-binding protein. J Biol Chem. Jan. 31, 2003;278(5):2937-46.

Henikoff, et al. Amino acid substitution matrices from protein blocks. Proc Natl Acad Sci U S A. Nov. 15, 1992;89(22):10915-9.

Hider, et al. Iron speciation in the cytosol: an overview. Dalton Trans. Mar 7, 2013;42(9):3220-9.

Hider, et al. Glutathione: a key component of the cytoplasmic labile iron pool. Biometals. Dec. 2011;24(6):1179-87.

Holcik, et al. XIAP, the guardian angel. Nat Rev Mol Cell Biol. Jul. 2001;2(7):550-6.

Jiang, et al. A nucleolin-binding 3' untranslated region element stabilizes beta-globin mRNA in vivo. Mol Cell Biol. Mar. 2006;26(6):2419-29.

Keene JD. RNA regulons: coordination of post-transcriptional events. Nat Rev Genet Jul. 2007;8(7):533-43.

Kiledjian, et al. Identification of two KH domain proteins in the alpha-globin mRNP stability complex. Embo J. Sep. 1, 1995;14(17):4357-64.

Kong, et al. Antagonistic roles of neurofilament subunits NF-H and NF-M against NF-L in shaping dendritic arborization in spinal motor neurons. J Cell Biol. Mar. 9, 1998;140(5):1167-76.

Leamon, et al. Impact of high and low folate diets on tissue folate receptor levels and antitumor responses toward folate-drug conjugates. J Pharmacol Exp Ther. Dec. 2008;327(3):918-25.

Leffers, et al. Characterisation of two major cellular poly(rC)-binding human proteins, each containing three K-homologous (KH) domains. Eur J Biochem. Jun. 1, 1995;230(2):447-53.

Lewis, et al. Subcellular relocalization of a trans-acting factor regulates XIAP IRES-dependent translation. Mol Biol Cell. Apr. 2007;18(4):1302-11.

Lewis, et al. For IRES trans-acting factors, it is all about location. Oncogene. Feb. 14, 2008;27(8):1033-5.

Lozoff, et al. Poorer behavioral and developmental outcome more than 10 years after treatment for iron deficiency in infancy. Pediatrics. Apr. 2000;105(4):E51.

Lozoff. et al. Long-term developmental outcome of infants with iron deficiency. N Engl J Med. Sep. 5, 1991;325(10):687-94.

Lozoff, et al. Behavioral and developmental effects of preventing iron-deficiency anemia in healthy full-term infants. Pediatrics. Oct. 2003;112(4):846-54.

Lungwitz, et al. Polyethylenimine-based non-viral gene delivery systems. Eur J Pharm Biopharm. Jul. 2005;60(2):247-66.

Makeyev, et al. The poly(C)-binding proteins: a multiplicity of functions and a search for mechanisms. Rna. Mar. 2002;8(3):265-78.

Mandal, et al. Reprogramming human fibroblasts to pluripotency using modified mRNA. Nat Protoc. Mar. 2013;8(3):568-82.

Meng, et al. Signaling-dependent and coordinated regulation of transcription, splicing, and translation resides in a single coregulator, PCBP1. Proc Natl Acad Sci U S A. Apr. 3, 2007;104(14):5866-71.

Monk, et al. Research review: maternal prenatal distress and poor nutrition—mutually influencing risk factors affecting infant neurocognitive development. J Child Psychol Psychiatry. Feb. 2013;54(2):115-30.

Musunuru, et al. Determination and augmentation of RNA sequence specificity of the Nova K-homology domains. Nucleic Acids Res. 2004;32(16):4852-61.

FIGS. 1A-1E
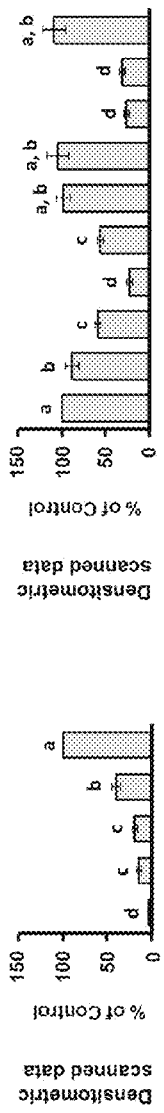
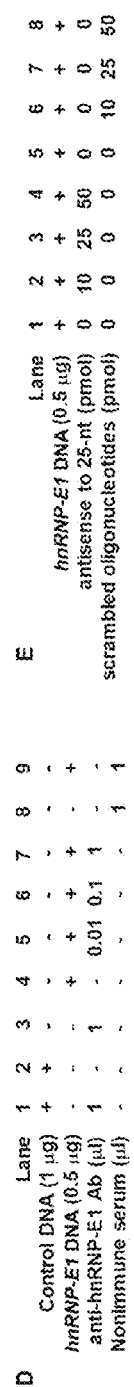

FIGS. 9A-9C
A Sequence of Peptides Used
for Making Anti-hnRNPE1 Antiserum
| hnRNP-E1: | SLAQYLINARLSSEKGMGC | (SEQ ID NO:72) |
| | SLAQYLIN RLSSE G | (SEQ ID NO:73) |
| hnRNP-E2: | SLAQYLINVRLSSETGGMG | (SEQ ID NO:74) |
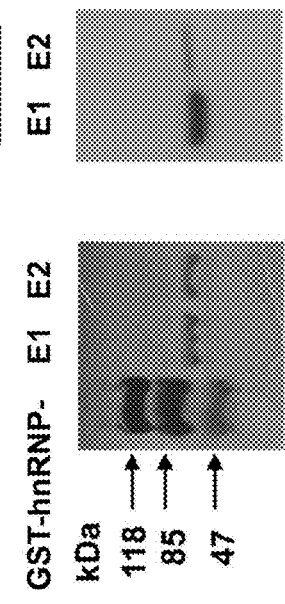
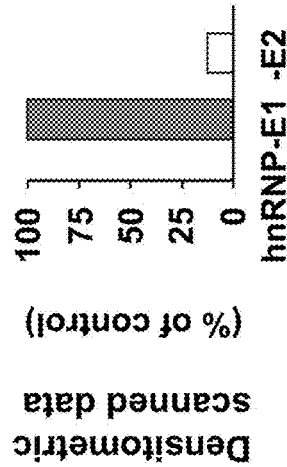

DOMINANT POSITIVE HNRNP-E1 POLYPEPTIDE COMPOSITIONS AND METHODS

STATEMENT REGARDING FEDERALLY SPONSORED RESEARCH

This invention was made with government support under CA120843 and HD039295 awarded by National Institutes of Health and BX002027 merit award by the Veterans Administration. The government has certain rights in the invention.

CROSS-REFERENCE TO RELATED APPLICATIONS

Not applicable.

BACKGROUND

Cellular folate deficiency induces a number of homeostatic physiological changes to restore cellular folate levels, including the upregulation of folate receptor levels. An initial consequence of folate deficiency is an increase in intracellular homocysteine levels that results in the homocysteinylation of the multifunctional heterogeneous nuclear ribonucleoprotein protein-E1 (hnRNP-E1). Homocysteinylation of hnRNP-E1 forms cysteine-S-S mixed disulfide bonds, which unmasks a cryptic mRNA-binding site that is capable of binding to diverse mRNAs characterized as having a common poly(rC)/poly(U)-rich cis element. Binding of homocysteinylated hnRNP-E1 to poly(rC)/(U)-containing mRNAs, including the folate receptor-alpha (folate receptor-α) mRNA, leads to an increase in translation on the mRNAs and a net increase in their corresponding protein levels. Thus, the capability to control the binding of hnRNP-E1 to the poly(rC)/(U)-containing mRNAs independent of homocystein may be useful to alter the expression of a subset of proteins for the treatment of a number of health conditions.

BRIEF SUMMARY

Described herein are compositions relating to variant hnRNP-E1 polypeptides and methods of use thereof. The compositions and methods are based on the unexpected finding that particular point mutations in hnRNP-E1 confer homocysteine-independent binding of the variant hnRNP-E1 to its target poly(rC)/poly(U)-rich cis element-containing mRNAs to modulate their translation.

In a first aspect disclosed herein is a polypeptide having an RNA binding portion at least 90% identical to any of SEQ ID NOs:1-5, the RNA binding portion comprising an amino acid substitution at at least one position selected from the group consisting of positions 293, 54, 158, 201 relative to SEQ ID NO:1, the RNA binding portion being optionally linked to a protein transduction domain, wherein the RNA binding portion binds a single-stranded RNA that comprises SEQ ID NO:6.

In some embodiments, the polypeptide binds the single-stranded RNA comprising SEQ ID NO:6 independent of homocysteine concentration.

In some embodiments, the at least one amino acid substitution is a serine. In some embodiments, the RNA binding portion is at least 95% identical to any of SEQ ID NOs:2-5. In other embodiments, the RNA binding portion is selected from the group consisting of SEQ ID NOs:2-5. In one embodiment, the RNA binding portion is SEQ ID NO:2.

In some embodiments, the RNA binding portion is linked to the protein transduction domain. In some embodiments, the protein transduction domain comprises any of SEQ ID NOs:7-11.

In some embodiments of the first aspect, the polypeptide is part of a pharmaceutical composition comprising a suitable polypeptide as described herein and a pharmaceutically acceptable carrier.

In some embodiments of the first aspect, the polypeptide is encoded by a nucleic acid. In some embodiments, the nucleic acid is an RNA. In some embodiments, the RNA is a synthetic mRNA comprising modified ribonucleotides.

In some embodiments of the first aspect, the nucleic acid encoding the polypeptide as described in the above embodiments is included in a pharmaceutical composition comprising a suitable nucleic acid as described herein, a transfection reagent, and a pharmaceutically acceptable excipient.

In some embodiments of the first aspect, the nucleic acid encoding the polypeptide as described in the above embodiments is included in a nucleic acid expression vector.

In some embodiments of the first aspect, the nucleic acid encoding the polypeptide as described in the above embodiments is included in a recombinant virus.

In some embodiments of the first aspect, the nucleic acid encoding the polypeptide as described in the above embodiments is included in a cell. In some embodiments the cell further comprises the polypeptide encoded by the nucleic acid. In some embodiments, the cell is selected from the group consisting of a bacterial cell and a mammalian cell.

In a second aspect disclosed herein is a method for increasing translation of a target mRNA in a mammalian cell, the method comprising the step of providing in the mammalian cell a suitable polypeptide as described in the embodiments herein, wherein the target mRNA comprises a poly(rC)- and poly(U)-rich 5' UTR, thereby increasing translation of the target mRNA in the mammalian cell.

In some embodiments, the providing step is selected from the group consisting of administering the polypeptide to the cell and expressing the polypeptide within the cell. In some embodiments, the expressing step includes delivering into the mammalian cell a nucleic acid encoding the polypeptide whereby the polypeptide is expressed.

In some embodiments of the second aspect, the target mRNA is selected from the group consisting of folate receptor mRNA, hnRNP-E1 mRNA, collagen alpha (I) mRNA, human papillomavirus type 16 L2 mRNA, human herpesvirus 8 mRNA, erythropoietin mRNA, human alpha-globin mRNA, human beta-globin mRNA, μ-opioid receptor mRNA, androgen receptor mRNA, p21waf mRNA, tyrosine hydroxylase mRNA, and neurofilament M mRNA.

In a third aspect disclosed herein is a method for treating a health condition by administering a therapeutically effective amount of a pharmaceutical composition to a subject in need thereof, the pharmaceutical composition comprising a suitable polypeptide as described in the embodiments herein; or a nucleic acid encoding the polypeptide; wherein the health condition is selected from the group consisting of: HPV infection, Kaposi's sarcoma, anemia, a skin condition, alpha-thalassemia, beta thalassemia, chronic pain, androgen deficiency, a tumor, Parkinson's disease, and a nerve injury.

In some embodiments of the third aspect, the polypeptide comprises SEQ ID NO:2. In some embodiments, the nucleic acid encodes a polypeptide comprising SEQ ID NO:2.

In some embodiments of the third aspect, the skin condition comprises a wound. In some embodiments, the pharmaceutical composition is administered topically.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BRIEF DESCRIPTION OF THE DRAWINGS

This patent application file contains at least one drawing executed in color. Copies of this patent or patent application publication with color drawings will be provided by the Office upon request and payment of the necessary fee.

The present invention will be better understood and features, aspects and advantages other than those set forth above will become apparent when consideration is given to the following detailed description thereof. Such detailed description makes reference to the following drawings, wherein:

FIGS. 1A-1E characterizes the interaction in vitro between purified hnRNP-E1 and a 25-nt cis-element in the 5'-UTR of hnRNP-E1 mRNA. (A) Location of the candidate 25-nt cis-element [capitalized] in the 5'-UTR of hnRNP-E1 from −145 to −120 from the ATG start site. (B) Gel-shift analysis of the interaction between the 25-nt cis-element of hnRNP-E1 mRNA indicated in A (radiolabeled) and either purified recombinant GST-hnRNP-E1 (lanes 1, 3, 6-10) or engineered hnRNP-E1 variants (lanes 4, 5) in the absence or presence of L-homocysteine; Super-shift of the RNA-protein signal on the gel in the presence of anti-hnRNP-E1 antiserum is shown in lane 1. (C) In vitro translation of hnRNP-E1 mRNA after quenching excess thiols in the reaction mixture by N-ethylmaleimide (NEM) (lanes 2-4) to assess the effect of increasing L-homocysteine on hnRNP-E1 (lanes 5-7), and comparison of the independent effect on wild-type or engineered hnRNP-E1 variants (lanes 8-10). (D) Demonstration of the key role of hnRNP-E1 in mediating in vitro translation of hnRNP-E1 protein by addition of anti-hnRNP-E1 antiserum (lanes 4-7). Lanes 1 and 2 were internal protein controls. (E) Comparison of the in vitro hnRNP-E1 translation-quenching effectiveness of oligonucleotides having an antisense sequence relative to the 25-nt hnRNP-E1 cis-element and scrambled oligonucleotides. The autoradiograms shown in B, C, D, and E are representative of 3 separate experiments and pooled densitometric scanned data of signals are compared to the 100% value. The result is presented as the mean±SD, n=3 (means of triplicates). Labeled means without a common letter differ, P<0.05. Anti-hnRNP-E1 ab, anti-hnRNP-E1 antiserum; wild-type hnRNP-E1; hnRNP-E1(G292A), wild-type-like hnRNP-E1(G292A)-mutant; hnRNP-E1(C293S), highest affinity (HA)-hnRNP-E1(C2923S)-mutant; NEM, N-ethylmaleimide; 25-nt, 25-nucleotide hnRNP-E1 mRNA cis-element.

FIGS. 9A-9C depict the sequence of peptides of hnRNP-E1 used to generate anti-hnRNP-E1 antiserum and a corresponding sequence of peptides in hnRNP-E2 (A). The common peptides are shown in the middle row. After confirmation of the purity of recombinant GST-hnRNP-E1 and GST-hnRNP-E2 by SDS-PAGE (B), the specificity of the anti-hnRNP-E1 antiserum was tested against equivalent amounts of these proteins by Western blots (C). Comparison of the densitometric scan of each band generated by anti-hnRNP-E1 antiserum reacting with equivalent amount of hnRNP-E1 (closed bar) and hnRNP-E2 (open bar) is shown below is shown below the gel in C. The signal following reaction of anti-hnRNP-E1 antiserum with hnRNP-E1 was assigned 100%, allowing for a comparison with the corresponding signal when anti-hnRNP-E1 antiserum was reacted with hnRNP-E2.anti-E1, anti-hnRNP-E1 antiserum; hnRNP-E2 & E2, heterogeneous nuclear ribonucleoprotein E2; GST, glutathione S-transferase; hnRNP-E1 & E1, heterogeneous nuclear ribonucleoprotein E1.

FIG. 10A show the three color-coded K-homology domains within the amino acid sequence of hnRNP-E1. The mutated amino acid residues are capitalized in red and underlined.

FIG. 10B shows purified recombinant wild-type GST-hnRNP-E1, and various mutants of hnRNP-E1 (pE1) containing single substitutions where cysteine was replaced with serine at the following positions (C54S; C109S; C118S; C158S; C163S; C194S; C201S; C293S; or C355S) or where glycine was replaced by alanine at position 292 (G292A). Western blots were probed with anti-hnRNP-E1 antiserum. Non-immune serum gave no signal (not shown).

FIG. 10C shows gel-shift analysis of the interaction of 18-nt folate receptor-α mRNA cis-element (1×10$^5$ cpm) and various purified recombinant GST-hnRNP-E1 proteins from FIG. 10B in the absence of homocysteine or other reducing agents, such as DTT and β-ME. Shown are representative data from comparable results of studies carried out at least 3 times.

FIGS. 10D-10E show verification of significant quenching of in vitro translation of [$^{35}$S]folate receptor proteins by increasing concentrations of N-ethylmaleimide (NEM) and restoration of the translation of folate receptor proteins by addition of various purified recombinant wild-type and mutant hnRNP-E1 proteins in the presence of 2 mM NEM.

FIG. 10F depicts the effect of wild-type or mutant hnRNP-E1 plasmids on CAT reporters placed downstream from an 18-nt folate receptor-α mRNA cis-element in HeLa-IU$_1$-HF cells. pSV-β-gal was used as an internal control, and the chemiluminescent assay for quantitative determination of β-galactosidase activity in transfected cells was employed to monitor transfection efficiency. All data were normalized by internal standard and protein content of each treatment. The data are presented as the mean±SD. The asterisk (*) signifies P<0.05 between variables.

FIG. 10G shows gel-shift analysis of the interaction of HPV16 L2 mRNA cis-element (1×10$^5$ cpm) and various purified recombinant GST-hnRNP-E1 proteins from FIG. 10B in the absence of reducing agents. Shown are representative data from comparable results of studies carried out at least 3 times. Construction of plasmids for generation of HPV16 L2 RNA, gel-shift and in vitro translation studies were carried as described with additional treatments shown.

FIG. 10H shows a comparison of the dose-response effect of wild-type hnRNP-E1 and bovine serum albumin (BSA) on the in vitro translation of [$^{35}$S]HPV16 L2 protein in the absence of NEM, and effectiveness of various hnRNP-E1 mutants in quenching translation of [$^{35}$S]HPV16 L2 protein in the presence of 2 mM NEM. In each of two panels, the pooled densitometric scanned data of [$^{35}$S]HPV16 L2 protein synthesized from 3 independent experiments are shown as a bar graph below one representative gel. The stability of HPV16 L2 RNA within the in vitro translation mixture was not affected.

FIG. 11A shows Western blots of samples from each cell line (1584, JAR, and CCL98) that was propagated long-term in either high-folate or low-folate media for over 12-weeks and probed by anti-FR antiserum. The bar graph shown below the blots represents densitometric analysis of the protein signals in high-versus low-folate media.

FIG. 11B shows FR mRNA expression using qRT-PCR in placental cells propagated in high-versus low-folate medium.

FIG. 11C shows Western blots of samples from each placental cell line (1584, JAR, and 7526) stably propagated long-term in either high- or low-folate media for over 12-weeks and probed by anti-hnRNP-E1 antiserum. The bar graph shown below the blots represents densitometric analysis of the protein signals in high- and low-folate media.

FIG. 11D depicts analysis for hnRNP-E1 mRNA by qRT-PCR in placental cell lines stably propagated in high-versus low-folate media.

DETAILED DESCRIPTION

Figures 2A, 2B, 2C, 2D, 2E:
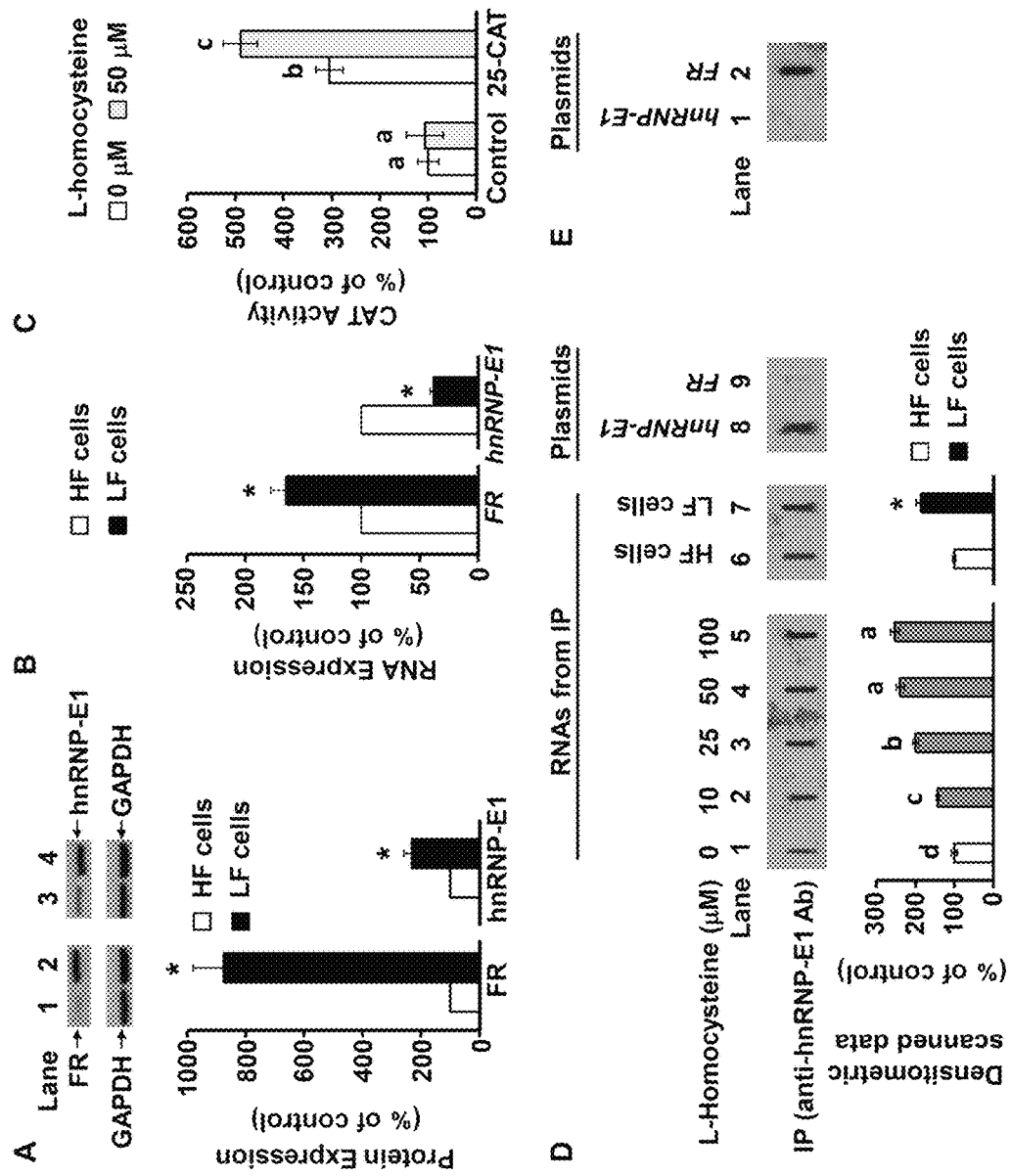
FIGS. 2A-2E shows evidence for post-transcriptional up-regulation in response to homocysteine in placental 1584 cells of hnRNP-E1 (A, B) and for interaction between endogenous hnRNP-E1 proteins and a 25-nt hnRNP-E1 mRNA cis-element (C, D, E). (A) Western blots of placental 1584-HF cells (lanes 1, 3) and 1584-LF cells (lanes 2, 4) probed for folate receptor-α (FR) and hnRNP-E1. One representative blot of 3 independent experiments is shown; the result of densitometric scanning analysis is presented below the gels as the mean±SD from three independent gels. (B) Comparison of the folate receptor-α RNA and hnRNP-E1 RNA from 1584-HF and 1584-LF cells. (C) Chloramphenicol acetyltransferase (CAT) reporter activity following transfection of either a pCAT construct (denoted 'control') or a 25-nt hnRNP-E1 cis-element-driven CAT reporter construct (denoted '25-CAT') into 1584-HF cells before (open bars) and after exposure to 50-μM L-homocysteine (shaded bars). The results are presented as the mean±SD from 3 independent sets of experiments with each data point performed in triplicate. (D) Slot-blot hybridization analysis using a [$^{35}$S]-labeled antisense probe to the 25-nt RNA cis-element (to detect intracellular RNA-protein complexes composed of the 25-nt hnRNP-E1 RNA cis-element bound to hnRNP-E1) after 2-hour exposure of placental 1584-HF cells to increasing concentrations of L-homocysteine (lanes 1-5), or under basal conditions in 1584-HF and 1584-LF cells (lanes 6 and 7). The 25-nt antisense probe was reacted with hnRNP-E1 plasmid and a folate receptor-α plasmid (lanes 8, 9) showing specificity of the probe for the 25-nt RNA cis-element of hnRNP-E1. (E) Reaction of a [$^{35}$S]-18-nt folate receptor-α mRNA cis-element probe with a folate receptor-α plasmid (lane 2) or hnRNP-E1 plasmid (lane 1). The result of densitometric scans of the signals is shown below the slot-blot and is presented as the mean±SD from 3 independent sets of experiments. The 100% control value is indicated by the # symbol. Labeled means without a common letter differ, P<0.05. CAT, chloramphenicol acetyltransferase; FR, human folate receptor-α; GAPDH, glyceraldehyde-3-phosphate dehydrogenase; HF cells, placental 1584 cells stably adapted to high folate; LF cells, placental 1584 cells stably adapted to low folate; IP immunoprecipitation with anti-hnRNP-E1 antiserum; ab, antiserum.

Described herein are compositions relating to engineered hnRNP-E1 isoforms and methods for their use. The compositions and methods are based on the unexpected finding that particular point mutations in hnRNP-E1 confer homocysteine-independent binding of engineered hnRNP-E1 to its target poly(rC)/poly(U)-rich cis element-containing mRNAs to upregulate their translation.

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, the preferred methods and materials are described herein.

Definitions

In describing the embodiments and claiming the invention, the following terminology will be used in accordance with the definitions set out below.

As used herein, an "agent" includes any substance that is useful in producing an effect, including a physiological or biochemical effect in an organism. A "therapeutic agent" is a substance that produces or is intended to produce a therapeutic effect, i.e., an effect that leads to amelioration, prevention, and/or complete or partial cure of a disorder. A "therapeutic effect," as that term is used herein, also includes the production of a condition that is better than the average or normal condition in an individual that is not suffering from a disorder, i.e., a supranormal effect such as improved cognition, memory, mood, or other characteristic attributable at least in part to the functioning of the CNS, compared to the normal or average state.

"Treatment" or "treating" as used herein includes achieving a therapeutic benefit and/or a prophylactic benefit. By therapeutic benefit is meant eradication or amelioration of the underlying disorder or condition being treated. Also, a therapeutic benefit is achieved with the eradication or amelioration of one or more of the physiological or psychological symptoms associated with the underlying condition such that an improvement is observed in the patient, notwithstanding the fact that the patient may still be affected by the condition. A prophylactic benefit of treatment includes prevention of a condition, retarding the progress of a condition (e.g., slowing the progression of a disorder), or decreasing the likelihood of occurrence of a condition. As used herein, "treating" or "treatment" includes prophylaxis.

As used herein, the term "effective amount" can be an amount sufficient to effect beneficial or desired results, such as beneficial or desired clinical results. An effective amount is also an amount that produces a prophylactic effect, e.g., an amount that delays, reduces, or eliminates the appearance of a pathological or undesired condition. An effective amount can be administered in one or more administrations. In terms of treatment, an "effective amount" of a composition of the invention is an amount that is sufficient to palliate, ameliorate, stabilize, reverse or slow the progression of a health condition, e.g., a wound. An "effective amount" may be of any of the compositions of the invention used alone or in conjunction with one or more agents used to treat a disease or disorder. An "effective amount" of a therapeutic agent within the meaning of the present invention will be determined by a patient's attending physician or veterinarian. Such amounts are readily ascertained by one of ordinary skill in the art and will a therapeutic effect when administered in accordance with the present invention. Factors which influence what a therapeutically effective amount will be include, the specific activity of the therapeutic agent being used, the type of disorder (e.g., acute vs. chronic health condition), time elapsed since the onset of the health condition, and the age, physical condition, existence of other disease states, and nutritional status of the individual being treated. Additionally, other medication the patient may be receiving will affect the determination of the therapeutically effective amount of the therapeutic agent to administer.

A "subject" or an "individual," as used herein, is a mammal, for example, a rodent. In some embodiments a "subject" or an "individual" is a human.

In some embodiments, an agent is "administered peripherally" or "peripherally administered." Peripheral administration," as used herein, includes topical, intravenous, subcutaneous, intramuscular, intraperitoneal, transdermal, inhalation, transbuccal, intranasal, rectal, and oral administration.

A "pharmaceutically acceptable carrier" or "pharmaceutically acceptable excipient" herein refers to any carrier that does not itself induce the production of antibodies harmful to the individual receiving the composition. Such carriers are well known to those of ordinary skill in the art. A thorough discussion of pharmaceutically acceptable carriers/excipients can be found in Remington's Pharmaceutical Sciences, Gennaro, A R., ed., 20th edition, 2000: Williams and Wilkins PA, USA. Exemplary pharmaceutically acceptable carriers can include salts, for example, mineral acid salts such as hydrochlorides, hydrobromides, phosphates, sulfates, and the like; and the salts of organic acids such as acetates, propionates, malonates, benzoates, and the like. For example, compositions of the invention may be provided in liquid form, and formulated in saline based aqueous solution of varying pH (5-8), with or without detergents such polysorbate-80 at 0.01-1%, or carbohydrate additives, such mannitol, sorbitol, or trehalose. Commonly used buffers include histidine, acetate, phosphate, or citrate.

A "genetically modified cell" or "host cell" refers to a prokaryotic or eukaryotic cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally occurring amino acid, e.g., an amino acid analog. As used herein, the terms encompass amino acid chains of any length, including full length proteins (i.e., antigens), wherein the amino acid residues are linked by covalent peptide bonds.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to compounds that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

The term "engineered hnRNP-E1 variant polypeptide" refers to a polypeptide consisting of at least the amino acid sequence of an hnRNP-E1 with at least one amino acid substitution, but also encompasses a fusion polypeptide comprising additional amino acids (e.g., the sequence of a protein transduction domain) fused to the N-terminal or C-terminal of the hnRNP-E1 amino acid sequence).

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Cassol et al. (1992); Rossolini et al., Mol. Cell. Probes 8:91-98 (1994)).

The terms "isolated" and "purified" refer to a material that is substantially or essentially removed from or concentrated in its natural environment. For example, an isolated nucleic acid may be one that is separated from the nucleic acids that normally flank it or other nucleic acids or components (proteins, lipids, etc.) in a sample. In another example, a polypeptide is purified if it is substantially removed from or concentrated in its natural environment. Methods for purification and isolation of nucleic acids and peptides are well known in the art.

With respect to the amino acid sequence homology of polypeptides described herein, one of ordinary skill in the art will appreciate that structural and functional homology of two or more polypeptides generally includes determining the percent identity of their amino acid sequences to each other. Sequence identity between two or more amino acid sequences is determined by conventional methods. See, for example, Altschul et al., (1997), *Nucleic Acids Research*, 25(17):3389-3402; and Henikoff and Henikoff (1982), *Proc. Natl. Acad. Sci. USA*, 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.). The percent identity is then calculated as: ([Total number of identical matches]/[length of the longer sequence plus the number of gaps introduced into the longer sequence in order to align the two sequences])(100).

Compositions

Described herein are engineered hnRNP-EI variant polypeptides comprising a point mutation that confers homocysteine-independent binding to a poly(rC)/poly(U)-rich cis element-rich 5'UTR motif. Also described are nucleic acids that encode the aforementioned polypeptides.

Accordingly, disclosed herein is a purified polypeptide comprising an hnRNP-E1 amino acid sequence at least about 85% to identical any of SEQ ID NOs:2-5, wherein the purified polypeptide comprises a substitution at a position selected from the group consisting of C293, C54, C158, C201, C118, C163 or combinations thereof relative to SEQ ID NO:1 and binds a single-stranded RNA comprising SEQ ID NO:6 under conditions independent of homocysteine.

The substitution at a position selected from the group consisting of C293, C54, C158, C201, C118, C163 or combinations thereof relative to SEQ ID NO:1 may be a substitution to any other amino acid that does not form a disulfide bond. In some embodiments, the substitution is a serine and is selected from the group consisting of C293S, C54S, C158S, C201S or combinations thereof relative to SEQ ID NO:1.

In some embodiments the polypeptide comprise an amino acid sequence that is at least 85% to about 100% identical to any of SEQ ID NOs:2-6, e.g., about 86%, 87%, 88%, 90%, 92%, 94%, 95%, 96%, 97%, or another percent from about 85% to about 100% identical to any of SEQ ID NOs:2-5 insofar as the amino acid sequence of the polypeptide comprises a substitution at amino acid positions C293, C54, C158, C201, C118, or C163 relative to SEQ ID NO:1. In some embodiments, the polypeptide comprises an amino acid sequence that is at least 95% identical to any of SEQ ID NOs:2-5, and comprises a C293S, a C54S, a C158S, a C201S, a C118S, or a C163S substitution relative to SEQ ID NO:1. In other embodiments, the polypeptide comprises any of SEQ ID NOs:2-5. In further embodiments, the amino acid sequence of the polypeptide consists any of SEQ ID NOs: 2-5.

In some embodiments, the polypeptide comprising an amino acid sequence that is at least about 85% to about 100% identical to SEQ ID NO:2, and comprises a C293 substitution relative to SEQ ID NO:1. In some embodiments, the amino acid sequence comprises a C293 S substitution. In some embodiments, the amino acid sequence of the polypeptide comprises an amino acid sequence at least 90% identical to SEQ ID NO:2 and comprises a C293S substitution. In other embodiments, the amino acid sequence of the polypeptide comprises an amino acid sequence at least 95% identical to SEQ ID NO:2 and comprises a C293S substitution. In yet other embodiments, the amino acid sequence of the encoded polypeptide comprises SEQ ID NO:2. In one embodiment, the encoded polypeptide is SEQ ID NO:2.

The amino acid sequence of wild-type human hnRNP-E1 (GenBank Accession No. CAA5016) is provided below as SEQ ID NO:1:

```
(wild-type human hnRNP-E1-GenBank Accession No.
CAA5016)
                                          SEQ ID NO: 1
MDAGVTESGLNVTLTIRLLMHGKEVGSIIGKKGESVKRIREESGARINIS

EGNCPERIITLTGPTNAIFKAFAMIIDKLEEDINSSMTNSTAASRPPVTL

RLVVPATQCGSLIGKGGCKIKEIRESTGAQVQVAGDMLPNSTERAITIAG

VPQSVTECVKQICLVMLETLSQSPQGRVMTIPYQPMPASSPVICAGGQDR

CSDAVGYPHATHDLEGPPLDAYSIQGQHTISPLDLAKLNQVARQQSHFAM

MHGGTGFAGIDSSSPEVKGYWASLDASTQTTHELTIPNNLIGCIIGRQGA

NINEIRQMSGAQIKIANPVEGSSGRQVTITGSAASISLAQYLINARLSSE

KGMGCS (hnRNP-E1 C293S)
                                          SEQ ID NO: 2
MDAGVTESGLNVTLTIRLLMHGKEVGSIIGKKGESVKRIREESGARINIS

EGNCPERIITLTGPTNAIFKAFAMIIDKLEEDINSSMTNSTAASRPPVTL

RLVVPATQCGSLIGKGGCKIKEIRESTGAQVQVAGDMLPNSTERAITIAG

VPQSVTECVKQICLVMLETLSQSPQGRVMTIPYQPMPASSPVICAGGQDR

CSDAVGYPHATHDLEGPPLDAYSIQGQHTISPLDLAKLNQVARQQSHFAM

MHGGTGFAGIDSSSPEVKGYWASLDASTQTTHELTIPNNLIGSIIGRQGA

NINEIRQMSGAQIKIANPVEGSSGRQVTITGSAASISLAQYLINARLSSE

KGMGCS (hnRNP-E1 C54S)
                                          SEQ ID NO: 3
MDAGVTESGLNVTLTIRLLMHGKEVGSIIGKKGESVKRIREESGARINIS

EGNSPERIITLTGPTNAIFKAFAMIIDKLEEDINSSMTNSTAASRPPVTL

RLVVPATQCGSLIGKGGCKIKEIRESTGAQVQVAGDMLPNSTERAITIAG

VPQSVTECVKQICLVMLETLSQSPQGRVMTIPYQPMPASSPVICAGGQDR

CSDAVGYPHATHDLEGPPLDAYSIQGQHTISPLDLAKLNQVARQQSHFAM
```

-continued
MHGGTGFAGIDSSSPEVKGYWASLDASTQTTHELTIPNNLIGCIIGRQGA

NINEIRQMSGAQIKIANPVEGSSGRQVTITGSAASISLAQYLINARLSSE

KGMGCS (hnRNP-E1 C158S)
SEQ ID NO: 4
MDAGVTESGLNVTLTIRLLMHGKEVGSIIGKKGESVKRIREESGARINIS

EGNCPERIITLTGPTNAIFKAFAMIIDKLEEDINSSMTNSTAASRPPVTL

RLVVPATQCGSLIGKGGCKIKEIRESTGAQVQVAGDMLPNSTERAITIAG

VPQSVTESVKQICLVMLETLSQSPQGRVMTIPYQPMPASSPVICAGGQDR

CSDAVGYPHATHDLEGPPLDAYSIQGQHTISPLDLAKLNQVARQQSHFAM

MHGGTGFAGIDSSSPEVKGYWASLDASTQTTHELTIPNNLIGCIIGRQGA

NINEIRQMSGAQIKIANPVEGSSGRQVTITGSAASISLAQYLINARLSSE

KGMGCS (hnRNP-E1 C201S)
SEQ ID NO: 5
MDAGVTESGLNVTLTIRLLMHGKEVGSIIGKKGESVKRIREESGARINIS

EGNCPERIITLTGPTNAIFKAFAMIIDKLEEDINSSMTNSTAASRPPVTL

RLVVPATQCGSLIGKGGCKIKEIRESTGAQVQVAGDMLPNSTERAITIAG

VPQSVTECVKQICLVMLETLSQSPQGRVMTIPYQPMPASSPVICAGGQDR

SSDAVGYPHATHDLEGPPLDAYSIQGQHTISPLDLAKLNQVARQQSHFAM

MHGGTGFAGIDSSSPEVKGYWASLDASTQTTHELTIPNNLIGCIIGRQGA

NINEIRQMSGAQIKIANPVEGSSGRQVTITGSAASISLAQYLINARLSSE

KGMGCS

SEQ ID NO:6 (poly(rC)/poly(U)-rich-5'UTR RNA cis element) 5'-CUCCCGCCCGCUCCCGCUCGCUCCC-3'

Methods for testing the ability of an engineered hnRNP-E1 variant polypeptide to bind to an RNA comprising the sequence of SEQ ID NO:6 are known in the art. Such methods include, but are not limited to, RNA electrophoretic mobility shift assays, as exemplified herein, RNA pull-down assays, and oligonucleotide-targeted RNase H protection assays. Such assays are conducted in the presence or absence of homocysteine to determine the RNA-binding dependence of any particular hnRNP-E1 polypeptide tested on the presence of homocysteine. In one embodiment, RNA-protein binding interactions are assayed using 0.1 micrograms of purified recombinant wild-type hnRNP-E1 protein or recombinant hnRNP-E1 protein and 0-12 nM radiolabeled mRNA cis-elements in a final volume of 750 microliters of pH 7.6 binding buffer, the binding buffer comprising 10 mM Hepes, 3 mM MgCl2, 40 mM KCl, and 5% glycerol, in either the absence or presence of increasing concentrations of L-homocysteine at 4° C. for 1 hour. Additional methods are outline in Tang et al. ("Incrimination of heterogeneous nuclear ribonucleoprotein E1 (hnRNP-E1) as a candidate sensor of physiological folate deficiency." J Biol Chem. 2011; 286(45):39100-39115), which is incorporated herein in its entirety.

Described herein are nucleic acids that encode any suitable polypeptide of the present invention. In some embodiments, the nucleic acid is a DNA molecule which encodes a polypeptide as described herein. In some embodiments, the nucleic acids is an mRNA molecule which encodes a polypeptide as described herein.

In some embodiments, the nucleic acid encoding any of the above-mentioned engineered hnRNP-E1-comprising polypeptides is provided in the form of an expression vector that can be used to express the polypeptide in a recombinant host cell. Examples of suitable promoters for driving expression of engineered hnRNP-E1 polypeptides described herein include, but are not limited to, retroviral LTR elements; constitutive promoters such as CMV, HSV1-TK, SV40, EF-1.alpha., .beta.-actin; PGK, and inducible promoters, such as those containing Tet-operator elements. In some cases, one or more of the nucleic acid expression vectors encodes, in addition to an engineered hnRNP-E1 polypeptide, a marker gene that facilitates identification or selection of cells that have been transfected or infected. Examples of marker genes include, but are not limited to, genes encoding fluorescent proteins, e.g., EGFP, DS-Red, YFP, and CFP; genes encoding proteins conferring resistance to a selection agent, e.g., the neo$^R$ gene, and the blasticidin resistance gene. Nucleic acid vector transfection (e.g., transient transfection) methods may be used to introduce nucleic acid (e.g., plasmid) expression vectors into cells (e.g., mammalian cells). One of ordinary skill in the art appreciates, of course, that an expression vector can be selected based on the cellular hosts that will be used for expression. Accordingly prokaryotic expression vectors are selected for prokaryotic hosts such as E. coli, yeast expression vectors are selected for yeast, mammalian expression vectors suited for mammalian expression hosts, etc.

Methods for preparation of transfection-grade nucleic acid expression vectors and transfection methods are well established. See, e.g., Sambrook and Russell (2001), "Molecular Cloning: A Laboratory Manual," 3$^{rd}$ ed, (CSHL Press); and Current Protocols in Molecular Biology, John Wiley & Sons, N.Y. (2005), 9.1-9.14. Examples of high efficiency transfection efficiency methods include "nucleofection," as described in, e.g., Trompeter (2003), J Immunol. Methods, 274(1-2):245-256, and in international patent application publications WO2002086134, WO200200871, and WO2002086129, transfection with lipid-based transfection reagents such as FUGENE™ 6 and FUGENE® HD(Roche), XtremeGENE HD (Roche), DOTAP, and Lipofectamine™ LTX in combination with the PLUS™ (Invitrogen, Carlsbad, Calif.), DREAMFECT™ (OZ Biosciences, Marseille, France), GENEJUICE™ (Novagen, Madison, Wis.), polyethylenimine (see, e.g., Lungwitz et al., (2005), Eur. J Pharm. Biopharm., 60(2):247-266), GENE-JAMMER™ (Stratagene, La Jolla, Calif.), and nanoparticle transfection reagents as described in, e.g., U.S. patent application Ser. No. 11/195,066.

In some embodiments, provided herein is a recombinant virus comprising one of the above-mentioned nucleic acids encoding an engineered hnRNP-E1 variant polypeptide of the present invention. Examples of recombinant viruses include, but are not limited to, retroviruses (including lentiviruses); adenoviruses; and adeno-associated viruses. Often, the recombinant retrovirus is murine moloney leukemia virus (MMLV), but other recombinant retroviruses may also be used, e.g., Avian Leukosis Virus, Bovine Leukemia Virus, Murine Leukemia Virus (MLV), Mink-Cell focus-Inducing Virus, Murine Sarcoma Virus, Reticuloendotheliosis virus, Gibbon Ape Leukemia Virus, Mason Pfizer Monkey Virus, and Rous Sarcoma Virus, see, e.g., U.S. Pat. No. 6,333,195.

Also provided herein are genetically modified cells comprising any of the isolated nucleic acids described above. In some embodiments, the cells express the polypeptide encoded by the nucleic acid (e.g., a synthetic mRNA or an expression vector). In some embodiments, the genetically modified host cells are prokaryotic/bacterial cells such as *E. coli*. In other embodiments, the genetically modified host cells are eukaryotic cells, e.g., a mammalian cell line, mammalian primary cells (e.g., human primary cells), or yeast.

In some embodiments, the nucleic acid encoding an engineered hnRNP-E1 variant polypeptide is a synthetic mRNA generated in vitro. In some embodiments, the synthetic mRNA encoding the above-described polypeptides include one or more of an anti-reverse cap analog (ARCA), modified nucleotides (5-Methylcytidine-5'-Triphosphate and Pseudouridine-5'-Triphosphate), and a poly-A tail to enhance stability of the synthetic mRNA upon transfection and to reduce the immune response of transfected host cells. Methods for in vitro synthesis using DNA-dependent RNA polymerases (e.g., T7 or SP6 RNA polymerase) are well known in the art, and in vitro mRNA synthesis kits are commercially available as provided in, e.g., the MRNA EXPRESS™ kit (System Biosciences (Mountain View, Calif.). Efficient methods for synthesizing and transfecting synthetic mRNA in vitro and in vivo are described in, e.g., Mandal et al (2013), *Nat Protoc*, 8(3):568-582; and PCT Publication Nos: WO/2012/019168; WO/2012/045075; WO/2012/135805; WO/2012/158736; WO/2013/039861; WO/2013/039857; and WO/2013/052523.

Also provided herein is a purified polypeptide encoded by any of the nucleic acids described herein. In some embodiments, the purified polypeptide is a fusion polypeptide further comprising, in addition to an engineered hnRNP-E1 variant polypeptide amino acid sequence, a protein transduction domain (PTD). As used herein "protein transduction domain" refers to a structured polypeptide domain which facilitates intracellular delivery of the fusion polypeptide. Generation of PTD fusion proteins and methods for their use are established in the art as described in, e.g., U.S. Pat. Nos. 5,674,980, 5,652,122, and 6,881,825. See also, Becker-Hapak et al., (2003), Curr Protocols in Cell Biol, John Wiley & Sons, Inc. Exemplary PTD domain amino acid sequences include, but are not limited to, any of the following: YGRKKRRQRRR (SEQ ID NO:7); RKKRRQRR (SEQ ID NO:8); YARAAARQARA (SEQ ID NO:9); THRLPRRRRRR (SEQ ID NO:10); and GGRRARRRRRR (SEQ ID NO:11). In some embodiments, the PTD is linked to the N-terminus of an engineered hnRNP-E1 polypeptide. In other embodiments, the PTD is linked to the C-terminus of an engineered hnRNP-E1 polypeptide.

In some embodiments, a purified polypeptide is obtained by in vitro transcription and translation of a synthetic mRNA encoding an engineered hnRNP-E1 polypeptide or fusion polypeptide as described herein. In vitro systems for transcription of mRNA's encoding polypeptides of interest and their in vitro translation are well known in the art and are commercially available, e.g., from Ambion and Life Technologies. Alternatively, the purified polypeptide may be purified from cells genetically modified to express the polypeptide.

Also provided herein are pharmaceutical compositions comprising at least a pharmaceutically acceptable excipient and (i) a purified polypeptide comprising the amino acid sequence of an engineered hnRNP-E1; or (ii) a nucleic acid (e.g., a synthetic mRNA) encoding the amino acid sequence of a polypeptide comprising the amino acid sequence of an engineered hnRNP-E1. A thorough discussion of pharmaceutically acceptable carriers/excipients can be found in Remington's Pharmaceutical Sciences, Gennaro, A R, ed., 20th edition, 2000: Williams and Wilkins PA, USA. Pharmaceutical compositions of the invention include compositions suitable for administration via any peripheral route, including topical, intravenous, subcutaneous, intramuscular, intraperitoneal injection; oral, rectal, transbuccal, pulmonary, intranasal, or any other suitable route of peripheral administration. Pharmaceutically acceptable excipients particularly suitable for in vivo transfection of synthetic mRNA therapeutics are described in, e.g., PCT Publication Nos: WO/2012/019168; WO/2012/045075; WO/2012/135805; WO/2012/158736; WO/2013/039861; WO/2013/039857; and WO/2013/052523.

In some embodiments, the pharmaceutical compositions provided herein are suitable for injection, e.g., as a pharmaceutical composition for intravenous, subcutaneous, intramuscular, or for topical application as an ointment formulation. Aqueous compositions of the present invention comprise an effective amount of a composition of the present invention, which may be dissolved or dispersed in a pharmaceutically acceptable carrier or aqueous medium. The phrases "pharmaceutically or pharmacologically acceptable" refer to molecular entities and compositions that do not produce an adverse, allergic or other untoward reaction when administered to an animal, e.g., a human, as appropriate. As used herein, "pharmaceutically acceptable carrier" includes any and all solvents, nucleic acid or polypeptide transfection/transduction reagents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Exemplary pharmaceutically acceptable carriers for injectable compositions can include salts, for example, mineral acid salts such as hydrochlorides, hydrobromides, phosphates, sulfates, and the like; and the salts of organic acids such as acetates, propionates, malonates, benzoates, and the like. For example, compositions of the invention may be provided in liquid form, and formulated in saline based aqueous solution of varying pH (5-8), with or without detergents such polysorbate-80 at 0.01-1%, or carbohydrate additives, such mannitol, sorbitol, or trehalose. Commonly used buffers include histidine, acetate, phosphate, or citrate. Under ordinary conditions of storage and use, these preparations can contain a preservative to prevent the growth of microorganisms. The prevention of the action of microorganisms can be brought about by various antibacterial and antifungal agents, for example, parabens, chlorobutanol; phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate, and gelatin.

For human administration, preparations meet sterility, pyrogenicity, general safety, and purity standards as required by FDA and other regulatory agency standards. The active compounds will generally be formulated for parenteral administration, e.g., formulated for injection via the intravenous, intramuscular, subcutaneous, intralesional, or intraperitoneal routes. The preparation of an aqueous composition that contains an active component or ingredient will be known to those of skill in the art in light of the present disclosure. Typically, such compositions can be prepared as injectables, either as liquid solutions or suspensions; solid forms suitable for use in preparing solutions or suspensions upon the addition of a liquid prior to injection can also be prepared; and the preparations can also be emulsified.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, methods of preparation include vacuum-drying and freeze-drying techniques which yield a powder of the active ingredient plus any additional desired ingredient from a previously sterile-filtered solution thereof.

Methods

In some embodiments provided herein is a method for increasing translation of a target mRNA in a mammalian cell, the method comprising providing, in the mammalian cell, one of the engineered hnRNP-E1 polypeptides described herein, e.g., a polypeptide comprising an amino acid sequence at least 90% identical to any of SEQ ID NOs:2-5, wherein the encoded polypeptide comprises a substitution at a position selected from the group consisting of C293, C54, C158, or C201 relative to SEQ ID NO:1 and binds a single-stranded RNA comprising SEQ ID NO:6 independent of homocysteine, wherein the target mRNA comprises a poly(rC)- and poly(U)-rich 5'-UTR, thereby increasing translation of the target mRNA in the mammalian cell. In some embodiments, the polypeptide is administered to the cell as a purified polypeptide. In some embodiments, the polypeptide is expressed by the cell. In some embodiments, the mammalian cell is a human cell (e.g., a primary cell or a cell line). In other embodiments, the cell is a non-human mammalian cell. In some cases the mammalian cells are cells cultured ex vivo in a monolayer or organotypic format. In other embodiments, the method is directed to altering translation of target mRNAs in vivo.

In some embodiments, expression of the engineered hnRNP-E1 polypeptide is induced by delivering a nucleic acid expression vector (e.g., a plasmid) encoding the polypeptide. In other embodiments, expression is achieved by delivering an mRNA, e.g., a synthetic mRNA encoding the engineered hnRNP-E1 polypeptide as described herein.

In some embodiments, the target mRNAs, the translation of which can be increased by the above-mentioned method, include folate receptor mRNA, (endogenous) hnRNP-E1 mRNA, collagen alpha (I) mRNA, human herpesvirus 8 mRNA, erythropoietin mRNA, human alpha-globin mRNA, human beta-globin mRNA, μ-opioid receptor mRNA, androgen receptor mRNA, p21$^{waf}$ mRNA, tyrosine hydroxylase mRNA, neurofilament M mRNA, or a combination thereof. In some embodiments, the mRNAs the translation of which is upregulated include a collagen alpha (I) mRNA. In other embodiments, the target mRNA (such as human papillomavirus type 16 mRNA (in either L2 mRNA or 57-nucleotide poly(U)-rich cis-element in the early polyadenylation element (upstream of L2L1 genes)) can be destroyed upon binding by engineered hnRNP-E1.

Also provided herein is a method for treating a health condition by administering a therapeutically effective amount of a pharmaceutical composition to a subject in need thereof, the pharmaceutical composition containing one of the nucleic acids encoding an engineered hnRNP-E1, as described herein; or (ii) a polypeptide comprising the amino acid sequence of an engineered hnRNP-E1 as described herein. In some embodiments of the treatment method, the pharmaceutical composition to be administered contains a nucleic acid encoding a polypeptide comprising any of SEQ ID NOs:2-5. In other embodiments of the method, the pharmaceutical composition to be administered contains a polypeptide comprising any of SEQ ID NOs:2-5. In other embodiments, the pharmaceutical composition contains a nucleic acid encoding a polypeptide consisting of any of SEQ ID NOs:2-5, or a polypeptide consisting of any of SEQ ID NOs:2-5.

In some embodiments, the subject to be treated is suffering from a condition selected from the group consisting of: human papillomavirus infection, Kaposi's sarcoma, anemia, a skin condition, alpha-thalassemia, beta thalassemia, chronic pain, androgen deficiency, a tumor, Parkinson's disease, and a nerve injury.

In some embodiments, the condition to be treated is a skin condition. In one embodiment, the condition to be treated is a wound. In some embodiments, the pharmaceutical composition to be administered is administered by a topical route.

In the described treatment methods, pharmaceutical compositions described herein are administered in a manner compatible with the dosage formulation and in such amount as is therapeutically effective. The formulations are easily administered in a variety of dosage forms, such as injectable solutions suitable for in vivo delivery of nucleic acids as described above, or, alternatively, as ointments to be applied topically.

The term "unit dose" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the subject to be treated, the state of the subject and the protection desired. The person responsible for administration will, in any event, determine the appropriate dose for the individual subject.

The invention will be more fully understood upon consideration of the following non-limiting Examples.

EXAMPLES

Example 1—Generation of Molecular Mimics of Homocysteinylated-hnRNP-E1 by Mutagenesis of Cysteines Experimental Procedures Materials—

All reagents of the highest available purity were purchased from Sigma-Aldrich (St. Louis, Mo.). All cell culture media and other additives, Dulbecco's phosphate-buffered saline (D-PBS), *Escherichia coli* DH10B-competent bacteria, and oligonucleotides were from Invitrogen (Carlsbad, Calif.). [α-$^{32}$P]UTP (specific activity >3000 Ci/mmol) and L-[$^{35}$S]methionine or L-[$^{35}$S]cysteine (in vitro translation grade) were from Perkin-Elmer (Waltham, Mass.). Restriction endonucleases were from Roche Applied Science (Indianapolis, Ind.). L-homocysteine (98% purity) was from Sigma-Aldrich.

Culture of Placental Cell Lines—

The human placental cell lines (1584, JAR and CCL-98) obtained from American Type Culture Collection (Manassas, Va.), were propagated long-term in high-folate media (DMEM-HF), which contained non-dialyzed 10% fetal bovine serum, and 9.1 µM folic acid plus 13.6 nM 5-methyltetrahydrofolate. These cells were then slowly adapted to growth in physiologically low-folate media (DMEM-LF), which contained no added folic acid to the media, non-dialyzed 10% fetal bovine serum and 13.6 nM 5-methyltetrahydrofolate, for 14 weeks following which both mRNA and protein for folate receptor and hnRNP-E1 were evaluated. Folate receptor-α and hnRNP-E1 RNA from high-folate and low-folate placental cells was determined by quantitative real-time RT-PCR (qRT-PCR).

Preparation of 25-Nt hnRNP-E1 mRNA Cis-Element and Related Constructs—

To prepare 25-nt hnRNP-E1 mRNA cis-element, pSPT18-25 DNA was obtained by subcloning a pair of oligodeoxynucleotides (5'-g CTC CCG CCC GCT CCC GCT CGC TCC C g-3' SEQ ID NO:12 and 5'-aattc GGG AGC GAG CGG GAG CGG GCG GGA Gctgct-3' SEQ ID NO:13) into pSPT18 vector linearized with Pst1 and EcoRI. To prepare 25-nt hnRNP-E1 mRNA cis-element proximal to hnRNP-E1 mRNA, pSPT18-25-hnRNP-E1 DNA was obtained by subcloning the PCR product from Gene Pool™ cDNA (Human Placenta cDNAs, Invitrogen) into pSPT18. The PCR product from Gene Pool™ cDNA was digested with Pst1 and EcoRI, and then ligated to pSPT18 plasmid linearized with Pst1 and EcoRI. The primers used in PCR were: 5'-tgacctgcag GAC TCC CGC CCG CTC-3' (SEQ ID NO:14) and 5'-tgacgaattc CTA GCT GCA GGG CAT GC-3'(SEQ ID NO:15).

To incorporate 25-nt hnRNP-E1 cis-element proximal to a chloramphenicol acetyltransferase (CAT) reporter (pCAT-25) and a control 25-nt scrambled sequence proximal to CAT (pCAT-25-scrambled), two pairs of oligodeoxynucleotides were subcloned into pCAT3-Control Vector that was linearized with Nhe1 and BglII to generate pCAT-25 and pCAT-25-scrambled vectors. Oligodeoxynucleotides for 25-nt hnRNP-E1 cis-element inserts were: 5'-ctagc CTC CCG CCC GCT CCC GCT CGC TCC C a-3' (SEQ ID NO:16) and 5'-gatct GGG AGC GAG CGG GAG CGG GCG GGA G g-3'(SEQ ID NO:17). Oligodeoxynucleotides for the 25-nt scrambled insert sequence were: 5'-ctagc GCG TCG CTC GCT TCG CAC GTG CGC C a-3'(SEQ ID NO:18) and 5'-gatct GGC GCA CGT GCG AAG CGA GCG ACG C g-3' (SEQ ID NO:19).

RNA Protein Binding Assays—

RNA-protein binding assays involved incubation of one of various radiolabeled target RNAs (1×10$^5$ cpm of [$^{35}$S] 25-nt hnRNP-E1 mRNA cis-element, or 18-nt folate receptor-α mRNA cis-element, or Human Papillomavirus-type 16 (HPV16) L2 RNA cis-element) with either purified 0.5 µg dialyzed purified recombinant glutathione S-transferase (GST)-hnRNP-E1 or its mutants in standard buffer in the absence or presence of various concentrations of physiological and non-physiologically relevant thiols [ß-mercaptoethanol (ß-ME), glutathione, methionine, L-cysteine, L-homocysteine, and dithiothreitol (DTT)]. Parenthetically, there was no significant difference in RNA binding to GST-hnRNP-E1 by use of either 32P-RNA probes or 35S-labeled RNA probes used. Other studies assessed the effect of iron(II) or iron(III) on homocysteine-induced RNA-protein interactions.

In Vitro Transcription/Translation Studies—

In vitro transcription-translation was carried out using the Linked SP6/T7 In Vitro Transcription/Translation Kit (Roche Applied Science) after addition of one of various targeted DNAs—pSPT18-25-hnRNP-E1 DNA, or Pst1-linearized plasmid pSPT18-folate receptor-α, or HPV16 L2 DNA, (0.5 µg/reaction)—to the transcription mix as described. In other experiments, the capacity for perturbing the interaction of hnRNP-E1 with the 25-nt hnRNP-E1 cis-element during in vitro translation was assessed in the presence of either scrambled oligonucleotides (5'-GCG TCG CTC GCT TCG CAC GTG CGC C-3' SEQ ID NO:20) or specific antisense oligonucleotides (5'-GGG AGC GAG CGG GCG GGA G-3' SEQ ID NO:21) generated against the 25-nt hnRNP-E1 mRNA cis-element (GenScript USA, Piscataway, N.J.).

Dissociation Constant ($K_D$) of Various RNA-Protein Interactions—

The influence of either L-homocysteine or L-cysteine on the dissociation constant ($K_D$) of the RNA-protein interaction was assessed in the absence and presence of physiological concentrations of glutathione (10 mM) using previously described methods. Specific binding was determined by subtracting values of non-specific binding with GST from those of total binding with GST-hnRNP-E1; (however, in Table 1 and FIG. 6G, non-specific binding using bovine serum albumin (BSA) was subtracted from total binding to GST-hnRNP-E1 to determine specific binding). The $K_D$ was calculated from a Scatchard plot using GraphPad Prism 6 from GraphPad Software (San Diego, Calif.), as previously described in the art.

Effects of L-Homocysteine on Various CAT Reporter Constructs Transfected into Placental 1584-HF Cells—

To prepare pCAT-25 or pCAT-25-Mutant two pairs of oligonucleotides, one for pCAT-25, (5'-tagcaggtac AAG CTT CTC CCG CCC GCT CCC GCT CGC TCC CCA TGG tgtaactagct-3'SEQ ID NO:22; 5'-agctagttaca CCA TGG GGA GCG AGC GGG AGC GGG CGG GAG AAG CTT gtacctgcta-3' SEQ ID NO:23), and one for pCAT-25-Mutant#6, (5'-tagcaggtac AAG CTT CTT CCG CCC GCT CCC GCT CGC TTC CCA TGG tgtaactagct-3' SEQ ID NO:24; 5'-agctagttaca CCA TGG GGA GCG AGC GGG AGC GGG CGG GAG AAG CTT gtacctgcta-3'SEQ ID NO:25) were first linearized with HindIII and NcoI and subcloned into pCAT3 Control DNA digested with HindIII and NcoI. Following transient transfection of either pCAT-25 or pCAT-25-Mutant#6 plasmid DNA together with pSV-ß-gal DNA into placental 1584-HF cells, these cells were incubated with physiologically relevant concentrations of L-homocysteine and net CAT expression was assessed, as previously described.

Determination of the Biosynthetic Rate of Folate Receptors or hnRNP-E1 Proteins in Cells Transfected with Either Wild-Type- or Various Mutant-hnRNP-E1 Proteins—

Transfection of purified recombinant wild-type or various mutant hnRNP-E1 proteins into cells was achieved using the Xfect™ Protein Transfection Kit (Clontech, Mountain View, Calif.). Briefly, placental 1584-HF cells in 10-cm dishes at 70-80% confluence were transfected with 2.4-mL serum-free medium and Xfect Protein Transfection Reagent (1.2-mL) containing 20-µg of either wild-type hnRNP-E1-, or highest-affinity (HA)-hnRNP-E1(C293S)-mutant, or wild-type-like hnRNP-E1 (G292A)-mutant proteins and 2-µg of ß-galactosidase at 37° C. for 60-min. After cysteine-starvation for 4-h, an aliquot of cells were assessed for ß-galactosidase activity (to measure the efficiency of co-transfection of ß-galactosidase) and the remaining cells were pulsed with L-[$^{35}$S]cysteine (250-µCi) and assessed for specific [$^{35}$S]

cysteine incorporated into folate receptor to determine the biosynthetic rate of this protein. A similar protocol was employed for analysis of newly synthesized [$^{35}$S]hnRNP-E1 using anti-hnRNP-E1 antiserum-coupled agarose and control agarose in order to derive values for specific [$^{35}$S] cysteine incorporated into hnRNP-E1 and thereby determine the biosynthetic rate of this protein.

Effects of Iron(II) on the Homocysteine-Induced RNA-Protein Interaction—

Studies were conducted to evaluate the effect of iron(II) (as ferrous sulfate heptahydrate) or iron(III) (as ferric chloride hexahydrate) in modulating RNA-protein interactions during gel-shift assays in either the absence or presence of 10-mM glutathione. The iron preparation, either alone or with 50-µM of deferoxamine (DFO) to define the specificity of iron(II), was incubated first with glutathione and hnRNP-E1 before addition of other components of the reaction mixture. Briefly, RNA-protein binding and gel-shift assays were carried out with purified recombinant GST-hnRNP-E1 protein and [$^{35}$S]25-nt hnRNP-E1 mRNA cis-element in binding buffer and 5-µM L-homocysteine plus increasing concentrations of iron(II) or iron(III) (0-25-µM). The samples were analyzed by PAGE and autoradiography overnight followed by densitometric analysis of the signals representing RNA-protein complexes.

Expression of the GST Fusion Protein from GST-hnRNP-E1 and its Mutants—

Recombinant GST-plasmid DNA, pGST-hnRNP-E1, pGST-hnRNP-E2, and related engineered variant plasmids were transformed into BL21 *Escherichia coli* from Novagen (Madison, Wis.). After induction by 1 mM isopropyl-1-thio-ß-D-galactopyranoside, the GST-hnRNP-E1 and engineered variant fusion proteins were individually purified using the B-PER GST Fusion Protein Purification Kit (Pierce, Rockford, Ill.). The eluted GST fusion proteins were dialyzed against 500 volumes of buffer to remove excess reducing reagents (such as dithiothreitol (DTT)) and assayed by SDS-PAGE and Western blots using anti-peptide hnRNP-E1 antiserum. Gel shift assays with target RNA were carried out as described.

Site-Directed Mutagenesis of hnRNP-E1—

Figures 10A, 10B, 10C, 10D, 10E, 10F, 10G, 10H:
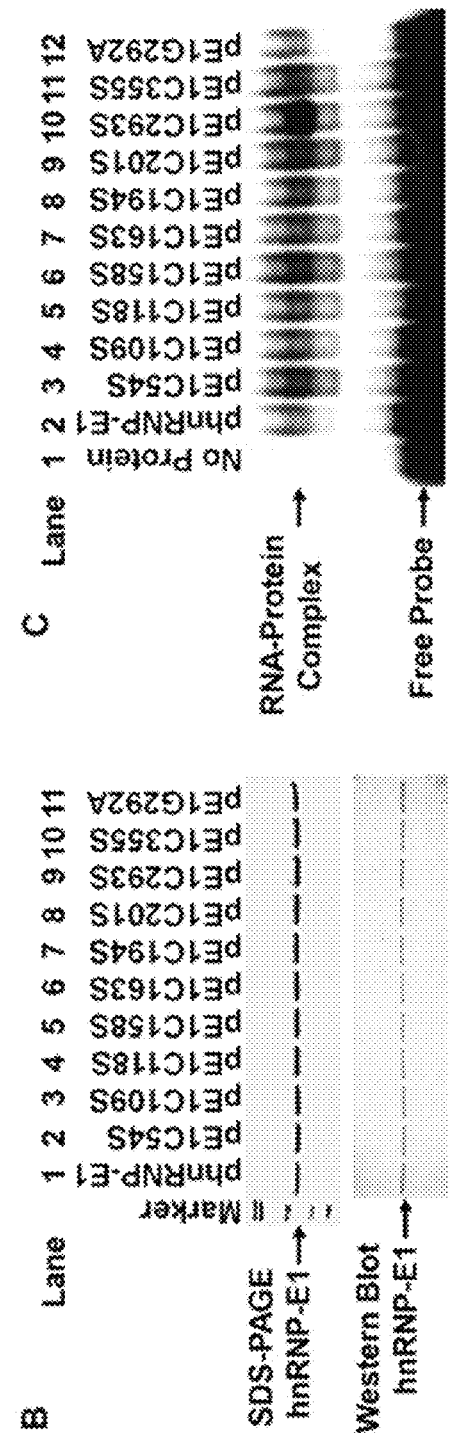
FIGS. 10A-10H show the amino acid sequence of hnRNP-E1 and location of mutated residues (A); evaluation of purified recombinant wild-type or mutant GST-hnRNP-E1 by SDS-PAGE and Western blots (B), their interaction with either folate receptor-α mRNA cis-element (C, D, E, F) or HPV16 L2 mRNA (G, H) on gel-shift assays (C, G), by in vitro translation (D, E, H), and effects on CAT activity after transfection into HeLa-IU$_1$-HF cells (F). In Panels B-G, each mutant protein is identified by the notation pE1, which precedes the listing of a specific mutation. The data are presented as the mean±SD. The symbol # signifies the 100% value. Labeled means without a common letter differ, P<0.05. BSA, Bovine serum albumin; CAT, chloramphenicol acetyltransferase; DTT, Dithiothreitol; NEM, N-ethyl-maleimide; FR, folate receptor; L2 RNA, Human Papillomavirus type 16 L2 RNA; GST, glutathione S-transferase; hnRNP-E1, wild-type hnRNP-E1; hnRNP-E1(G292A), wild-type-like hnRNP-E1(G292A)-mutant; hnRNP-E1 (C293 S), highest affinity (HA)-hnRNP-E1(C293S)-mutant; pE1, plasmid hnRNP-E1.
Figures 10A, 10B, 10C, 10D, 10E, 10F, 10G, 10H:
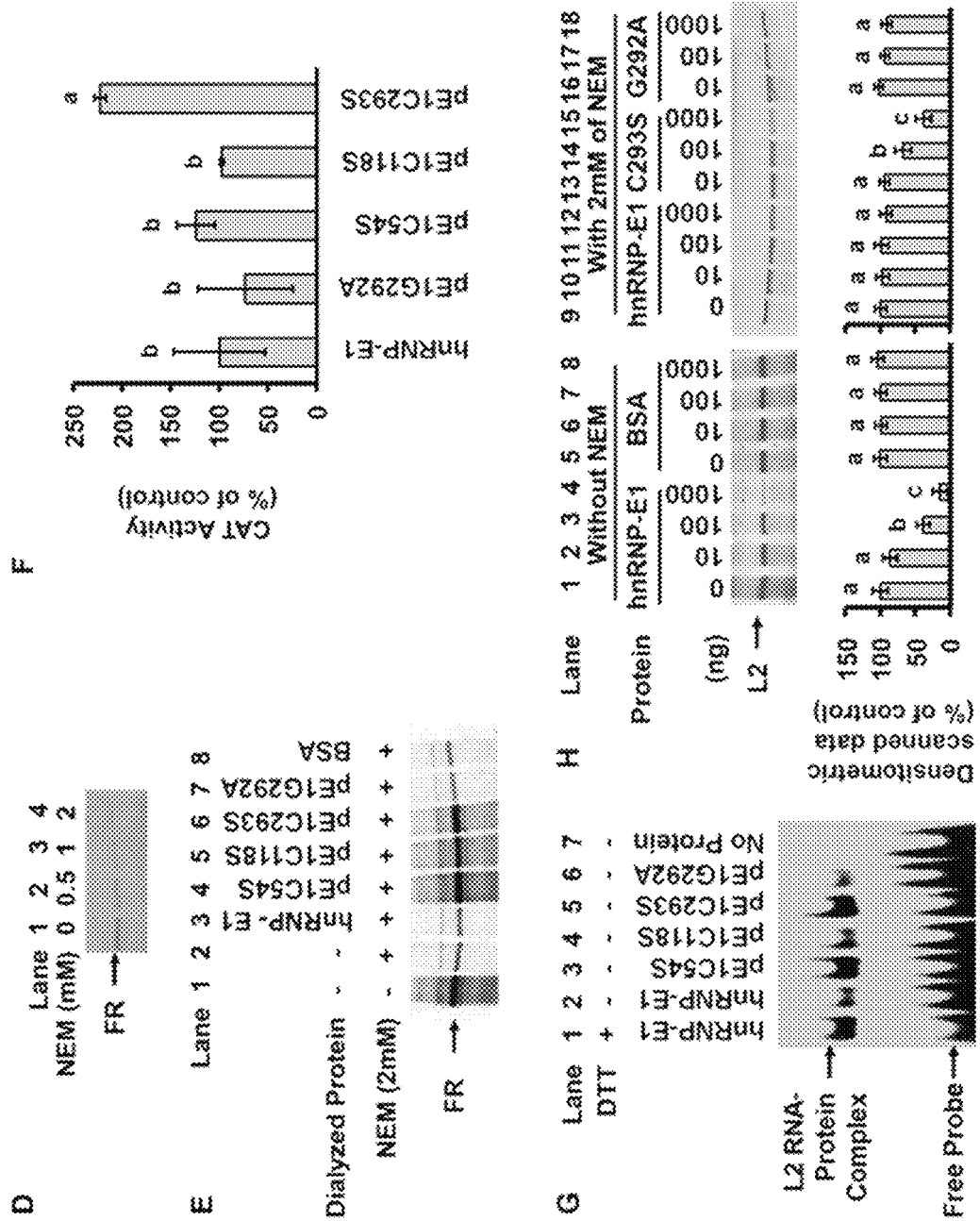

K-homology (KH) domains in hnRNPs are primarily responsible for the mRNA-binding exhibited by these proteins (3, 4). Because more than one homocysteine-S-S-cysteine-protein mixed disulfide bonds involving KH domains were formed when homocysteine bound to hnRNP-E1 and unmasked an underlying mRNA-binding site, we used site-directed mutagenesis to generate single amino acid substitutions of cysteine residues (to serine) in hnRNP-E1 (FIG. 10A). As controls, Gly-52 or Gly-292 were mutated to alanine (FIG. 10A). The primers for these mutants are shown in Table 10. The plasmids pE1C54S, pE1C94S, pE1C109S, pE1C118S, pE1C158S, pE1C163S, pE1C201S, pE1C293S, pE1C359S, pE1G52A and pE1G292A were generated from plasmid-pGEX-4T-1-E1 (phnRNP-E1) using a Quick-Change® Site-Directed Mutagenesis Kit from Stratagene (La Jolla, Calif.). All newly constructed plasmids containing only the desired mutation were purified using the High Pure Plasmid Isolation Kit (Roche Applied Science) and verified by sequencing in the core sequencing facility of Indiana University School of Medicine.

Human Papillomavirus-16 (HPV16) L2 RNA-Related Gel-Shift and In Vitro Translation—

Construction of plasmids for generation of HPV16 L2 RNA, gel-shift and in vitro translation studies were carried as described with additional treatments shown in FIGS. 10A-10D.

Quantitative Real-Time RT-PCR (qRT-PCR) to Determine RNA Expression of hnRNP-E1 and Folate Receptor-α in Cells—

Total RNA was separately extracted from placental 1584-HF and 1584-LF cells. Gene expression was determined on triplicate RNA samples (50 ng per reaction) using an Invitrogen SuperScript III Platinum One-Step qRT-PCR kit and an ABI 7900HT Sequence Detection System (PE Biosystems, Foster City, Calif.). The cycle conditions were as follows: after a first step of 15 min at 50° C. and 10 min at 95° C., the samples were cycled 40 times at 95° C. for 15 seconds and at 60° C. for 60 seconds. For all quantitative analyses, we used the comparative CT method by following the PE Biosystems protocol. The specific primers were obtained from Invitrogen with fluorogenic labels (either FAM or JOE). Primers for hnRNP-E1 were 5'-GAC GCC GGA GAC TGG GAG AGC G [FAM] C-3' (SEQ ID NO:26) and 5'-GGA TAT GCT GCC CAA CTC CA-3' (SEQ ID NO:27). Primers for folate receptor-α were 5'-GAA CCT ATG AGG AGG TGG CGA GG [FAM] TC-3' (SEQ ID NO:28) and 5'-TAG GGC CAG GCT AAG CAG GA-3' (SEQ ID NO:29). Primers for GAPDH were 5'-CAA CAG GAG GAG TGG GTG TCG CTG (JOE) TG-3' (SEQ ID NO:30) and 5'-GGC ATC CTG GGC TAC ACT GA-3' (SEQ ID NO:31). Primers to the hnRNP-E1 gene or folate receptor-α gene (labeled with FAM) and primers to a housekeeping gene GAPDH (glyceraldehyde-3-phosphate dehydrogenase, labeled with JOE) were run in parallel, respectively, to standardize the input amount. Controls consisting of RNase free water were negative in all runs.

Determination of the Concentration of Homocysteine, Cystathionine, Cysteine, and Methionine in Placental Cells—

Briefly, 4 flasks of placental 1584 cells that were stably propagated long term in MEM-HF—hereafter referred to as 1584-HF cells, and 4 flasks of 1584-LF cells that were stably propagated beyond 14 weeks in MEM-LF—hereafter referred to as 1584-LF cells, were cultured for 48 h to achieve 80% confluence, following which the spent medium from each was saved. Then 0.6-mL of D-PBS was added to each flask and cells were released using a scraper. The cells from 4 flasks each of 1584-HF and 1584-LF were then separately combined in 4-mL MEM-HF and MEM-LF media, respectively, and then pelleted by centrifugation. The supernatant 'cell wash medium'—which contained thiols that may have leaked out of 1584-HF and 1584-LF cells—was collected. After 1584-HF and 1584-LF cell-pellets were weighed, each 'cell wash medium' was added back to its respective pellet. These samples then underwent 5 freeze-thaw cycles before passage through a 0.22 µm filter and the volume of each of these samples was measured. The samples from cells and their respective spent media were measured for the concentration of homocysteine, cystathionine, cysteine, and methionine by stable isotope dilution gas chromatography-mass spectrometry. The scientist who carried out this analysis was blinded to sample identity in these experiments by the use of coded samples. Because the homocysteine in the spent medium leaked out from cells, the amount of homocysteine measured in 1584-HF and 1584-LF spent media (minus that present in basal MEM-HF/LF media) was added back to assess the net concentration of homocysteine in cells; this was further adjusted by cell weight and volume.

Capture of RNA-Protein Complexes within Cells—

Slot-blot hybridization was carried out under high stringency conditions to detect intracellular RNA-protein complexes (composed of endogenous hnRNP-E1 RNA cis-element-bound to cellular hnRNP-E1 proteins) in placental 1584 cells under experimental conditions that modulated the intracellular concentration of homocysteine. We employed similar principles used to capture folate receptor-α mRNA cis-element-bound hnRNP-E1 complexes in HeLa-IU1 cells. Briefly, following L-homocysteine treatment, the extant intracellular RNA-protein complexes were UV-cross-linked and isolated on anti-hnRNP-E1 antiserum-linked agarose. Following RNase treatment and proteolysis, equal aliquots of the released small mRNA cis-element fragments were probed for evidence of enrichment of hnRNP-E1 mRNA cis-element in experimental cells using a specific [$^{35}$S]labeled antisense hnRNP-E1 mRNA cis-element probe.

Transfection of Various Chloramphenicol Acetyltransferase (CAT) Reporters into Hela-IU1-HF Cells with hnRNP-E1 DNA or its Mutants—

A plasmid containing CAT reporter DNA driven by an 18-nucleotide folate receptor-α mRNA cis-element, was constructed as previously described. Briefly, HeLa-IU1-HF cells were grown to 70-80% confluence and then co-transfected with CAT reporter DNA driven by an 18-nucleotide folate receptor-α mRNA cis-element and various construct combinations of either wild-type and mutant hnRNP-E1 plasmids using X-tremeGENE DNA transfection reagent (Roche Applied Science). The transfection reactions were set up with 6-µg DNA and 12-µL XtremeGENE DNA transfection reagent for each well. In these transfection experiments, pSV-ß-gal was used as an internal control to monitor the efficiency of transfection of cells. After 48 h cells were harvested for protein determination using the BCA protein assay (Pierce); ß-galactosidase activity by the ß-galactosidase chemiluminescent assay (Roche Diagnostics); and CAT activity using a CAT ELISA kit (Roche Diagnostics). All experiments were carried out 4 times with 3 replications per treatment. The data from non-transfected cells was used as a background and subtracted from that obtained with transfected cells. All data were normalized using the internal standard and protein concentration for each treatment.

Transfection of Antisense Oligonucleotides to the 25-Nt hnRNP-E1 Cis-Element on the Biosynthetic Rate of hnRNP-E1 Proteins in Cells—

On the day before transfection, placental 1584-HF cells were trypsinized, counted, and plated in 6-well plates at $2\times10^5$ cells per well in 2.5-mL of MEM-HF medium, so that cells would be 70-80% confluent after overnight culture. Cells were then transfected with either wild-type, or scrambled DNA, or antisense DNA to 25-nt hnRNP-E1 cis-element using Lipofectamine 2000 DNA transfection reagent and the manufacturer's protocol. One well of cells was trypsinized and harvested on day-3 (2 days after transfection) as a control. Cells in the remaining 5 wells were starved of cysteine using cysteine-free MEM-HF for 4-h following which the rate of biosynthesis of hnRNP-E1 protein was determined in transfected cells by specifically immunoprecipitating and quantifying newly synthesized [$^{35}$S]hnRNP-E1.

RNA Interference of hnRNP-E1 mRNA on the Biosynthetic Rate of hnRNP-E1 and Folate Receptor Proteins in Cells—

Before the day of siRNA transfection, placental 1584-HF cells were trypsinized, counted, and plated in 6-well plates at $1.4\times10^5$ cells per well (about 30-40% confluence) in 2.5-mL of MEM-HF medium, so that cells were 60-80% confluent after overnight culture. Cells were then transfected over 2-days with either 10 nM predesigned Stealth RNA (siRNA-hnRNP-E1/PCBP1) or 10-nM scrambled negative stealth RNAi control using Lipofectamine RNAiMAX transfection reagent and a minor modification of the manufacturer's protocol. One of these wells was trypsinized and harvested 2 days after transfection, following which RNA was purified for qRT-PCR analysis of hnRNP-E1 RNA expression. Cells in the remaining 5 wells were starved of cysteine for 4-h and the rate of biosynthesis of newly synthesized [$^{35}$S]hnRNP-E1 and [$^{35}$S]folate receptor proteins was determined, as previously described.

Animal Protocol and Animal Care—

All animal care procedures conformed to the "Guide for the Care and Use of Laboratory Animals." The protocols for the use of athymic mice in experiments involving tumor xenografts were approved by the Institutional Animal Care & Use Committee at Indiana University-Purdue University at Indianapolis. To evaluate for up-regulation of folate receptors and hnRNP-E1 within cervical cancer xenograft tumors that were generated in athymic mice, 6 athymic mice were fed a standard folate-replete diet (1200 nmol folate/kg-diet) and 5 athymic mice were fed a severe folate-restricted diet (120 nmol folate/kg-diet) for 4 weeks before injection of 1 million HeLa-IU1 cells into their flanks. The tumors were subsequently examined for hnRNP-E1 and folate receptor expression by immunohistochemistry, Northern blots, and Western blots. For Western blot analyses of folate receptor and hnRNP-E1 expression in tumors, 50 µg protein from HeLa-IU1-derived tumors were subjected to 10% SDS-PAGE and Western transfer followed by probing of nitrocellulose-bound proteins with either anti-folate receptor antiserum, or anti-hnRNP-E1 antiserum or anti-GAPDH antibodies. Total RNA was obtained from HeLa-IU1-derived tumors in mice fed a normal or low-folate diet. The hnRNP-E1 probe was excised from plasmid pGEX-4T-1-hnRNP-E1, using BamH1 and Not1 digestion. The folate receptor-α plasmid (pSPT 18-FR) was digested with HindIII and EcoRI to liberate its cloned insert. DNA fragments were gel-purified and labeled using a Random Primed Labeling Kit (Roche Applied Science) and [α-$^{32}$P]dATP. Northern blots were carried out by electrophoresis of 20 RNA in standard formaldehyde-agarose gels followed by transfer to Hybond-N+ nylon membranes (Amersham/GE Healthcare Biosciences, Pittsburgh, Pa.) and UV cross-linking. Membranes were hybridized with the $^{32}$P-labeled probes and detected according to the manufacturer's instructions (Roche Applied Science). Ethidium bromide staining of 28S was monitored for RNA quality and ß-actin was used as a loading control.

Animal experiments using CD-1 mice were conducted at the National Center for Toxicological Research (Jefferson, Ark.); these animal studies were approved by each of the local Institutional Animal Care and Use Committees in Arkansas and Indiana. The protocols for the procurement and feeding of CD-1 mice (Charles River, Wilmington, Mass.) with either a folate-replete diet (1200-nmol folate/kg diet) or folate-deficient diet (400-nmol folate/kg diet), breeding and dams were killed on gestation day 17, removal and euthanasia of fetuses and fixation in formalin, histochemical staining, and analysis of paraffin-embedded fetal tissues was as described. The placentae from dams that were fed a folate-deficient versus a folate-replete diet were also examined for morphological differences after sectioning and staining. Images were captured with a Leitz DMLB light microscope equipped with a Diagnostic Instruments Spot digital camera (Diagnostic Instruments, Sterling, Mich.) and processed using Adobe PhotoShop software (San Jose, Calif.). The localization of tissues in gestation day 17 fetuses was based on Kaufman's atlas.

Statistical Analyses—

All of the statistical analyses were conducted using GraphPad Prism 6 (GraphPad Software, San Diego, Calif.). Unless otherwise specified, results are expressed as means±SDs, n=3 (means of triplicates). Comparisons between 2 groups were analyzed by Student's t test and comparison between multiple groups were analyzed using one-way ANOVA followed by a Tukey's test. The statistical significance was set at P<0.05.

Results

Characterization of a 25-Nt Cis-Element in the 5'-UTR of hnRNP-E1 mRNA that Interacts with hnRNP-E1.

The gene sequence of hnRNP-E1 revealed a candidate 25-nt poly(rC)-rich region in the 5'-UTR of hnRNP-E1, from −145 to −120 upstream of the start site of the coding sequence of hnRNP-E1 (FIG. 1A). This candidate hnRNP-E1 cis-element had a similar structural organization to that noted within the 18-nt folate receptor-α mRNA cis-element, which consisted of a tandem CUCC sequence separated by 6-8 bases as a putative protein binding motif; likewise, hnRNP-E1 mRNA cis-element contained three such CUCC sequence motifs. Therefore, we focused on the potential for binding between homocysteinylated-hnRNP-E1 and this 25-nt cis-element in the 5'-UTR of hnRNP-E1 mRNA to determine if this RNA-protein interaction led to enhanced translation of hnRNP-E1 in vitro and in cultured placental cells.

Gel-shift assays showed a dose-dependent increase of RNA-protein signal with increasing physiologically relevant concentrations of L-homocysteine (FIG. 1B, lanes 6-10). The involvement of hnRNP-E1 in RNA-protein complexes was shown by a super-shift of the RNA-protein signal with anti-hnRNP-E1 antiserum (FIG. 1B, lane 1); no such super-shift was noted using nonimmune serum (not shown). Additional studies described herein confirmed the specificity of the anti-hnRNP-E1 antiserum used in these studies. The reticulocyte lysate mixture used for in vitro translation contains small quantities of hnRNP-E1. Accordingly, we evaluated the functional consequences of interaction of the 25-nt hnRNP-E1 mRNA cis-element and endogenous hnRNP-E1 during in vitro translation. Quenching excess ß-ME in the translation mixture with N-ethylmaleimide (FIG. 1C, lane 2-4) led to a progressive reduction in the amount of hnRNP-E1 translated when compared to the baseline hnRNP-E1 signal (FIG. 1C, lane 1). Maintaining N-ethylmaleimide in the reaction mixture improved sensitivity of the system to subsequent addition of physiological concentrations of L-homocysteine, which led to progressively increased translation of hnRNP-E1 (FIG. 1C, lanes 5-7). The specific involvement of endogenous hnRNP-E1 in mediating translation of hnRNP-E1 was confirmed by the dose-dependent quenching of signal with addition of increasing concentrations of anti-hnRNP-E1 antiserum (FIG. 1D, lanes 5-7); by contrast, there was no effect of anti-hnRNP-E1 antiserum on the translation of internal control DNA (lane 1 versus 2), and no reduction in translation of hnRNP-E1 by nonimmune serum (lane 9).

The experiments that led to selection of the most effective molecular mimic of homocysteinylated-hnRNP-E1 and its control that was used to further characterize the interaction of hnRNP-E1 with its own cis-element are described herein and in Table 10. FIGS. 10A-10H demonstrate that mutation of cysteine-293 to serine in the third K-homology (KH3) domain of hnRNP-E1 resulted in the highest affinity for the folate receptor-α mRNA cis-element and for HPV16 L2 cis-element, even in the absence of L-homocysteine, which also led to expected functional outcomes; this mutant is hereafter referred to as the highest-affinity (HA)-hnRNP-E1 (C293S)-mutant. By contrast, mutation of the adjacent glycine-292 to alanine failed to confer such properties, and this mutant protein behaved similar to wild-type hnRNP-E1 in that interaction with these target cis-elements were increased only upon addition of L-homocysteine; hence this control was referred to as a wild-type-like hnRNP-E1(G292A)-mutant. Thus, as also shown in FIG. 1B, incubation of 25-nt hnRNP-E1 RNA cis-element with wild-type hnRNP-E1 and wild-type-like hnRNP-E1(G292A)-mutant in the absence of L-homocysteine (lanes 3 and 4) revealed no RNA-protein gel-shift signals; but, there was a strong signal when 25-nt hnRNP-E1 mRNA cis-element reacted with (HA)-hnRNP-E1(C293S)-mutant (lane 5) even in the absence of L-homocysteine. And after neutralizing ß-ME by N-ethylmaleimide, only (HA)-hnRNP-E1(C293S)-mutant markedly stimulated translation of hnRNP-E1 in vitro (FIG. 1C, lane 10) when compared to wild-type hnRNP-E1 and wild-type-like hnRNP-E1(G292A)-mutant (lanes 8, 9).

As shown in FIG. 1E, (lanes 2-4), specific antisense oligonucleotides to the 25-nt hnRNP-E1 mRNA cis-element led to a dose-dependent inhibition of translation of hnRNP-E1. By contrast, scrambled oligonucleotides failed to quench the translation of hnRNP-E1 (FIG. 1E, lanes 6-8). Thus, several lines of evidence suggested that interaction of homocysteinylated-hnRNP-E1 and the 25-nt cis-element in the 5'-UTR of hnRNP-E1 mRNA led to an increase in biosynthesis of hnRNP-E1 in vitro, and that the (HA)-hnRNP-E1 (C293S)-mutant was also capable of mediating similar effects even in the absence of homocysteine. Because (HA)-hnRNP-E1(C293S)-mutant similarly reacted with the 18-nt folate receptor-α mRNA cis-element in the absence of homocysteine (FIGS. 10A-10H), we quantified and compared the RNA-protein interactions involving these distinct cis-elements by formal dissociation constant studies (Table 1 and 2). When purified wild-type hnRNP-E1 was reacted with the 25-nt hnRNP-E1 mRNA cis-element in the presence of increasing physiologically relevant concentrations of L-homocysteine, there was a dose-dependent increase in binding affinity (Table 1); thus, the $K_D$ progressively decreased from a basal value of 1.93-nM (in the absence of L-homocysteine) to a $K_D$ of 1.14- and 0.62-nM in the presence of 10- and 50-μM L-homocysteine, respectively (P<0.05). Moreover, although the difference in basal $K_D$ values between wild-type hnRNP-E1 and wild-type-like hnRNP-E1(G292A)-mutant (in the absence of L-homocysteine) was not significant (1.93-nM versus 2.02-nM, respectively), the (HA)-hnRNP-E1(C293S)-mutant exhibited a significantly higher affinity for the 25-nt hnRNP-E1 mRNA cis-element even in the absence of L-homocysteine ($K_D$=0.39 nM). This reflected a significantly higher affinity than that observed when the wild-type hnRNP-E1 protein was reacted with the 25-nt hnRNP-E1 mRNA cis-element in the presence of 50-μM L-homocysteine ($K_D$=0.62 nM).

As expected, there was a progressive increase in binding affinity between wild-type hnRNP-E1 and folate receptor-α mRNA cis-element in the presence of increasing concentrations of L-homocysteine (Table 2). Here too, in the absence of L-homocysteine, the $K_D$ of both wild-type hnRNP-E1 and wild-type-like hnRNP-E1(G292A)-mutant for folate receptor-α mRNA cis-element was comparable, i.e., $K_D$=1.47-nM versus 1.57-nM, respectively. However, (HA)-hnRNP-E1 (C293 S)-mutant exhibited significantly higher affinity for folate receptor-α mRNA cis-element even in the absence of L-homocysteine; again, this value ($K_D$=0.27-nM) reflected a significantly higher affinity than the value of the wild-type hnRNP-E1 for this cis-element in the presence of 50-μM L-homocysteine ($K_D$=0.47-nM). Taken together, these data confirmed that (a), like its interaction with folate receptor-α mRNA cis-element, homocysteinylated-hnRNP-E1 also bound the 25-nt hnRNP-E1 mRNA cis-element with high affinity at physiological concentrations of L-homocysteine, as would be found in mild-to-moderate folate deficiency in vivo; and (b), the (HA)-hnRNP-E1(C293S)-mutant was capable of binding both the hnRNP-E1 mRNA cis-element as well as the folate receptor-α mRNA cis-element with similarly high (but not identical) affinity even in the absence of homocysteine.

Post-Transcriptional Up-Regulation of hnRNP-E1 in Placental Cells Involves Interaction of the 25-Nt hnRNP-E1 Cis-Element and Homocysteinylated-hnRNP-E1.

Both folate receptors and hnRNP-E1 were comparably up-regulated at the post-transcriptional level under folate-depleted conditions in placental JAR and 1584 cell lines (FIGS. 11A-11D). Accordingly, the latter cell line was selected to further characterize the role of a specific RNA-protein interaction in the post-transcriptional up-regulation of hnRNP-E1 within cells. As shown in FIGS. 2A-2B, folate-depleted placental 1584-LF cells exhibited a 9-fold overexpression of folate receptor proteins with only a 1.6-fold increase in folate receptor mRNA over basal values found in folate-replete placental 1584-HF cells. Likewise, there was an over 2-fold increase in hnRNP-E1 protein in folate-depleted cells, which was associated with only one-third the basal expression of hnRNP-E1 mRNA found in folate-replete cells. Thus, the disproportionately higher folate receptor and hnRNP-E1 protein overexpression when compared to folate receptor and hnRNP-E1 mRNA transcripts suggested that both these proteins were up-regulated at the post-transcriptional level.

As shown in FIG. 2C, transfection of a control pCAT construct into folate-replete placental 1584-HF cells did not show a rise in CAT activity under basal conditions or after incubation with 50-μM L-homocysteine for 3-h at 37° C. By contrast, 25-nt hnRNP-E1 cis-element-driven CAT reporter constructs led to a three-fold greater CAT activity over control CAT constructs (even without added homocysteine). This suggested that the basal concentration of thiols (including cysteine and glutathione and L-homocysteine) extant in folate-replete cells, could be responsible for facilitating constitutive interaction of endogenous hnRNP-E1 with the 25-nt hnRNP-E1 cis-element-linked CAT reporter (FIG. 2C). Furthermore, when cells transfected with the 25-nt hnRNP-E1 cis-element-driven CAT reporter construct were exposed to 50-μM L-homocysteine for 3-h at 37° C., there was a further significant increase in CAT activity over baseline (FIG. 2C). This confirmed that the interaction of endogenous hnRNP-E1 with the 25-nt hnRNP-E1 cis-element would be further increased by accumulated intracellular L-homocysteine found in clinical folate deficiency. Taken together, these data on placental 1584-HF cells, which were comparable to earlier studies on the interaction of homocysteinylated-hnRNP-E1 with 18-nt folate receptor-α mRNA cis-element in HeLa-IU₁ cells, predicted that folate deficiency would similarly trigger the translational up-regulation of hnRNP-E1 through this RNA-protein interaction.

Next we sought to capture endogenous RNA-protein complexes composed of hnRNP-E1 mRNA cis-element bound hnRNP-E1 from either folate-replete placental 1584-HF or folate-depleted 1584-LF cells, as well as from 1584-HF cells acutely exposed to L-homocysteine. FIG. 2D demonstrated the specificity of our [$^{35}$S] labeled antisense hnRNP-E1 mRNA cis-element probe, which reacted only with hnRNP-E1 plasmids (lane 8) but not with a plasmid containing folate receptor-α DNA (lane 9). In addition, the 18-nt folate receptor-α mRNA cis-element reacted with the folate receptor-α plasmid, but failed to react with the hnRNP-E1 plasmid (FIG. 2E); this confirmed there were no common sequences that could result in false positive signals with the probe used in FIG. 2D. As shown in FIG. 2D, lane 1, there was evidence of hnRNP-E1 bound mRNA cis-element signals signifying the constitutive existence of RNA-protein complexes within 1584-HF cells. Furthermore, experimental induction of the accumulation of L-homocysteine within placental 1584-HF cells led to a progressive dose-dependent increase in signal (FIG. 2D, lanes 2-5) when compared to baseline values. This reflected the dynamic responsiveness of this system to L-homocysteine (by formation of additional RNA-protein complexes). Because 1584-LF cells accumulated more L-homocysteine than 1584-HF cells (FIG. 3D), this predicted significantly more intracellular RNA-protein complexes captured from 1584-LF cells, as confirmed in FIG. 2D, (lane 7 versus lane 6). Taken together, these results demonstrated increased specific hybridization signals with radiolabeled antisense 25-nt hnRNP-E1 mRNA cis-element probe, which reflected the capture of 25-nt hnRNP-E1 mRNA cis-element-bound hnRNP-E1 protein complexes within placental 1584-HF cells, both constitutively and in response to L-homocysteine.

Comparison of the Effect of Various Thiols on RNA Protein Interactions.

Figure 3A:
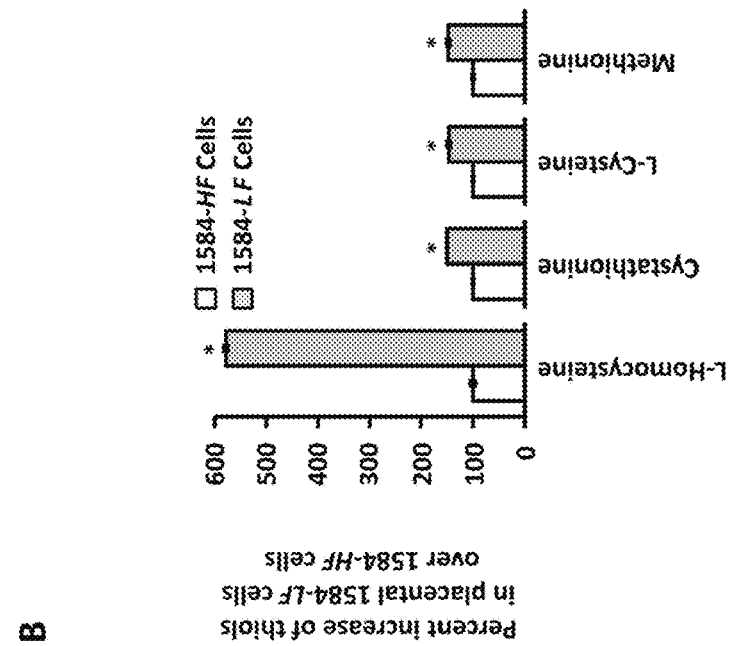
FIGS. 3A-3B characterize the influence of various thiols on the interaction between hnRNP-E1 protein and the 25-nt hnRNP-E1 mRNA cis-element (A), and the accumulation of various thiol amino acids in placental 1584-LF versus 1584-HF cells (B). The result (A) is representative of 2 studies that gave comparable results. (A) Gel-shift assays showing the interaction between 0.5 μg dialyzed recombinant hnRNP-E1 protein and [$^{35}$S]25-nt hnRNP-E1 mRNA cis-element (1×10$^5$ cpm) in the presence of various indicated thiols. (B) Comparison of the percent increase of various thiols in placental 1584-LF over 1584-HF cells; the data was taken from Table 4 to highlight the percent increase in homocysteine over other thiols in folate-depleted cells. GST, glutathione S-transferase; hnRNP-E1, wild-type hnRNP-E1; 1584-HF cells, placental 1584 cells stably adapted to high folate; 1584-LF cells, placental 1584 cells stably adapted to low folate; 25-nt, 25-nucleotide.

As shown in FIG. 3A, there were much stronger RNA-protein signals with 100-μM of non-physiological thiols (dithiothreitol and ß-ME) than physiological L-homocysteine; however, by contrast, signals with equimolar concentrations of other physiological thiols like L-cysteine were far weaker, and there were no detectable signals with either glutathione or methionine. Despite inclusion of physiologically relevant concentrations of glutathione (10-mM) in the reaction mixture, there was a dose-dependent increase in RNA-protein complex formation with even 5-μM L-homocysteine. During the course of these studies, we noted that recent batches of commercially available L-homocysteine led to RNA-protein interactions between hnRNP-E1 and 25-nt hnRNP-E1 mRNA cis-element at lower concentrations than previously noted.

When the $K_D$ of the RNA-protein interaction was tested in the presence of 10-mM glutathione and equimolar concentrations of L-homocysteine and L-cysteine, there was a significantly higher affinity obtained with L-homocysteine (quantified by a lower $K_D$) (Table 3). These studies were generally comparable to RNA-protein interactions involving folate receptor-α mRNA binding to hnRNP-E1.

Figure 3B:
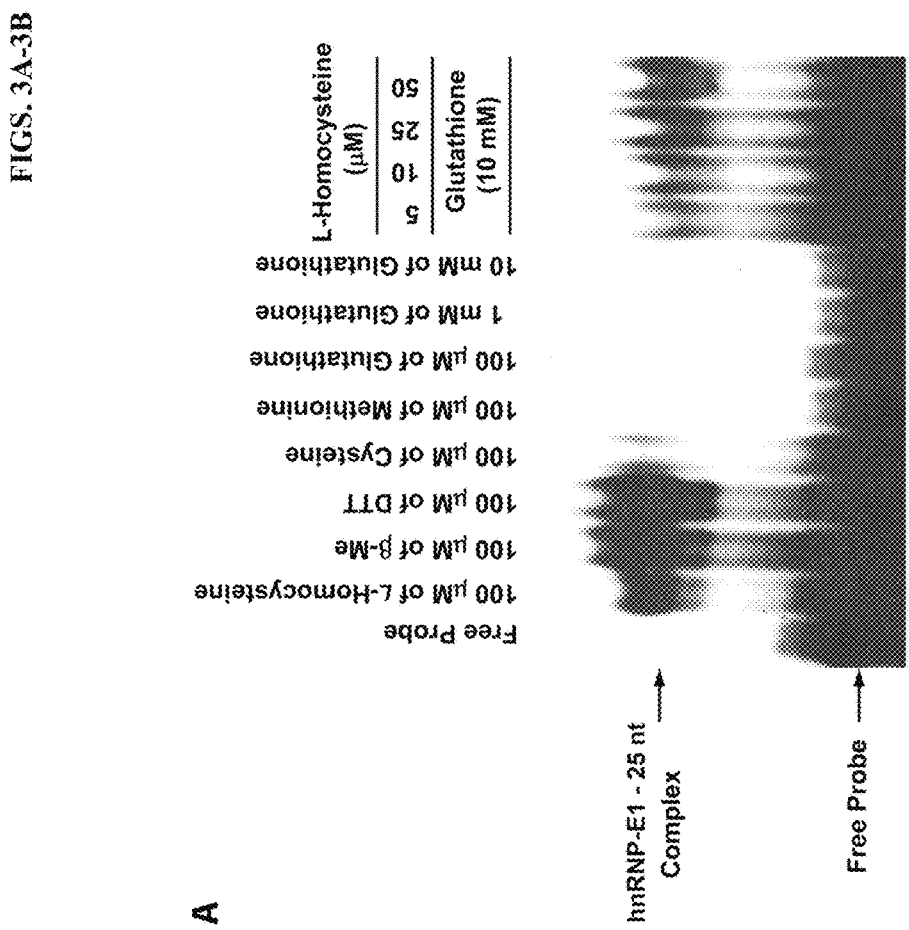

There was a less than 2-fold increase in other thiols (cystathionine, cysteine, and methionine) in 1584-LF cells when compared to 1584-HF cells. However, there was a 5.75-fold increase in homocysteine in 1584-LF cells when compared to 1584-HF cells (184-μM versus 32-11M, respectively) (Table 4 and FIG. 3B). Thus, although the basal concentration of cysteine in 1584-HF cells was high (327-μM), and rose only 1.5-fold more in 1584-LF cells, based on data in FIG. 3A, it was not likely that these concentrations would have had as much influence in increasing binding affinity of the RNA-protein interaction as L-homocysteine, which rose nearly 6-fold in folate-deficient cells.

Effect of Mutation of the 25-Nt hnRNP-E1 Cis-Element on the RNA Protein Interaction.

Figure 4A:
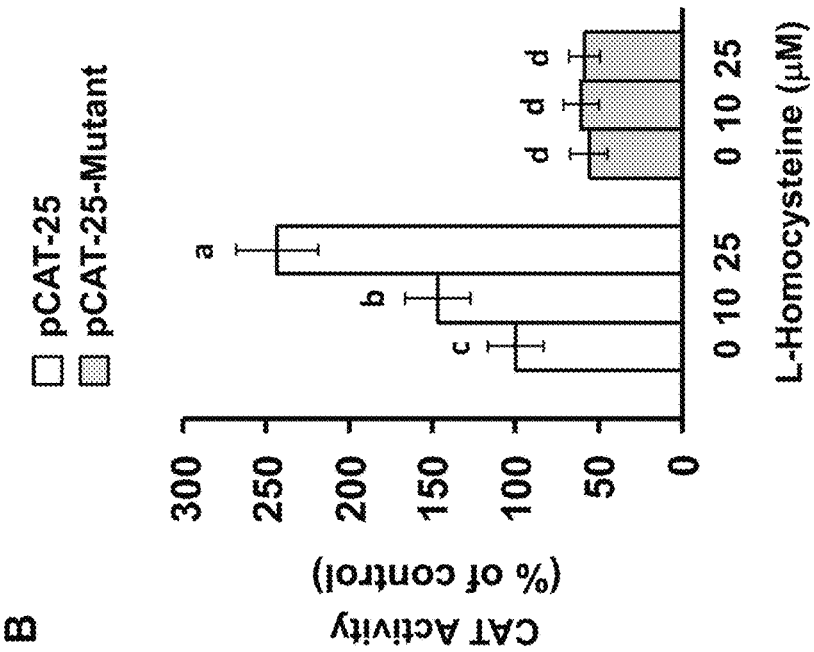
FIGS. 4A-4B demonstrates the effect of specific mutations within the 25-nt hnRNP-E1 mRNA cis-element (A) on the RNA-protein interaction, and CAT reporter activity following transfection into placental 1584-HF cells. (A) Gel-shift assays to assess the capacity of individual indicated 25-nt hnRNP-E1 RNA mutants generated in Table 5 (numbered from 1-7) to bind to purified recombinant GST-hnRNP-E1 in the presence of 15-μM L-homocysteine. (B) Comparison of CAT reporter activity following transfection of either wild-type 25-nt hnRNP-E1 cis-element-driven CAT reporter construct or a mutated 25-nt hnRNP-E1-cis-element bearing mutant #6-driven CAT reporter construct into placental 1584-HF cells. The results are presented as the mean±SD, n=3 (means of triplicates). Labeled means without a common letter differ, P<0.05. GST, glutathione S-transferase; hnRNP-E1, wild-type hnRNP-E1; pCAT-25, wild-type 25-nt hnRNP-E1 cis-element-driven CAT reporter construct; pCAT-25-Mutant, mutant 25-nt hnRNP-E1 cis-element bearing mutant#6-driven CAT reporter construct; 25-nt, 25-nucleotide.
Figure 4B:
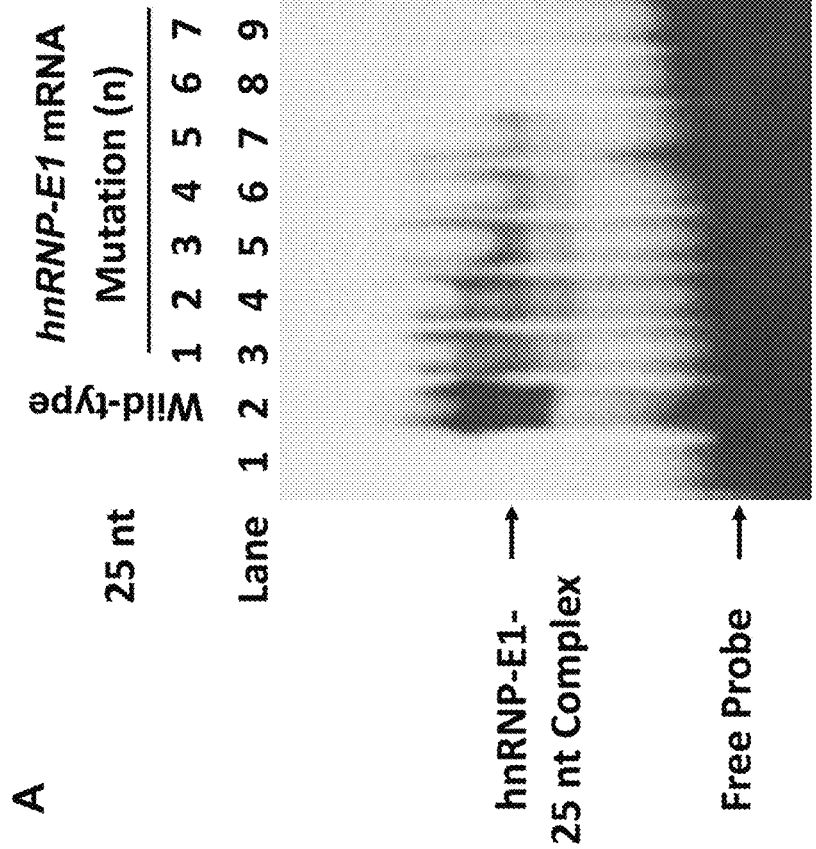

Studies with 18-nt folate receptor-α mRNA cis-element suggested that the sequence motif of CUCC in tandem (with intervening nucleotides) could be important for interaction with hnRNP-E1. Because the 25-nt hnRNP-E1 mRNA cis-element contained three such distinct CUCC sequences, we evaluated the effect of mutating a single nucleotide within each of these CUCC sequences on the specificity of binding of hnRNP-E1 to the hnRNP-E1 mRNA cis-element using gel-shift assays. We noted that various mutations, numbered 1 to 5, (Table 5 and FIG. 4A) led to progressively quenched RNA-protein interaction signals. Of significance, mutation#6 (involving the first and third CUCC sequences) led to complete quenching of the signal. Thus, the integrity of the first and third CUCC sequence motif in 25-nt hnRNP-E1 mRNA cis-element was critical for interaction with homocysteinylated-hnRNP-E1 in vitro. Moreover, although wild-type-25-nt hnRNP-E1 cis-element placed proximal to CAT reporter led to progressively increased and statistically significant CAT reporter signal in response to exogenously added L-homocysteine (FIG. 4B), mutation#6 of hnRNP-E1 mRNA cis-element placed proximal to CAT reporters yielded no such response. Thus, these mutations in hnRNP-E1 cis-element were also functionally relevant within placental cells.

Effect of Transfection of Specific Antisense Oligonucleotides on the Biosynthesis of hnRNP-E1.

As shown in Table 6, transfection of wild-type- and scrambled-oligonucleotides did not significantly alter the biosynthetic rate of hnRNP-E1 (similar rates of 1.0-fmol [$^{35}$S]cysteine/mg protein/h incorporated into hnRNP-E1); by contrast, transfection of antisense oligonucleotides to 25-nt mRNA cis-element of hnRNP-E1 led to a significant reduction in the biosynthetic rate of newly synthesized hnRNP-E1 of 0.62-fmol [$^{35}$S]cysteine/mg protein/h incorporated into hnRNP-E1 (Table 6).

Effect of RNA interference of hnRNP-E1 mRNA on the biosynthesis of hnRNP-E1.

Figure 5:
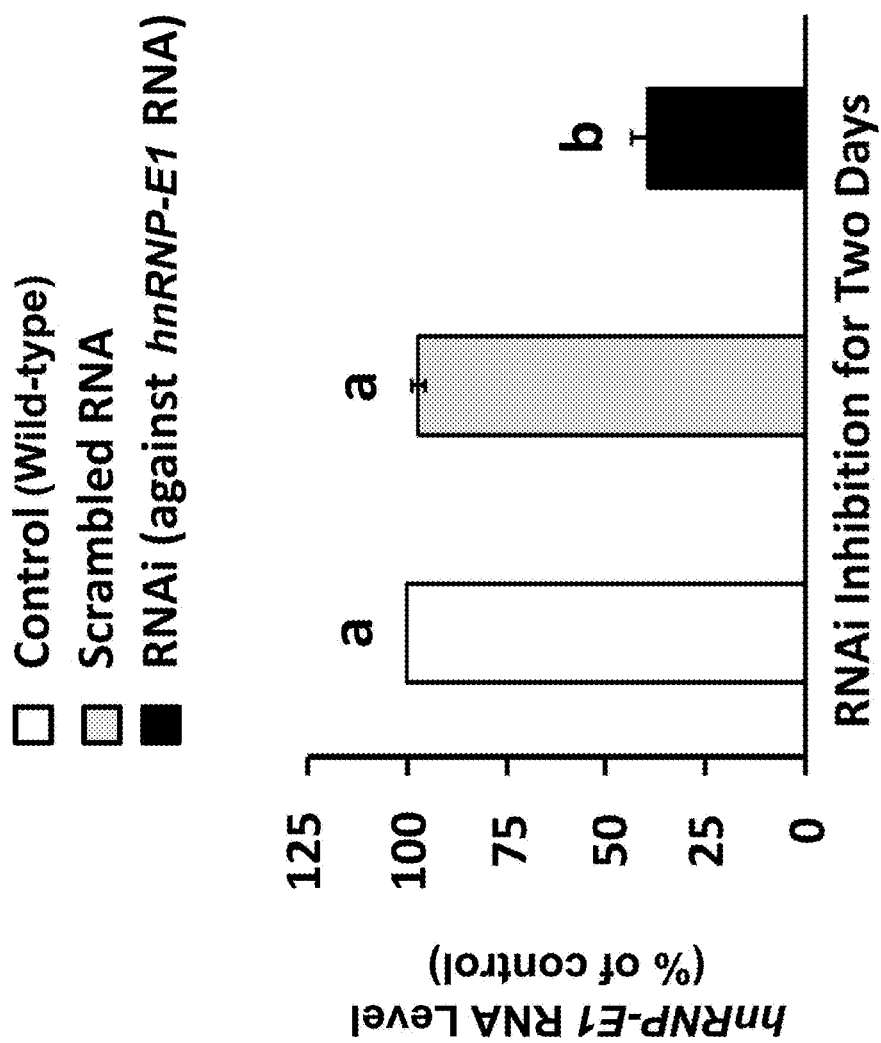
FIG. 5 shows evidence for the specificity of RNA interference (RNAi) against hnRNP-E1 mRNA in placental 1584-HF cells. The results are presented as the mean±SD, n=3 (means of triplicates). Labeled means without a common letter differ, P<0.05. 1584-HF cells, placental 1584 cells stably adapted to high folate.

Transfection of siRNA directed specifically to hnRNP-E1 mRNA, which did not impact on hnRNP-E2, led to less cell death after 2 days, and achieved ~60% reduction of hnRNP-E1 mRNA (FIG. 5). As shown in Table 7, when compared to basal control values using scrambled RNA which had comparable values as wild-type cells, there was a significant reduction in rate of biosynthesis of hnRNP-E1 and folate receptor proteins. Specifically, there was a reduction in the rate of newly synthesized hnRNP-E1 from 0.95- to 0.32-fmol of L-[$^{35}$S]cysteine incorporated into hnRNP-E1/mg protein/h, in scrambled-versus siRNA-treated cells, respectively (Table 7). Likewise, there was a reduction in the rate of newly synthesized folate receptor from 1.57- to 0.35-fmol of L-[$^{35}$S]cysteine incorporated into hnRNP-E1/mg protein/h, in scrambled-versus siRNA-treated cells, respectively (Table 7). This pointed to the specificity of effects of RNA interference of hnRNP-E1 mRNA on the biosynthesis of hnRNP-E1 within cells. And because folate receptor biosynthesis is mediated by hnRNP-E1, the co-reduction of biosynthesis of folate receptor also verified the effects of RNA interference of hnRNP-E1 mRNA on reduction of both hnRNP-E1. These studies unambiguously confirmed that hnRNP-E1 was directly involved in the cellular biosynthesis of hnRNP-E1 and folate receptor proteins. Moreover, because there was a reduction of the basal rate of hnRNP-E1 (and folate receptor) biosynthesis even in placental 1584-HF cells, these data suggest that the constitutive expression of hnRNP-E1 (and folate receptors) in these cells is also mediated by hnRNP-E1 interaction with both 25-nt hnRNP-E1 mRNA cis-elements and 18-nt folate receptor-α mRNA cis-elements. Together, the data in FIGS. 4A-4B, FIG. 5, Table 6 and Table 7 further confirmed the specificity of the RNA-protein interaction involving hnRNP-E1 binding to its own mRNA cis-element for the biosynthesis of hnRNP-E1 at the post-transcriptional level in placental 1584-HF cells.

Triggering the Biosynthesis of Folate Receptor and hnRNP-E1 Proteins by Introduction of (HA)-hnRNP-E1 (C293S)-Mutant Proteins into Cells.

(HA)-hnRNP-E1(C293 S)-mutant proteins interact with both the 25-nt hnRNP-E1 RNA cis-element and 18-nt folate receptor-α mRNA cis-element in the absence of L-homocysteine in vitro (FIGS. 10A-10H; FIGS. 1A-1E, and Table 1). Therefore, we tested the potential of liposome-transfected (HA)-hnRNP-E1(C293S)-mutant proteins to bind to both these endogenous hnRNP-E1- and folate receptor-mRNA cis-elements and trigger the biosynthesis of hnRNP-E1 and folate receptors in 1584-HF cells (where homocysteine concentrations are at basal levels). As shown in Table 8, wild-type hnRNP-E1 proteins induced a significant increase in biosynthesis of [$^{35}$S]hnRNP-E1 when compared to basal rates (1.12-versus 0.53-fmol [$^{35}$S]cysteine incorporated into hnRNP-E1/mg protein/h, respectively). Similarly wild-type-like hnRNP-E1(G292A)-mutant also resulted in a comparable rise in rates of [$^{35}$S]hnRNP-E1 biosynthesis (1.03 fmol/mg protein/h) as wild-type hnRNP-E1. By contrast, the introduction of (HA)-hnRNP-E1(C293S)-mutant proteins led to a significant (over 6-fold) increase in the rate of biosynthesis of [$^{35}$S]hnRNP-E1 (to 6.70-fmol/mg protein/h). There were also comparable results in stimulation of the biosynthesis of newly synthesized folate receptors after transfection of these proteins into placental 1584-HF cells (Table 8). Whereas control wild-type hnRNP-E1 and wild-type-like hnRNP-E1(G292A)-mutant proteins comparably stimulated the biosynthesis of [$^{35}$S]folate receptors (1.62- versus 1.79-fmol/mg protein/h, respectively) over basal values, the (HA)-hnRNP-E1(C293S)-mutant significantly induced a nearly 4-fold increase of [$^{35}$S]folate receptors (up to 6.62-fmol/mg protein/h) over controls (Table 8). Thus, transfection of liposomes bearing purified wild-type, wild-type-like hnRNP-E1(G292A)-mutant, and (HA)-hnRNP-E1 (C293S)-mutant proteins into cells led to functional interactions with both endogenous 25-nt hnRNP-E1 mRNA cis-elements and 18-nt folate receptor mRNA cis-elements, leading to significantly increased biosynthesis of hnRNP-E1 and folate receptor proteins, respectively.

Figures 6A, 6B, 6C, 6D, 6E, 6F:
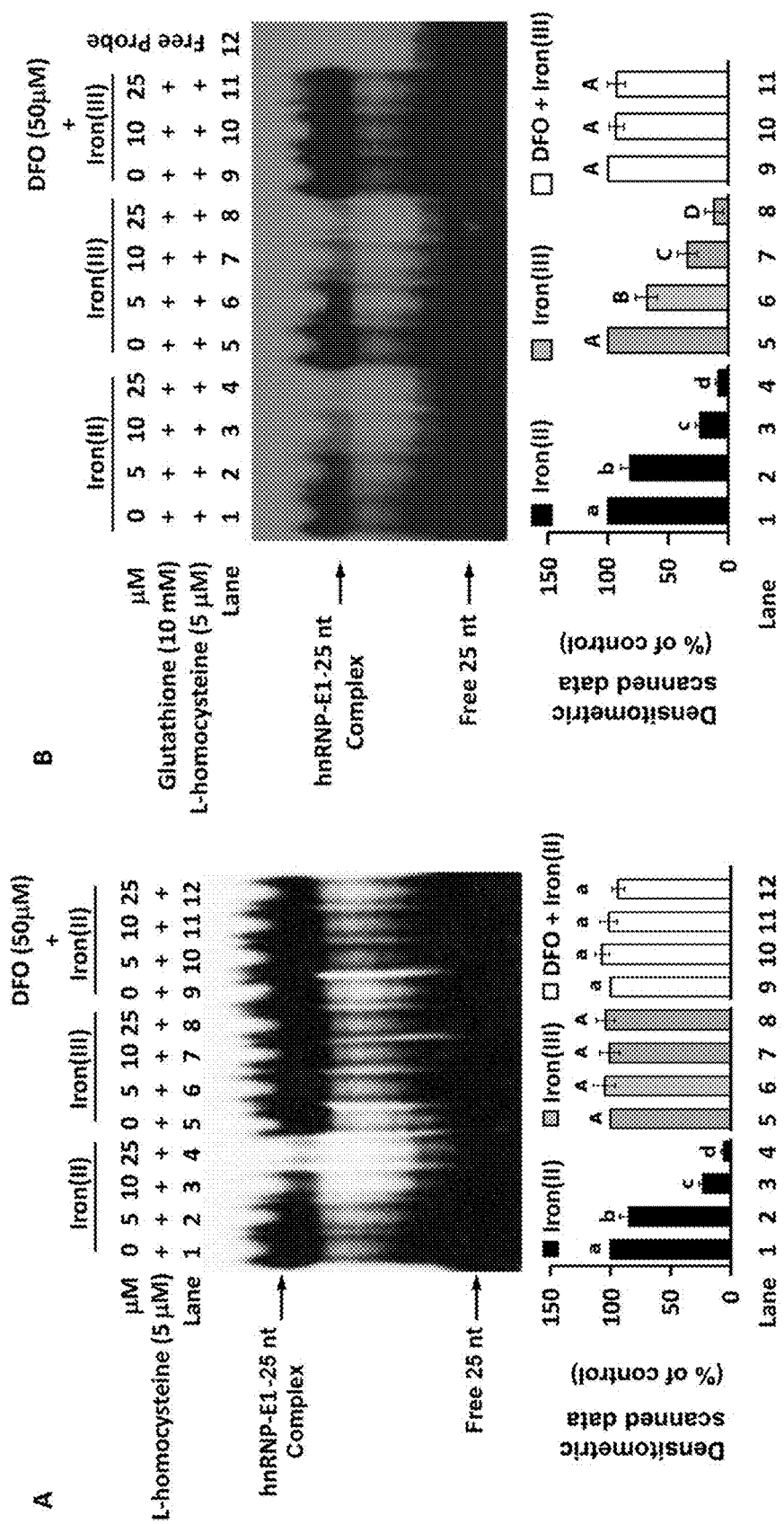
FIGS. 6A-6F Characterization of the specific effect of iron(II) or iron(III) on the L-homocysteine-triggered RNA-protein interaction involving 25-nt hnRNP-E1 mRNA cis-element and purified recombinant GST-hnRNP-E1 by gel shift assays (A, B), and in vitro translation assays (C-F). (A, B) Effect of iron(II) or iron(III) on the RNA-protein interaction in the absence (A) or presence of 10 mM glutathione (B). (C, D, E, F) Effect of addition of either iron(II) (C), deferoxamine (D), or varying combinations of iron(II) and deferoxamine (E, F) on the translation of hnRNP-E1 in vitro. Each of these representative gels is from 3 independent sets of experiments that gave comparable data with less than 10% variation. The pooled densitometric scanned data from 3 independent experiments (in A, B, C) are shown as a bar graph below one representative gel; these data are presented as mean±SD, n=3. Labeled means without a common letter differ, P<0.05. 25-nt, 25-nucleotide, DFO, deferoxamine; GST, glutathione S-transferase; hnRNP-E1, wild-type hnRNP-E1.
Figures 6A, 6B, 6C, 6D, 6E, 6F:
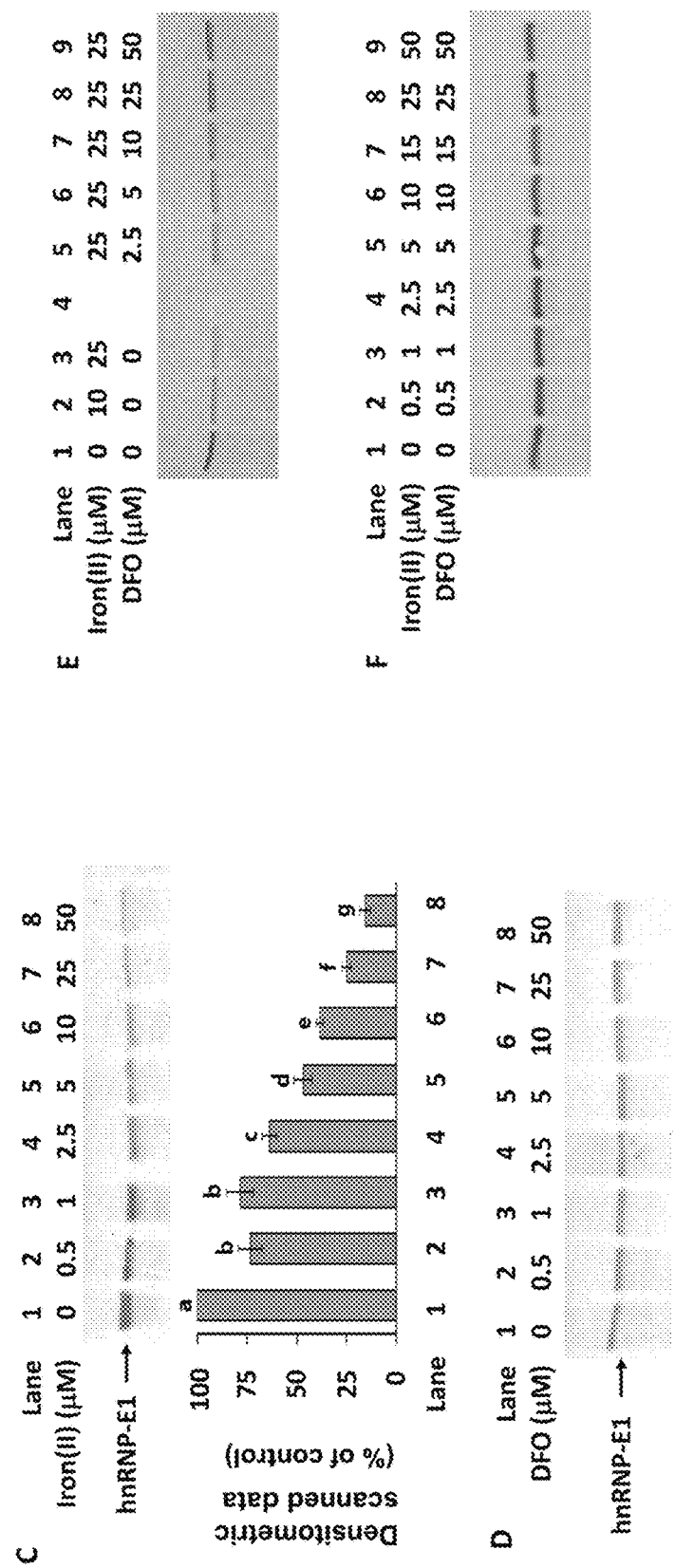

Effect of Iron(II) on the Interaction Between hnRNP-E1 and the 25-Nt hnRNP-E1 mRNA Cis-Element.

hnRNP-E1 is an iron(II)-binding protein that directly binds ferrous iron with micromolar affinity (3:1 ratio of iron to hnRNP-E1). So we evaluated if iron(II) had a specific modulating effect in the homocysteine-induced RNA-protein interaction. The sensitivity of the system was markedly improved by use of fresh radiolabeled [$^{35}$S]25-nt hnRNP-E1 cis-element, freshly opened vials of commercially purchased L-homocysteine and iron(II), and incubating iron(II) with dialyzed, purified GST-hnRNP-E1 before the addition of radiolabeled RNA and L-homocysteine. In the presence of a fixed concentration of L-homocysteine, iron(II) exerted a dose-dependent inhibitory effect on the formation of these RNA-protein complexes (FIG. 6A, lanes 2-4). By contrast, iron(III) had no such influence (FIG. 6A, lanes 6-8). The quenching effect of iron(II) was near-completely blocked by the addition of 50 µM deferoxamine to the reaction mixture (FIG. 6A, lanes 10-12); this confirmed the specificity of the inhibitory effect of iron(II) on the formation of these RNA-protein complexes in the presence of L-homocysteine. To eliminate the potential of iron(II) to catalyze oxidation changes in proteins (hnRNP-E1) and potentially nucleic acids (hnRNP-E1 mRNA cis-element) that could have also led to reduced RNA-protein interaction, these experiments were repeated in the presence of physiologically relevant concentrations of glutathione; under these conditions, iron (III) is converted to iron(II) at pH 7.0. Accordingly, when 10-mM glutathione was included in all reaction mixtures, both iron(II) and iron(III) exerted a comparable dose-dependent reduction in RNA-complex formation on gel-shift assays (FIG. 6B, lanes 2-4 versus 6-8). The ability of deferoxamine to eliminate the quenching effect of iron(III) in the presence of glutathione confirmed the specificity of effect of iron(III) that was converted to iron(II) (FIG. 6B, lanes 10-11). Thus the possibility of direct oxidative effects of iron(II) on hnRNP-E1 or RNA was unlikely. To confirm that this was a general effect of iron(II) on the capacity of hnRNP-E1 to interact with other target mRNAs in the presence of L-homocysteine, we were able to reproduce this effect of iron(II) when 18-nt folate receptor-α mRNA cis-element was substituted for the 25-nt hnRNP-E1 mRNA cis-element (data not shown).

As shown in FIG. 6C, iron(II) also had a dose-dependent impact in quenching the in vitro translation of hnRNP-E1 in the presence of 4.1-mM ß-ME; of significance, even 0.5- to 1-µM of iron(II) consistently led to a negative effect when compared to basal levels, suggesting there could be a physiological effect within cells. Conversely, deferoxamine alone did not independently influence in vitro translation of hnRNP-E1 (FIG. 6D); this suggested there was little free iron(II) available for chelation within the reticulocyte-rich lysates. However deferoxamine, in a dose-dependent manner, was capable of progressively reversing the quenching effect of 25-µM iron(II) on translation of hnRNP-E1 (FIG. 6E, lanes 5-9). Equimolar concentration of deferoxamine added to iron(II) was also effective in preventing an inhibitory effect of iron(II) on translation of hnRNP-E1 (FIG. 6F). Finally, iron(II) induced a dose-dependent reduction in RNA-protein binding affinity, as indicated by the progressive increase in $K_D$ (Table 9). Taken together these data suggested that whereas hnRNP-E1 readily reacted with target mRNA cis-elements in the presence L-homocysteine, the prior binding of iron(II) to hnRNP-E1 significantly quenched this L-homocysteine-triggered RNA-protein interaction.

Dual Up-Regulation of hnRNP-E1 and Folate Receptors in Tumor Xenografts Propagated in Folate-Deficient Mice.

Because hnRNP-E1 could bind two distinct cis-elements in cultured placental cells, we pursued investigations whether there was dual up-regulation of folate receptors and hnRNP-E1 in vivo in placentas of pregnant mice fed a folate-deficient diet when compared to folate-replete dams. However there was significant apoptosis of megaloblastic placental trophoblastic cells in situ, which led to significant architectural changes only in placentas of folate-deficient dams (FIGS. 12A-12D). Because the trophoblastic cell mass is also the major locus of expression of folate receptors and hnRNP-E1, it was not meaningful to directly compare expression of folate receptors or hnRNP-E1 of placentas between folate-replete and folate-deficient dams.

Figures 7A, 7B, 7C, 7D, 7E, 7F:
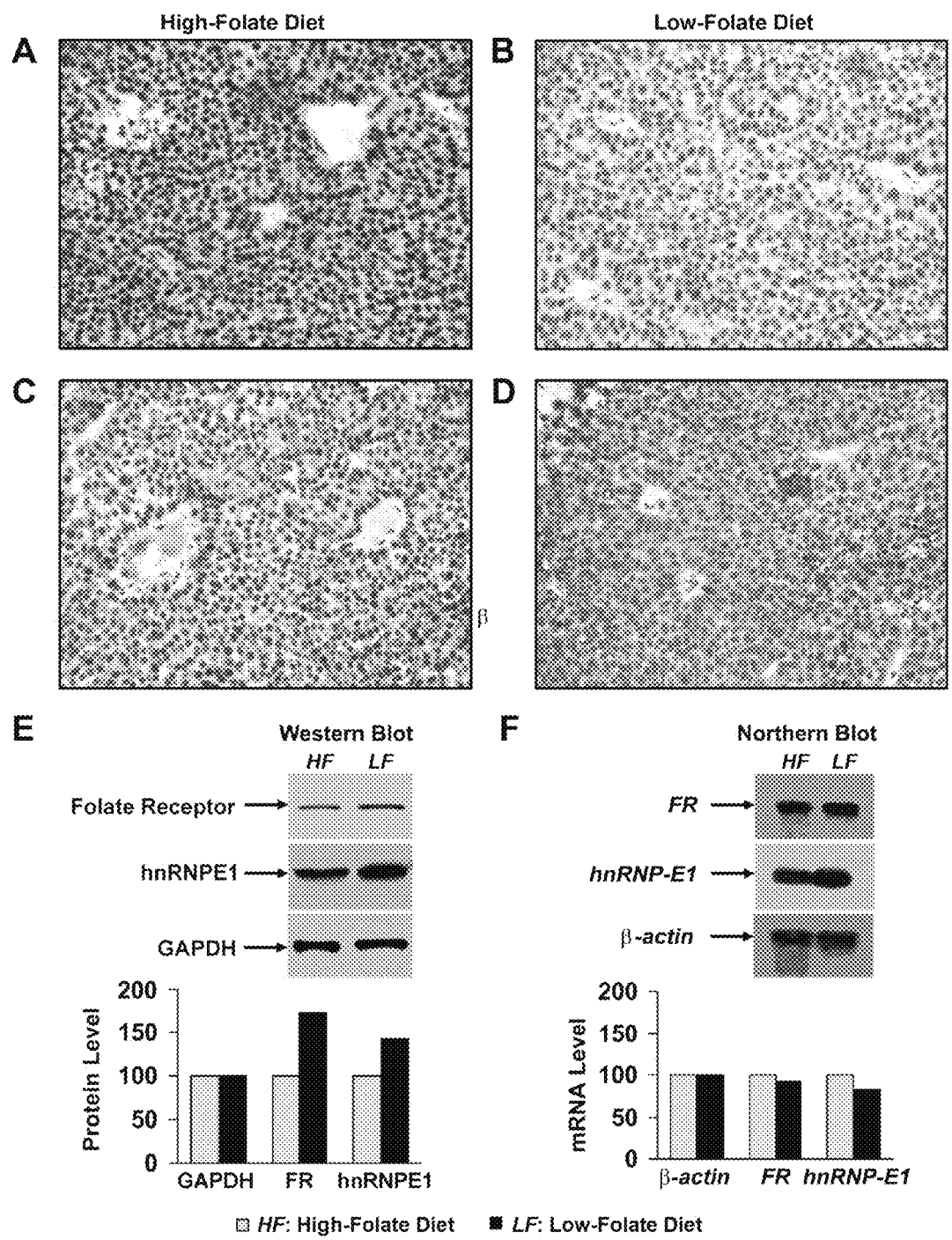
FIGS. 7A-7F show dual up-regulation of hnRNP-E1 and folate receptors at the post-transcriptional level in HeLa-IU$_1$-derived tumor xenografts of mice fed either a folate-replete diet (A, C) or folate-deficient diet (B, D) for one month prior to, and after, implantation of 1 million HeLa-IU$_1$ cells into their flanks. Due to prohibitive costs, this longitudinal experiment was carried out only once; similar results were obtained from two randomly selected tumors each from folate-replete mice [n=6] and folate-deficient mice [n=5]. (A, B, C, D) Immunohistochemistry for hnRNP-E1 using nonimmune serum (A, B), compared to anti-hnRNP-E1 antiserum (C, D). Magnification was ×40. (E) Western blots (50-μg tumor protein probed with either anti-folate receptor antiserum, anti-hnRNP-E1 antiserum or anti-GAPDH antibodies) to assess the expression of folate receptor and hnRNP-E1 in the tumor. Densitometric evaluation of folate receptor and hnRNP-E1 protein signals in relation to GAPDH is shown below the gels. (F) Northern blots (20-lag total tumor RNA) to assess folate receptor-α mRNA and hnRNP-E1 mRNA in tumor xenografts. Densitometric scanning of the signals from Northern blots was adjusted by a loading control (β-actin) and is shown below the gel. HF, high-folate (1200 nmol/folate/kg) diet; LF, low-folate (400 nmol folate/kg) diet; GAPDH, glyceraldehyde-3-phosphate dehydrogenase; FR, folate receptor.

Accordingly, we evaluated the possibility of a dual up-regulation of both folate receptor and hnRNP-E1 in HeLa-$IU_1$ cell-derived tumor xenografts in an athymic mouse model, where the tumor was homogeneous and the folate content of the murine diet was controlled. Mice fed a folate-restricted diet (120-nmol folate/kg diet) versus a folate replete (1200-nmol folate/kg diet) throughout the 4 weeks prior to injection of HeLa-$IU_1$ cells into their flanks and over the ensuing 4 weeks, did not exhibit differences in amount of food consumed or weight. However, the folate-restricted diet resulted in a serum homocysteine of 185-µM (consistent with severe folate deficiency), which was nearly 10-times more than the serum homocysteine (19-µM) of control mice. As shown in FIGS. 7A-7D, immunohistochemical studies for tumor hnRNP-E1 expression using anti-hnRNP-E1 antiserum revealed enhanced brown staining in folate-deficient xenografts (FIG. 7D) when compared to folate-replete xenografts (FIG. 7C); by contrast, there was little staining using nonimmune serum (FIGS. 7A-7B). When compared to tumors from mice fed a folate-replete diet (FIGS. 7A and 7C), tumors that developed in folate-deficient mice (FIGS. 7B and 7D) exhibited megaloblastic features with larger nuclei and open chromatin and an abundant cytoplasm (reflecting a high nuclear-cytoplasmic ratio) and consequently fewer cells per ×40 magnification field. Western blot analysis using anti-folate receptor antiserum as well as anti-hnRNP-E1 antiserum, confirmed an increased signal reflecting up-regulation of both folate receptors and hnRNP-E1 in tumor xenografts of folate-deficient mice. Moreover, Northern blots (FIG. 7F) showed insignificant changes in mRNA levels for both folate receptor and hnRNP-E1 mRNA. Thus, there was evidence for up-regulation for both folate receptor and hnRNP-E1 protein levels within xenografts of animals that experienced folate deficiency, which likely occurred at the post-transcriptional level. Parenthetically, although immunohistochemistry of tumors revealed more abundant staining of hnRNP-E1 in cytoplasm and nuclei when compared to Western blots of tumor cytosol, the concordance between these distinctly different methods, which confirmed up-regulation of hnRNP-E1 and folate receptors in response to folate deficiency, was the important finding. These data were also concordant with those of cultured placental cells propagated in low-folate medium, as well as the observed effects of homocysteinylated-hnRNP-E1 and (HA)-hnRNP-E1 (C293S)-mutant proteins in triggering the biosynthesis of folate receptors and hnRNP-E1 in these cells.

Specificity of RNA Protein Interactions and Anti-hnRNP-E1 Antiserum—

Because hnRNP-E1 is encoded by an intronless gene arising from hnRNP-E2 through a transposition event and there is 100% homology among K-homology domains of hnRNP-E1 and hnRNP-E2, it was necessary to identify the extent to which the antiserum against hnRNP-E1 peptides recognized hnRNP-E2. The antiserum was developed against a 19-peptide sequence in hnRNP-E1 as previous described (Xiao et al. "Isolation and characterization of a folate receptor mRNA-binding trans-factor from human placenta. Evidence favoring identity with heterogeneous nuclear ribonucleoprotein E1. *J Biol Chem.*, 2001, 276: 41510-41517, incorporated herein by reference). Our polyclonal anti-peptide antiserum developed against a 19-peptide sequence in hnRNP-E1, was outside of KH domains, and recognized a common sequence of only 8- or 5-peptides in hnRNP-E2 (FIG. 9A, middle row). When equivalent amounts of hnRNP-E1 and hnRNP-E2 were tested by Western blots with anti-hnRNP-E1 antiserum, there was a very strong signal with hnRNP-E1 and a much fainter signal with hnRNP-E2. When the densitometric scans were compared, over 88% of the signal reflected hnRNP-E1 whereas at most 12% of the total signal was accounted by hnRNP-E2. Thus, there was poor recognition of hnRNP-E2 by our anti-hnRNP-E1 antiserum.

Selection of the Most Effective Molecular Mimic of Homocysteinylated-hnRNP-E1 and its Control—

Recombinant glutathione S-transferase (GST)-plasmid DNA, pGST-hnRNP-E1 and related engineered variant plasmids were transformed into BL21 *Escherichia coli* from Novagen (Madison, Wis.). After induction by 1 mM isopropyl-1-thio-ß-D-galactopyranoside, the wild-type and engineered variant GST-hnRNP-E1 fusion proteins were individually purified using the B-PER GST Fusion Protein Purification Kit (Pierce, Rockford, Ill.). The eluted GST fusion proteins were then dialyzed against 500 volumes of thiol-free buffer to remove excess reducing reagents; (in FIGS. 10B-10G, the mutant proteins are identified by the notation pE1, which precedes the listing of a specific mutation). Analysis by SDS-PAGE and Western blots using anti-peptide hnRNP-E1 antiserum revealed single 69-kDa proteins that were related to GST-hnRNP-E1 (FIG. 10B). Next, the capacity of each of these purified recombinant GST-hnRNP-E1 mutant proteins to bind both folate receptor-$\alpha$ mRNA and HPV16 L2 mRNA cis-elements was subsequently assessed, because they are members of the same post-transcriptional RNA operon that is modulated by homocysteinylated-hnRNP-E1. Although several hnRNP-E1-mutant proteins variably interacted with the 18-nt folate receptor-$\alpha$ mRNA cis-element in the absence of either homocysteine or other reducing agent, the mutant protein involving Cys-293 in the KH3 domain, hnRNP-E1(C293S)-mutant, gave the strongest RNA-protein signal (FIG. 10C, lane 10). By contrast, control hnRNP-E1(G292A)-mutant proteins were wild-type-like in that they gave similar signals as wild-type hnRNP-E1 (FIG. 10C, lane 12 versus lane 2). Accordingly, wild-type hnRNP-E1, wild-type-like hnRNP-E1(G292A)-mutant, as well as hnRNP-E1(C54S)/(C293S)-mutants were further studied. As expected, the basal translation of folate receptor-$\alpha$ mRNA in vitro was diminished in a dose-dependent manner by NEM (FIG. 10D), which consumed much of the excess thiol groups contributed by an excess of ß-mercaptoethanol (ß-ME) (4.1-mM) that is normally found in the commercial in vitro translation reaction mixture. However, translation of folate receptor-$\alpha$ in the presence of 2-mM NEM was maximally increased by both hnRNP-E1(C54S)/(C293S)-mutants (FIG. 10E, lane 4, 6) when compared with wild-type hnRNP-E1 or wild-type-like hnRNP-E1(G292A)-mutants (FIG. 10E, lane 3, 7). Moreover, after HeLa-IU$_1$ cells were co-transfected with plasmids encoding either wild-type hnRNP-E1 or hnRNP-E1-mutants along with the 18-nt folate receptor-$\alpha$ mRNA cis-element-linked CAT reporter constructs (using pSV-$\beta$-gal for normalization), the hnRNP-E1(C293S)-mutant induced folate receptor-$\alpha$ cis-element-linked CAT activity more effectively than the hnRNP-E1(C54S)-mutant, and was two and one-half times stronger than control wild-type hnRNP-E1 or the wild-type-like hnRNP-E1(G292A)-mutant (FIG. 10F). The hnRNP-E1(C54S)/(C293S)-mutant proteins (FIG. 10G, lane 3, 5) were also capable of greater interaction with HPV16 L2 mRNA on gel-shift assays than wild-type hnRNP-E1 and wild-type-like hnRNP-E1(G292A)-mutants (FIG. 10G, lane 2, 6). As expected, a dose-dependent addition of wild-type hnRNP-E1 protein led to a progressive reduction in the in vitro translation of HPV16 L2 protein under basal conditions wherein excess ß-ME in the reaction mixture was not counteracted by NEM (FIG. 10H, lanes 1-4), whereas BSA had no such effect (FIG. 10H, lane 5-8). However, after quenching excess ß-ME by NEM, there was an insignificant reduction of HPV16 L2 protein signal with either wild-type hnRNP-E1 or wild-type-like hnRNP-E1(G292A)-mutant proteins (FIG. 10H, lanes 9-12 and 16-18, respectively); by contrast, under these conditions, the hnRNP-E1(C293S)-mutant protein induced a progressive reduction in signal (FIG. 10H, lanes 13-15). Based on these studies, this highest affinity (HA)-hnRNP-E1(C293 S)-mutant, which consistently displayed the strongest effects in mimicking highly homocysteinylated-hnRNP-E1, as well as the wild-type-like hnRNP-E1(G292A)-mutant and wild-type hnRNP-E1 (as controls) were selected for additional study.

Up-Regulation of Folate Receptors (FR) and hnRNP-E1 at the Post-Transcriptional Level—

Figures 11A, 11B, 11C, 11D:
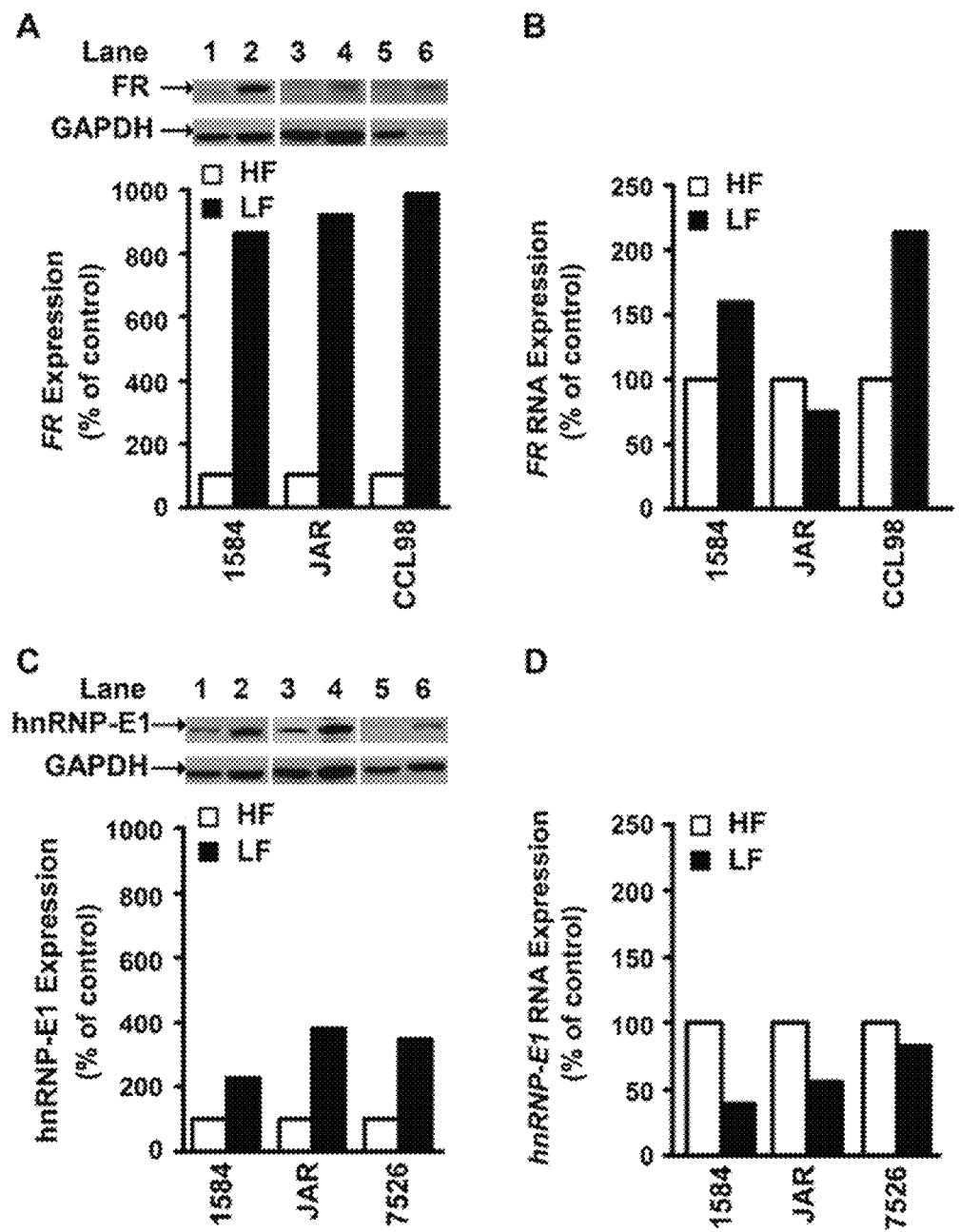
FIGS. 11A-11D depict evidence for increased expression of both folate receptor (FR) and hnRNP-E1 proteins relative to GAPDH from various cultured human placental cells that were propagated long-term in physiologically relevant low-folate (LF) media when compared to cells propagated long-term in high-folate (HF) media. Each of these experiments was repeated twice with comparable results. FR, folate receptor; GAPDH, glyceraldehyde-3-phosphate dehydrogenase.

As shown in FIG. 11A, when compared to folate-replete cells, analysis of 3 folate-deficient placental cell lines (1584, JAR, CCL98) revealed a marked increase in FR when measured by Western blots using anti-folate receptor antiserum and densitometric analysis of the protein signals. Quantitative real-time RT-PCR (qRT-PCR) measurement of folate receptor-$\alpha$ mRNA expression revealed a 1.5- and 2-fold increase in mRNA in 1584 and CCL98 cells, respectively, whereas placental JAR cells contained a lower folate receptor-$\alpha$ mRNA content compared to control cells (FIG. 11B). However, when compared to the extent of folate receptor protein up-regulated in low-folate cells, the net increase in folate receptor-$\alpha$ mRNA in 1584 and CCL98 cells was not proportionately increased when compared to the extent of protein up-regulated; this suggested that the up-regulation of folate receptors occurred at the post-transcriptional level in all three placental cell lines studied. When the expression of hnRNP protein and mRNA in these cells was similarly compared, there was a 2-4 fold increase in hnRNP-E1 protein but hnRNP-E1 mRNA was reduced in all three placental cell lines (FIGS. 11C-11D). These results were similar to that found with folate receptors, and suggested that the up-regulation of hnRNP-E1 in all three folate-deficient placental cell lines was also occurring at the translational level. Because there was evidence of predominantly post-transcriptional up-regulation in placental 1584 cells, we used this cell to further characterize the up-regulation of hnRNP-E1 under folate-deficient conditions.

Comparison of Placentas on Gestation Day 17 in Dams Fed a Folate-Replete Versus a Folate-Deficient Diet—

Because there was up-regulation of folate receptors and hnRNP-E1 in trophoblast-derived placental cell lines, we evaluated if there was similar up-regulation of these proteins in the placentas of dams experiencing gestational folate deficiency. Dams were fed a folate-replete diet (1200-nmol folate/kg diet) or folate-deficient diet (400-nmol folate/kg diet) for 2 months before and during gestation, and on gestation day 17 placentas were evaluated by hematoxylin-eosin (H&E) staining (FIGS. 12A-12D). When the morphology of the placentas (folate-replete (left), versus folate-deficient (right)) was compared on low power (×2.5) magnification (FIG. 12A versus FIG. 12B), there were significant morphological changes in folate-deficient placentas that precluded comparisons to folate-replete placentas. For example, the maternal decidual zone appeared narrowed: this zone is where the giant trophoblastic cells that are involved in initial invasion into the maternal uterus are located; the fate of these cells in folate-deficient placentas was unclear. Moreover, the junctional zone adjacent to the maternal decidual basalis layer contained hyaline changes reflected by the homogeneous, glassy, pink appearance that reflects a major alteration in cell morphology (red arrow). This junctional zone, which is normally composed of fetal spongiotrophoblasts and trophoblast glycogen cells, was disorganized with large sections possibly having been extruded/migrated into the labyrinthine zone; (i.e., in FIG. 11B, note several scattered islands of blue cells within a general background of pink in the labyrinthine zone). There were also significant quantitative changes in that the trophoblast glycogen cells were markedly increased. Whether fetal spongiotrophoblastic cells are lost or differentiated into these trophoblast glycogen cells was unclear; these cells stained well with Periodic Acid Schiff (PAS) reagent and specific anti-glycogen synthase antiserum (not shown). Finally, there were major differences in the labyrinthine zone: this is the zone where the maternal blood space is separated from fetal capillaries by the interhemal membrane and where nutrient and gas exchange occurs. This labyrinthine zone is normally composed of syncytiotrophoblastic and cytotrophoblastic cells—which are rich in folate receptors and hnRNP-E1—are located in the interhemal membrane and are the origin of traditional placental cell lines. Even on low power magnification, this area in folate-deficient placentas appeared to be stained more in pink color, suggesting that there were more red blood cells (erythrocytes) per unit when compared to a comparable area in placentas from folate-replete dams.

Figures 12A, 12B, 12C, 12D:
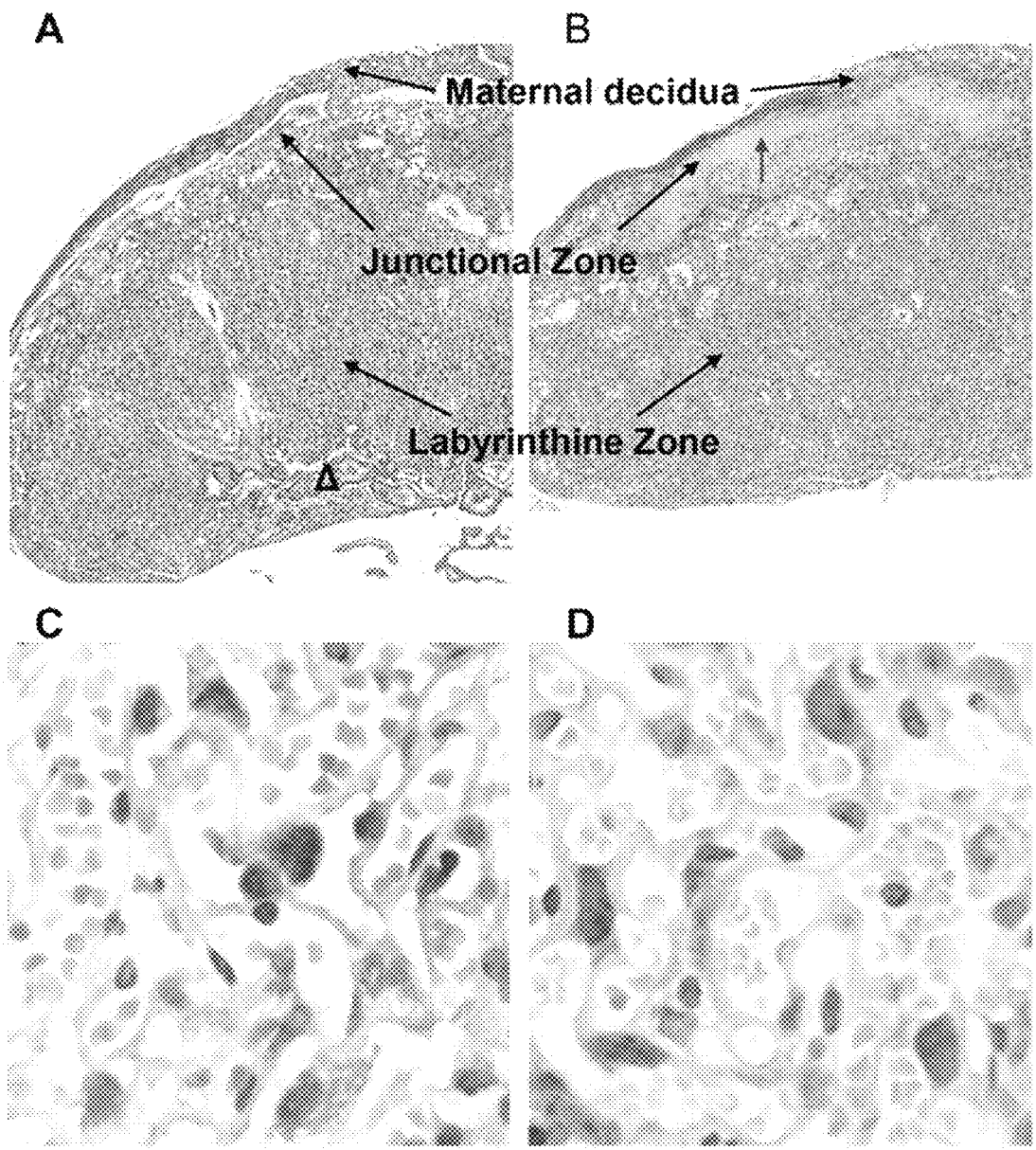
FIGS. 12A-12D show a low power magnification (×2.5) view of hematoxylin-eosin (H&E) stained murine placentas on gestation day 17 from dams fed a folate-replete 1200 nmol folate/kg diet (A) or folate-deficient 400 nmol folate/kg diet (B) for 2 months before and throughout gestation. (C, D) Higher power magnification (×100) of the labyrinth from placentas of folate-replete mice (C) and folate-deficient mice (D). The red arrow points to the junctional zone, just below the maternal decidual basalis layer, which contains a homogeneous, glassy, pink appearance that reflects a major alteration in cell morphology.
Figures 13A, 13B, 13C, 13D:
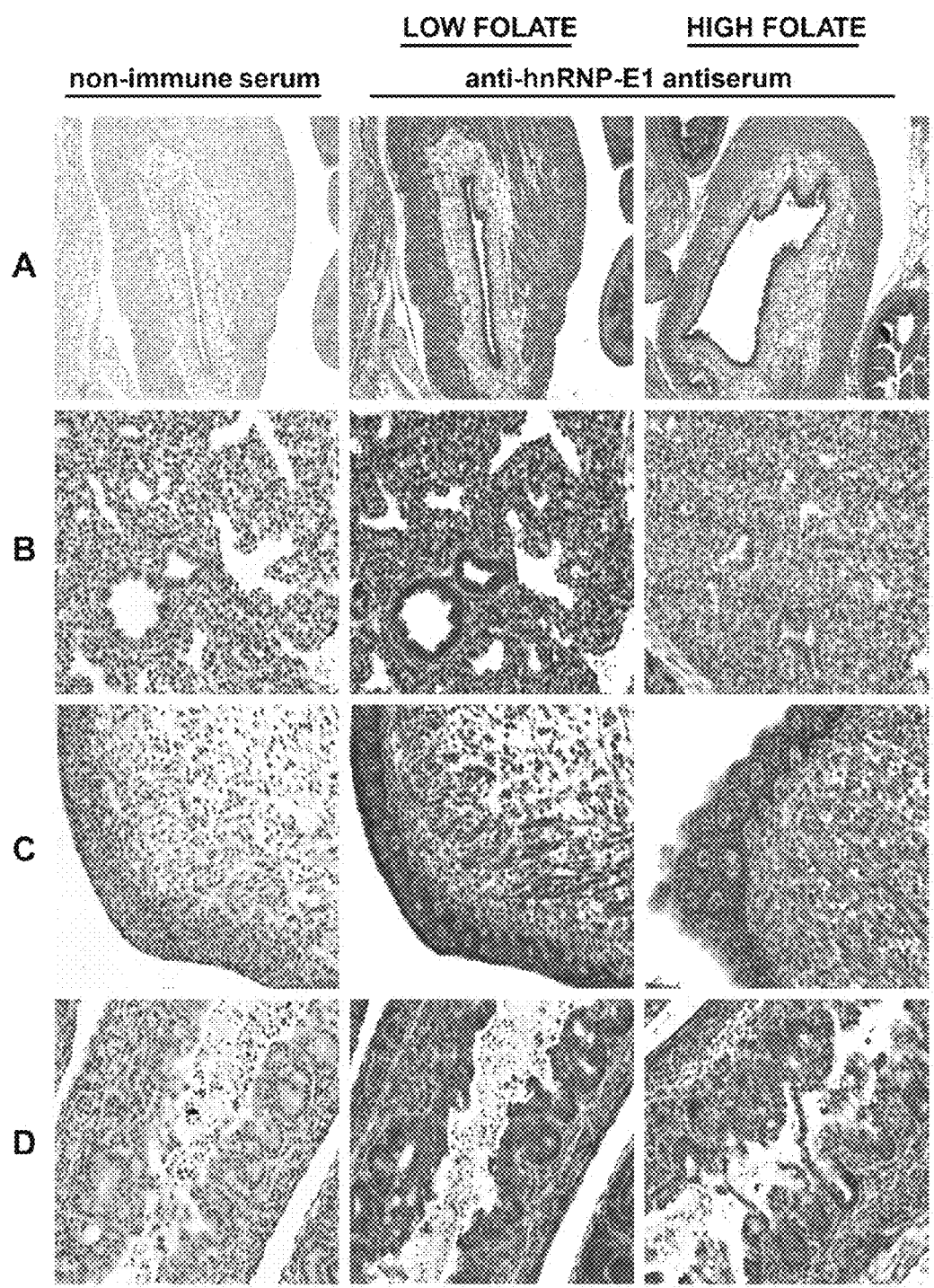
FIGS. 13A-13D show immunohistochemical analysis to demonstrate selective up-regulation of hnRNP-E1 in various tissues of the urinary bladder (A), lung (B), tip of tongue (C), and rectum (D) of gestation day 17 murine fetuses of dams that experienced gestational folate deficiency. Immunohistochemistry using non immune (left panels) or immune anti-hnRNP-E1 antiserum (middle and right panels) to evaluate the expression of hnRNP-E1 from various tissues from selected organs from gestation day 17 fetuses of dams that were fed either 400-nmol folate/kg-diet (middle panel) or 1200-nmol folate/kg-diet (right panel) for two months prior to gestation and throughout gestation. Because of prohibitive costs, this experiment was conducted only once with 10 dams in each dietary cohort. Magnification was ×10 for Panel A representing urinary bladder. Magnification was ×40 for Panels B-D representing lung, tip of tongue, and rectum.

When cells in this zone were counted per frame (see high power magnification ×100; FIG. 12C versus FIG. 12D), the folate-replete placental frame on the left contained 43 trophoblastic cells with nuclei; however, there were only 34 trophoblastic cells with nuclei in a comparable frame on the right from a folate-deficient placenta, and many of these cells had megaloblastic nuclei. Because of the apparent loss of trophoblastic cells, this frame on right contained twice the number of erythrocytes; data from 5 different high power magnification frames revealed that folate-deficient placenta had 108±11 erythrocytes/high power field whereas folate-replete placentas contained 54±7 erythrocytes per high power field (mean±SD; P<0.002). Thus, the finding of more erythrocytes in the labyrinthine zone of placentas from folate-deficient mice nicely explained the basis for the generally greater pink coloring of this zone in lower power magnification of placental sections on H&E staining. We had observed similar findings in the fetal cells from several tissues in our gestational folate-deficient model which was reflected by our detection of "footprints of recent apoptosis" using specific antibodies to caspase-cleaved cytokeratin 18. Thus, the loss of syncytio-trophoblastic/cytotrophoblastic cells in the placentas from folate-deficient dams was likely due to increased apoptosis of these megaloblastic cells during prolonged folate deficiency; this can also explain the finding of more erythrocytes in the labyrinthine zone in folate-deficient placentas on gestation day 17. The normal architecture in folate-replete placentas, which contained many well-formed blood vessels (marked with an open triangle in FIG. 12A), is also lost in folate-deficient placentas, probably a result of apoptosis. Because of these morphological changes—that resulted from eventual apoptosis of severely folate-deficient trophoblastic cells that experienced sustained megaloblastosis—it was not meaningful to directly compare the expression of folate receptors or hnRNP-E1 of placentas from folate-replete and folate-deficient dams.

Evidence for Up-Regulation of hnRNP-E1 in Fetal Tissues of Dams that Experienced Gestational Folate Deficiency—

Earlier we noted a general concordance in expression of folate receptor-α and hnRNP-E1 in several human and murine organs. However, there were several cells within fetal murine organs that failed to exhibit up-regulation of folate receptors under low-folate conditions even though there was expression of hnRNP-E1 in other cells. This discordance was attributable to apoptosis among severely folate-deficient cells, which led to multiple aberrations in fetal tissues—including subtle architectural anomalies and premature differentiation. Accordingly, to determine if there was evidence for selective up-regulation of hnRNP-E1 during folate deficiency within certain tissues of the same organ, we re-evaluated genitourinary, pulmonary, and gastrointestinal organs from gestation day 17 fetuses of dams that were either folate-replete or folate-deficient. Because severe dietary folate restriction led to a profound reduction in viable progeny, 400-nmol folate/kg of diet was deemed a less stringent diet than that employed with tumor xenografts. This approach resulted in serum homocysteine values for folate-replete dams of 19-µM, whereas the serum homocysteine from folate-deficient dams was 77-µM (P<0.05), consistent with levels observed with moderate-to-severe clinical folate deficiency. As shown in FIGS. 13A-13D, each of the fetal tissues studied (bladder (A), lung (B), tip of tongue (C), and rectum (D)) from dams fed low-folate diets composed of 400-nmol folate/kg diet (middle panels) exhibited selective overexpression of hnRNP-E1 in several endodermal, mesodermal, and ectodermal layers of these organs when compared with similar tissues from dams fed high-folate composed of 1200 nmol folate/kg diet (right panels). Thus, during gestational folate deficiency of dams, there was selective up-regulation of hnRNP-E1 within various tissues of the same organ of the fetus, which involved this specific RNA-protein interaction.

Discussion

Perpetuation of hnRNP-E1 Biosynthesis During Folate Deficiency at the Translational Level.

Figure 8:
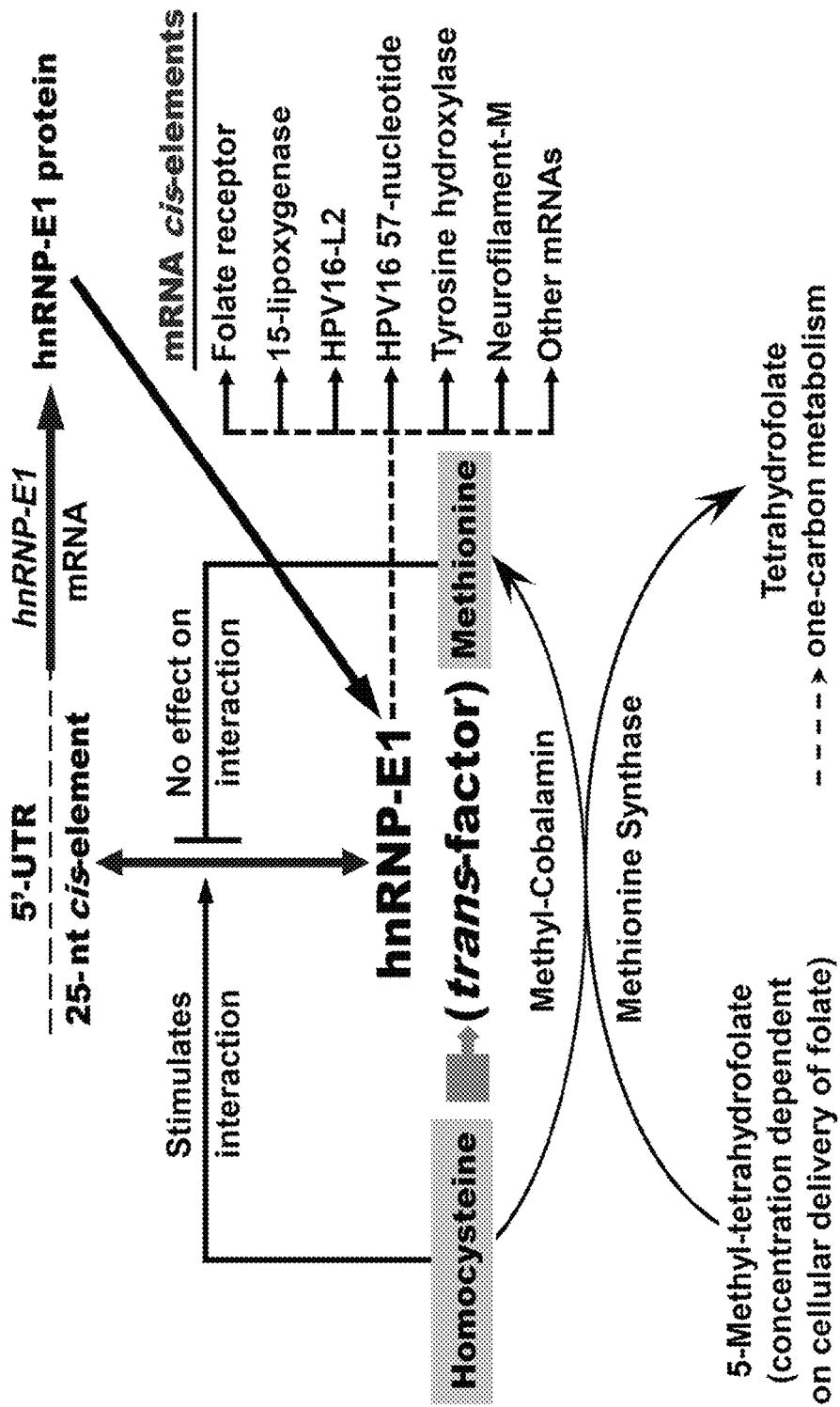
FIG. 8 depicts a model for the interaction between the 25-nt hnRNP-E1 mRNA cis-element and homocysteinylated-hnRNP-E1, which amplifies hnRNP-E1 (and thereby facilitates ongoing up-regulation of folate receptors during prolonged folate deficiency). The cellular accumulation of homocysteine during folate deficiency results in homocysteinylation of hnRNP-E1 (short broad arrow), which unmasks a high affinity mRNA-binding site for target mRNAs. In case of the interaction of homocysteinylated-hnRNP-E1 with its own 25-nt hnRNP-E1 mRNA cis-element, this positive-feedback loop will continue to generate more hnRNP-E1, resulting in amplification of hnRNP-E1. In this model, only folate replenishment can reduce cellular homocysteine levels to a basal state that will turn off this auto-regulatory positive feedback loop involving hnRNP-E1. The mRNA-binding site in homocysteinylated-hnRNP-E1 also accommodates several diverse mRNAs (some of these are identified as 'mRNA cis-elements'). The interaction with these and other mRNA members of the nutrition-sensitive post-transcriptional RNA operon with homocysteinylated-hnRNP-E1 will result in either up- or down-regulation of these mRNA-encoded proteins, many of which may contribute to the cellular features observed in folate-deficient megaloblastic cells. The effect of iron(II) on hnRNP-E1 and other enzyme pathways leading to the intracellular accumulation of L-homocysteine are not shown. HPV16, Human Papillomavirus type 16; HPV16 L2, Human Papillomavirus type 16; HPV16 L2 minor viral capsid protein; HPV16 57-nucleotide, HPV16 57-nucleotide poly (U)-rich cis-element in the early polyadenylation element (upstream of L2^L1 genes); Neurofilament-M, Neuronal intermediate neurofilament-middle molecular mass; 5'-UTR, 5'-untranslated region.

The data provided herein provides support for a model that invokes physiological auto up-regulation of hnRNP-E1 by homocysteinylated-hnRNP-E1 during prolonged folate deficiency (FIG. 8). Thus, during folate deficiency, with an intracellular accumulation of L-homocysteine, the high affinity interaction of intracellular homocysteinylated-hnRNP-E1 with a 25-nt cis-element in the 5'-UTR of hnRNP-E1 mRNA triggers an increase in biosynthesis of hnRNP-E1, which results in up-regulation of hnRNP-E1 proteins. With ongoing folate deficiency, newly synthesized hnRNP-E1 would also become homocysteinylated and perpetuate a positive-feedback loop, which generates hnRNP-E1 (and folate receptors) for as long as folate deficiency persists (FIG. 8). This amplified and homocysteinylated-hnRNP-E1 will also interact (with varying degrees of affinity) with other mRNA members of the nutrition-sensitive folate-responsive post-transcriptional RNA operon during folate deficiency. Because this interaction is sensitive to low concentrations of L-homocysteine, even the small amount of hnRNP-E1 generated during mild folate deficiency could become homocysteinylated and trigger the translation of additional hnRNP-E1, leading to amplification of this circuit, akin to a 'snowball effect' (FIG. 8). Conversely, relief of folate deficiency will turn off this positive feedback loop by reactivating one-carbon metabolism and reducing cellular homocysteine levels via conversion to methionine, which has no effect on the RNA-protein interaction (FIG. 8). Meanwhile, the residual homocysteinylated-hnRNP-E1 will eventually be degraded while constitutive biosynthesis of hnRNP-E1 is re-established. This post-transcriptional up-regulation of hnRNP-E1 during folate deficiency occurs similar to the physiological up-regulation of folate receptors. Therefore, hnRNP-E1 mRNA is yet another member of this post-transcriptional RNA operon that is orchestrated by homocysteinylated-hnRNP-E1 during folate deficiency.

Although the finding of hnRNP-E1 interacting with its own mRNA cis-element under physiological conditions has not been reported, Waggoner and Liebhaber earlier noted that αCP2 (also known as hnRNP-E2) mRNA was associated with specifically-immunoprecipitated αCP2/hnRNP-E2. However, despite their prescient suggestion of possible "autoregulatory control of αCP2 expression", no formal studies had investigated the physiological basis for this interaction, particularly as it relates to nutrition. Our data provides a physiological context for specific interaction between homocysteinylated-hnRNP-E1 and its own 25-nt hnRNP-E1 mRNA cis-element.

Earlier we determined that among the various physiologically relevant thiols, hnRNP-E1 activation and mRNA-binding was optimal with L-homocysteine, but far less with DL-homocysteine, homocysteine thiolactone, L-cysteine, and glutathione; however, D-homocysteine and methionine did not have any effect in triggering this RNA-protein interaction involving hnRNP-E1 binding to folate receptor mRNA and hnRNP-E1 mRNA cis-element, as well as other known target cis-elements. Based on these considerations, it is biologically plausible that other vitamin deficiencies (of Vitamin-$B_{12}$ and Vitamin-$B_6$) and other genetic defects in folate and cobalamin metabolism, which likewise result in accumulation of this thiol intracellularly, would also result in homocysteinylation and activation of hnRNP-E1 to interact with its target RNA cis-elements as a collateral but secondary effect, as discussed earlier. This warrants additional study in animal models.

Although in vitro assays using purified components reveal that RNA-protein interaction can occur with as low as 2.5-μM of L-homocysteine, the precise concentration of free intracellular homocysteine that can trigger interaction of hnRNP-E1 with target mRNA during mild-, moderate-, and severe-folate deficiency is not known. The current state-of-the-art assay for measuring homocysteine in biological specimens detects the sum of all free and protein-bound homocysteine; so that the fraction of free homocysteine—and other thiols—that can react within hnRNP-E1 in cells remain to be determined. Moreover, distinguishing between that fraction of (activated) homocysteinylated-hnRNP-E1 and unmodified-hnRNP-E1 in cells at different degrees of folate deficiency awaits additional refinement in separation of these fractions.

There is some evidence for a potential (but albeit minor) role of hnRNP-E1 in transcription of folate receptor. However, because Mayanil's laboratory has determined that the folate receptor itself is a transcription factor, and amplification of hnRNP-E1 during prolonged folate deficiency impacts on the up-regulation of folate receptors, it will be of interest to identify the entire repertoire of downstream genes that are independently transcribed by hnRNP-E1 and folate receptors during folate deficiency.

Because homocysteine that accumulates in cells leaks out and median values for elevation of serum homocysteine among several cohorts with clinical folate and vitamin-$B_{12}$ deficiency is ~50-μM and ~70-μM, respectively, such concentrations are capable of homocysteinylation of intracellular hnRNP-E1 and triggering high affinity RNA-protein interactions in vivo. This predicts up-regulation of hnRNP-E1 and post-transcriptional engagement of mRNAs comprising its posttranscriptional RNA operon in both Vitamin-B12 and folate deficiency. Indeed, the common clinical hematological manifestations of folate and Vitamin-B12 deficiency likely involve contributions from this nutrition-sensitive posttranscriptional RNA operon.

Our data on the up-regulation of folate receptors in HeLa-$IU_1$-derived tumors growing in folate-deficient mice is consistent with the studies by Leamon et al. However, our findings that the dual up-regulation of folate receptors and hnRNP-E1 likely occurred at the post-transcriptional level in both placental cells and tumor xenografts in response to folate deficiency suggested that endogenous homocysteinylated-hnRNP-E1 likely bound to two distinct mRNA cis-elements in the same tissue. This was corroborated by experiments involving the modulation of hnRNP-E1 within folate-replete placental cells using siRNA against hnRNP-E1 mRNA and (HA)-hnRNP-E1 (C293S)-mutant proteins. These results can now explain the constitutive co-expression of these two proteins in several human tissues such as placenta, cervical, reticulocytes and erythroid precursors, as well as in several murine fetal tissues of dams that experienced gestational folate deficiency. Although homogeneous populations of tumor xenografts had uniform up-regulation of hnRNP-E1 in response to folate deficiency, there was selective expression of hnRNP-E1 in heterogeneous tissues among different organs from murine fetuses that experienced folate deficiency in utero (FIGS. 13A-13D). Future experiments will need to clarify the basis for these selective transcriptional and/or post-transcriptional events that contributed to these observations.

Effect of Iron(II) in Modulating the RNA-Protein Interaction.

While hnRNP-E1 (also known as poly(rC)-binding protein-1; PCBP1) is a cellular sensor of folate deficiency, it is also an iron-binding protein that is believed to chaperone cytosolic iron to ferritin. Although both cysteine and glutathione are candidate ligands for the cytosolic labile iron pool, and bind iron(II) with high affinity, the much higher physiological concentration of glutathione (10-mM) when compared to cysteine (less than 0.5-mM) will dominate binding of iron. Indeed, Hider and Kong suggested that the major component of the labile iron pool in the cytosol is the simple glutathione-iron(II) complex, Fe(II)GS, and that this complex will dominate the speciation of iron(II) over cellular iron(II) concentrations of $10^{-7}$ to $10^{-5}$. We observed that in the presence of a fixed concentration of L-homocysteine that triggered homocysteinylated-hnRNP-E1 binding to hnRNP-E1 mRNA cis-element, there was a specific dose-dependent effect of iron(II) in quenching this interaction. Although iron(III) alone had no effect in modulating RNA-protein complex formation, when iron(III) was rapidly reduced to iron(II) by 10-mM glutathione, there was a similar specific effect as iron(II) in reducing the interaction of homocysteinylated-hnRNP-E1 with hnRNP-E1 mRNA cis-element. The molecular basis for the effect of iron(II) and Fe(II)GS on hnRNP-E1 remains to be clarified.

Despite these findings, it remains unclear if these effects of the addition of iron(II) evoked experimentally using purified components are biologically relevant in iron-replete cells. This is because all our previous studies involving hnRNP-E1 that documented significant post-transcriptional up-regulation of folate receptors in cells, and up-regulation of hnRNP-E1 in murine fetuses of dams that experienced gestational folate deficiency, as well as in cultured placental cells and xenografts in mice, were conducted under conditions with sufficient iron(II) present. However, a more plausible and clinically relevant scenario in which a role of iron(II) can be better appreciated is during combined iron- and folate-deficiency, which is found in well over one-half of pregnant women in resource-limited countries. In such a scenario, the reduced intracellular availability of iron(II) to interact with hnRNP-E1 would be permissive in facilitating the capacity of L-homocysteine to covalently bind to hnRNP-E1 and unmask its mRNA-binding site, leading to increased binding affinity for target mRNA (FIG. 8). Therefore, the net effects of iron(II) deficiency—when superimposed on a given degree of folate deficiency—could be to further enhance the engagement of member mRNAs (of the nutrition-sensitive post-transcriptional RNA operon) by homocysteinylated-hnRNP-E1; this could lead to even more adverse effects when compared to the effects of pure folate deficiency—(i.e., iron deficiency has potential to magnify the adverse effects of folate deficiency). This hypothesis warrants further testing in vivo in animals with combined folate and iron deficiency, particularly because of its potential relevance to fetal neurodevelopment. For example, we documented a dose-dependent interaction of homocysteinylated-hnRNP-E1 with tyrosine hydroxylase- and neuronal intermediate neurofilament-middle molecular mass (neurofilament-M)-mRNAs, which was associated with overexpression of tyrosine hydroxylase- and neurofilament-M proteins, respectively, in the brains of murine fetuses that experienced folate deficiency. Therefore, in a fetus that experiences combined iron- and folate-deficiency, the augmented interaction of homocysteinylated-hnRNP-E1 with tyrosine hydroxylase mRNA could lead to an even greater overexpression of tyrosine hydroxylase and predispose to increased biosynthesis of neurotransmitters (dopamine and norepinephrine). Likewise, the augmented interaction with neurofilament-M mRNA leading to greater overexpression of neurofilament-M could further perturb its delicately balanced synthesis with neurofilament low- and high-molecular mass triplet proteins, resulting in abnormal intermediate filaments and disturbed formation of neurons. Thus, assessing how the superimposition of iron deficiency to folate deficiency can further worsen the already disordered histopathology in the brains of mouse fetuses that experienced folate deficiency in utero, and studying how these dual deficiencies can further modulate their postnatal anxiety phenotype, warrant further investigation. This is particularly relevant because of (i), the recent burgeoning literature pointing to clinical correlates of our murine studies, where women with dietary insufficiency of folate during pregnancy appear to have a higher risk of bearing children with neuropsychiatric and/or behavioral problems, and (ii), the widespread acknowledgment of the critical role of iron during human neurodevelopment.

The Spectrum of mRNAs Bound by hnRNP-E1 During Folate Deficiency.

Although the precise number of mRNAs that can interact with homocysteinylated-hnRNP-E1 is unclear, earlier studies demonstrated 160 mRNAs that interact with the closely related protein, αCP2 (hnRNP-E2) in a human hematopoietic cell line. These mRNAs encoded a plethora of cellular proteins, including those related to components of the cytoskeleton, transcription factors, proto-oncogenes, factors involved in cell signaling, constituents of hemoglobin, cell proliferation, differentiation and apoptosis. Because of significant homology in the KH domains of hnRNP-E2 and hnRNP-E1, such data predict that the mRNA-binding domain of hnRNP-E1 will also interact with a comparably large number of mRNAs. Indeed, several other studies indicate that hnRNP-E1 interacts with mRNAs involved in cell differentiation, viral mRNAs, neurotransmitters, nerve and neuronal cell components, and cell cycle proteins. Parenthetically, in every instance where hnRNP-E1 binds these various mRNA in the presence of non-physiological reducing agents such as DTT and ß-ME, there is also an interaction with the physiologically relevant reducing agent, L-homocysteine. So it is clearly important to identify the entire spectrum of mRNA members of this post-transcriptional RNA operon that interact with homocysteinylated-hnRNP-E1. Another challenge from a pathobiological standpoint is to identify the rank-order and temporal sequence of binding of these diverse mRNAs to hnRNP-E1 as it is progressively homocysteinylated during mild-, moderate-, and severe-clinical folate deficiency. This is because the net effects of up- and down-regulation of the proteins encoded by the many different mRNAs belonging to this operon are likely to influence several aspects of the cellular pathobiology of evolving megaloblastic changes during progressive folate deficiency.

Potential Clinical Consequences of Perturbed RNA-Protein Interactions.

Subtle mutations among several members of the hnRNP family have given rise to diverse clinical syndromes. This includes Fragile X syndrome arising from mutations in the Fragile X mental retardation 1 (FMR1) gene on the X chromosome, results in a failure to express the fragile X mental retardation protein that is required for normal neural development. Other paraneoplastic neurologic disorders involving antibodies directed against one member of the hnRNP family, Nova-1, trigger the clinical syndrome of paraneoplastic opsoclonus myoclonus ataxia, whereas antibodies to another member, Hu neuronal antigen, induce the subacute sensory neuropathy/encephalomyelopathy syndrome. Thus, in analogy, our data suggests that it is possible for single nucleotide mutations in either the hnRNP-E1 mRNA cis-element or the hnRNP-E1 protein to profoundly perturb physiological RNA-protein interaction and result in novel clinical syndromes. For example, mutations in the first and/or third CUCC motif of the 25-nt hnRNP-E1 mRNA cis-element would reduce or abolish interaction with hnRNP-E1 (FIG. 4A-4D). Conversely, mutation of a single cysteine among several potential cysteine residues in hnRNP-E1 (FIGS. 10A-10H) that leads to a (HA)-hnRNP-E1(C293 S)-like mutant has potential to markedly increase interaction with operon-associated mRNAs. Such mutations could give rise to profoundly distinct clinical syndromes that arise from quantitatively different and/or opposing expression of key proteins encoded by mRNAs that belong to the post-transcriptional RNA operon controlled by hnRNP-E1. Therefore experimental studies in animals bearing such mutations could provide clues to clinical syndromes in humans for which the genetic basis has remained obscure.

Finally, the putative homocysteinylation of other members of the hnRNP-family, which are closely related to hnRNP-E1 (such as hnRNP-E2, and Nova-1, among others), could result in the activation of a coordinated network of post-transcriptional RNA operons that together comprise a higher-order, nutrition-sensitive, folate-responsive, post-transcriptional RNA regulon. In such a construct, the degree to which the mRNA-binding site in each related hnRNP protein is unmasked by homocysteinylation will dictate the extent of its participation in such a putative regulon. In this context, the profound pathophysiological changes observed in the murine fetal brain that experienced folate deficiency, as well as the postnatal behavioral features of anxiety, could well have arisen from activation of more than one of these putatively homocysteinylated-hnRNP family members in utero.

Molecular Mimics of Homocysteinylated-hnRNP-E1—

Our previous studies predicted that with increasing degrees of folate deficiency, the sequential homocysteinylation of accessible cysteine residues on hnRNP-E1, involving the replacement of key cysteine-S-S-cysteine disulfide bonds by homocysteine-S-S-cysteine mixed disulfide bonds, would lead to a progressive unmasking of the underlying mRNA-binding site in homocysteinylated-hnRNP-E1. Therefore, by systematically substituting individual cysteine residues in hnRNP-E1, we determined that the highest affinity (HA)-hnRNP-E1(C293S)-mutant, involving substitution of the only cysteine residue (Cys-293) in the KH3 domain of hnRNP-E1 by serine, possessed the highest mRNA-binding affinity among the pool of hnRNP-E1 mutants generated. In earlier studies, the incubation of purified recombinant hnRNP-E1 and folate receptor-α mRNA cis-element with progressively increasing concentrations of L-homocysteine—from physiological levels through those associated with mild-to-moderate folate deficiency—led to proportionately greater affinities of hnRNP-E1 for the target mRNA cis-element (i.e., baseline $K_D$ of 1.5 nM increasing to $K_D$ of 0.5 nM). Similar to homocysteinylated-hnRNP-E1, but now in the absence of L-homocysteine in the reaction mixture, the (HA)-hnRNP-E1(C293 S)-mutant consistently demonstrated a $K_D$ of 0.2 nM when compared to the $K_D$ of 1.5 nM found in the wild-type-like hnRNP-E1(G292A)-mutant (control). This (HA)-hnRNP-E1(C293 S)-mutant protein also specifically triggered the biosynthesis of folate receptors, and like homocysteinylated-hnRNP-E1, also bound with high affinity to HPV16 L2 mRNA cis-element and reduced its translation in vitro. Thus, there was internal consistency and concordance in dissociation constant values between homocysteinylated-hnRNP-E1 and the (HA)-hnRNP-E1(C293S)-mutant, which rivaled the highest affinity form of homocysteinylated-hnRNP-E1 (found in moderately severe folate deficiency). This (HA)-hnRNP-E1(C293S)-mutant protein was also functional shortly after liposome-mediated transfection into placental 1584-HF cells, as indicated by a significant increase in stimulation of the biosynthesis of newly synthesized [$^{35}$S] folate receptors and [$^{35}$S]hnRNP-E1, respectively (Table 8, main text). These mutation studies suggested that the status of the Cys-293 sulfhydryl group in hnRNP-E1 is critical for controlling access to the mRNA-binding site in the native protein. Therefore, upon formation of a protein-cysteine-S-S-homocysteine mixed disulfide bond at Cys-293, the underlying mRNA-binding site in hnRNP-E1 is fully opened and can then bind several other mRNA members of this nutrition-sensitive post-transcriptional RNA operon. In this context, our data on the capacity of different hnRNP-E1-mutants to give rise to RNA-protein signals of varying intensity, which predicts different degrees of affinity, suggests that a progressive homocysteinylation of cysteine-S-S-cysteine bonds that leads to the gradual unmasking of the underlying mRNA-binding site in hnRNP-E1 will occur during mild-, moderate-, and severe-folate deficiency. This is an area for future investigation.

Earlier, we showed that incubation of purified recombinant hnRNP-E1 with L-homocysteine followed by cleavage and analysis of tryptic peptides by nano-LC-MS/MS identified several homocysteine-S-S-cysteine mixed disulfide bonds that were located in both the KH1 and KH2 domain. Therefore, it was not surprising that mutagenesis of cysteine residues in the KH1 and KH2 domains also conferred a 'high affinity-hnRNP' status to the mutant proteins (in that they did not require homocysteine or other reducing agents for binding mRNA). However, the very high affinity exhibited by the (HA)-hnRNP hnRNP-E1(C293S)-mutant for a variety of cognate mRNAs belonging to the nutrition-sensitive operon that can interact with homocysteinylated-hnRNP-E1 was unexpected. This is because our previous studies did not identify the involvement of cysteine-293 as binding to L-homocysteine in a protein-cysteine-S-S-homocysteine mixed disulfide bond. Since trypsin cleaves exclusively C-terminal to arginine and lysine residues, Cys-293 could have been recovered within a 29 amino acid sequence fragment (after the Lys-268 and ending in Arg-297) from a mixture of tryptic peptides. Although a lower relative ionization efficiency that precluded detection by nano-LC-MS/MS is possible, we did not pursue specific experiments to determine the reason why this peptide was not detected earlier. Nevertheless, previous crystallization studies on the KH3 domain of hnRNP-E1/αCP1 had incriminated Cys-293 as one among several amino acids that participated in binding poly(rC)-rich sequences. For example, the amino acid sequence within the KH3 domain of hnRNP-E1 (IGCI IGRQGANINEIR, SEQ ID NO:32) predicted to make contact with a target oligonucleotide is underlined; however, there is no information on the accessibility of Cys-293 for homocysteinylation in the native protein. Therefore, focused studies on the sequence of progressive homocysteinylation of cysteine residues in this protein in vivo are warranted.

Table 1:

Comparison of the dissociation constant ($K_D$) of the interaction of recombinant purified GST-hnRNP-E1 or its mutant protein for the [$^{35}$S]25-nt hnRNP-E1 mRNA cis-element in the absence or presence of L-homocysteine. The results are presented as mean±SD, n=3 (means of triplicates). Labeled means without a common letter differ, P<0.05.

TABLE 1

Comparison of the dissociation constant ($K_D$) of the interaction of recombinant purified GST-hnRNP-E1 or its mutant protein for the [$^{35}$S]25-nt hnRNP-E1 mRNA cis-element in the absence or presence of L-homocysteine.

| Protein | L-Homocysteine (μM) | $K_D$ (nM) |
|---|---|---|
| GST-hnRNP-E1 | 0 | 1.93 ± 0.18 a |
| GST-hnRNP-E1 | 10 | 1.14 ± 0.17 b |
| GST-hnRNP-E1 | 50 | 0.62 ± 0.10 c |
| GST-hnRNP-E1(G292A) | 0 | 2.02 ± 0.19 a |
| GST-hnRNP-E1(C293S) | 0 | 0.39 ± 0.04 d |

The results are presented as mean ± SD, n = 3 (means of triplicates). Labeled means without a common letter differ, P < 0.05.

Table 2:

Comparison of the dissociation constant ($K_D$) of the interaction of recombinant purified GST-hnRNP-E1 or its mutant protein for the [$^{35}$S] 18-nt folate receptor-α mRNA cis-element in the absence or presence of L-homocysteine. The results are presented as mean±SD, n=3 (means of triplicates). Labeled means without a common letter differ, P<0.05.

TABLE 2

Comparison of the dissociation constant ($K_D$) of the interaction of recombinant purified GST-hnRNP-E1 or its mutant protein for the [$^{35}$S]18-nt folate receptor-α mRNA cis-element in the absence or presence of L-homocysteine.

| Protein | L-Homocysteine (μM) | $K_D$ (nM) |
|---|---|---|
| GST-hnRNP-E1 | 0 | 1.47 ± 0.16 a |
| GST-hnRNP-E1 | 10 | 0.89 ± 0.16 b |
| GST-hnRNP-E1 | 50 | 0.47 ± 0.09 c |
| GST-hnRNP-E1(G292A) | 0 | 1.57 ± 0.16 a |
| GST-hnRNP-E1(C293S) | 0 | 0.27 ± 0.04 d |

The results are presented as mean ± SD, n = 3 (means of triplicates). Labeled means without a common letter differ, P < 0.05.

Table 3:

Dissociation constants ($K_D$) of the RNA-protein interaction of [$^{35}$S]25-nt hnRNP-E1 mRNA cis-element and purified recombinant GST-hnRNP-E1 protein in the presence of 10-mM glutathione and 15-μM of either L-homocysteine or L-cysteine. The results are presented as mean±SD, n=3 (means of triplicates). Labeled means without a common letter differ, P<0.05.

TABLE 3

Dissociation constants ($K_D$) of the RNA-protein interaction of [$^{35}$S]25-nt hnRNP-E1 mRNA cis-element and purified recombinant GST-hnRNP-E1 protein in the presence of 10-mM glutathione and 15-μM of either L-homocysteine or L-cysteine.

| Thiol (15 μM) | $K_D$ (nM) |
|---|---|
| L-Homocysteine | 1.18 ± 0.27 a |
| L-Cysteine | 2.38 ± 0.56 b |

The results are presented as mean ± SD, n = 3 (means of triplicates). Labeled means without a common letter differ, P < 0.05.

Table 4:

Concentration of various thiol amino acids in placental 1584-HF cells and 1584-LF cells. The results are presented as mean±SD, n=3 (means of triplicates). Asterisk (*) signifies a value different from control (1584-HF cells), P<0.05.

TABLE 4

Concentration of various thiol amino acids in placental 1584-HF cells and 1584-LF cells.

| Thiol amino acids (μM) | 1584-HF cells | 1584-LF cells |
|---|---|---|
| Homocysteine | 31.9 ± 1.8 | 184.4 ± 1.5 * |
| Cystathionine | 19.4 ± 0.3 | 29.1 ± 0.3 * |
| Cysteine | 327.3 ± 5.2 | 481.2 ± 12.6 * |
| Methionine | 46.7 ± 1.3 | 69.2 ± 1.9 * |

The results are presented as mean ± SD, n = 3 (means of triplicates).
Asterisk (*) signifies a value different from control (1584-HF cells), P < 0.05.

Table 5:

Primer sequences for various point mutations within the 25-nt hnRNP-E1 mRNA cis-element. The EcoR1 restriction enzyme site is gaattc and the HindIII restriction enzyme site is aagctt. The point mutation sites (numbered Mutation 1 to 7) are shown in bold and underline.

Table 6:

Effect of transfection of wild-type-, scrambled-, and antisense-oligonucleotides to the 25-nt hnRNP-E1 mRNA cis-element on the rate of biosynthesis of [$^{35}$S]cysteine-hnRNP-E1 protein in placental 1584-HF cells. The results are presented as mean±SD, n=3 (means of triplicates). Labeled means without a common letter differ, P<0.05.

TABLE 6

Effect of transfection of wild-type-, scrambled-, and antisense-oligonucleotides to the 25-nt hnRNP-E1 mRNA cis-element on the rate of biosynthesis of [$^{35}$S]cysteine-hnRNP-E1 protein in placental 1584-HF cells.

| Oligonucleotide transfected into placental 1584-HF cells | [$^{35}$S]cysteine-hnRNP-E1 protein (fmol/mg protein/h) |
|---|---|
| Wild-type | 1.04 ± 0.02 a |
| Scrambled | 1.01 ± 0.03 a |
| Antisense | 0.62 ± 0.02 b |

The results are presented as mean ± SD, n = 3 (means of triplicates). Labeled means without a common letter differ, P < 0.05.

Table 7:

Evidence for the specificity of RNA interference (RNAi) against hnRNP-E1 mRNA in perturbing the biosynthetic rate of newly synthesized hnRNP-E1 and folate receptor proteins in placental 1584-HF cells. The results are presented as mean±SD, n=3 (means of triplicates). Labeled means without a common letter differ, P<0.05.

TABLE 5

Primer sequences for various point mutations within the 25-nt hnRNP-E1 mRNA cis-element. The EcoR1 restriction enzyme site is gaattc and the HindIII restriction enzyme site is aagctt. The point mutation sites (numbered Mutation 1 to 7) are shown in bold and underline.

|  | PRIMER | SEQUENCE | |
|---|---|---|---|
| Wild-type | Primer-0F | 5'-cacggaattCTCCCGCCCGCTCCCGCTCGCTCCCaagcttgggt-3' | (SEQ ID NO: 56) |
|  | Primer-0R | 5'-acccaagcttGGGAGCGAGCGGGAGCGGGCGGGAgaattccgtg-3' | (SEQ ID NO: 57) |
| Mutation 1 | Primer-1F | 5'-cacggaattCCT<u>T</u>CCGCCCGCTCCCGCTCGCTCCCaagcttgggt-3' | (SEQ ID NO: 58) |
|  | Primer-1R | 5'-acccaagcttGGGAGCGAGCGGGAGCGGGCGG<u>A</u>Agaattccgtg-3' | (SEQ ID NO: 59) |
| Mutation 2 | Primer-2F | 5'-cacggaattCTCCCGCCCGCTT<u>T</u>CCGCTCGCTCCCaagcttgggt-3' | (SEQ ID NO: 60) |
|  | Primer-2R | 5'-acccaagcttGGGAGCGAGCGG<u>A</u>AGCGGGCGGGAgaattccgtg-3' | (SEQ ID NO: 61) |
| Mutation 3 | Primer-3F | 5'-cacggaattCTCCCGCCCGCTCCCGCTCGCTT<u>T</u>CCaagcttgggt-3' | (SEQ ID NO: 62) |
|  | Primer-3R | 5'-acccaagcttGG<u>A</u>AGCGAGCGGGAGCGGGCGGGAgaattccgtg-3' | (SEQ ID NO: 63) |
| Mutation 4 | Primer-4F | 5'-cacggaattCCT<u>T</u>CCGCCCGCTT<u>T</u>CCGCTCGCTCCCaagcttgggt-3' | (SEQ ID NO: 64) |
|  | Primer-4R | 5'-acccaagcttGGGAGCGAGCGG<u>A</u>AGCGGGCGG<u>A</u>Agaattccgtg-3' | (SEQ ID NO: 65) |
| Mutation 5 | Primer-5F | 5'-cacggaattCTCCCGCCCGCTT<u>T</u>CCGCTCGCTT<u>T</u>CCaagcttgggt-3' | (SEQ ID NO: 66) |
|  | Primer-5R | 5'-acccaagcttGG<u>A</u>AGCGAGCGG<u>A</u>AGCGGGCGGGAgaattccgtg-3' | (SEQ ID NO: 67) |
| Mutation 6 | Primer-6F | 5'-cacggaattCCT<u>T</u>CCGCCCGCTCCCGCTCGCTT<u>T</u>CCaagcttgggt-3' | (SEQ ID NO: 68) |
|  | Primer-6R | 5'-acccaagcttGG<u>A</u>AGCGAGCGGGAGCGGGCGG<u>A</u>Agaattccgtg-3' | (SEQ ID NO: 69) |
| Mutation 7 | Primer-7F | 5'-cacggaattCCT<u>T</u>CCGCCCGCTT<u>T</u>CCGCTCGCTT<u>T</u>CCaagcttgggt-3' | (SEQ ID NO: 70) |
|  | Primer-7R | 5'-acccaagcttGG<u>A</u>AGCGAGCGG<u>A</u>AGCGGGCGG<u>A</u>Agaattccgtg-3' | (SEQ ID NO: 71) |

TABLE 7

Evidence for the specificity of RNA interference (RNAi) against hnRNP-E1 mRNA in perturbing the biosynthetic rate of newly synthesized hnRNP-E1 and folate receptor proteins in placental 1584-HF cells.

| RNAi transfected in placental 1584-HF cells | [$^{35}$S]cysteine-hnRNP-E1 (fmol/mg protein/h) | [$^{35}$S]cysteine folate receptor (fmol/mg protein/h) |
|---|---|---|
| Wild-type 25-nt hnRNP-E1 RNA | 1.02 ± 0.07 a | 1.58 ± 0.02 a |
| Scrambled 25-nt RNA | 0.95 ± 0.04 a | 1.57 ± 0.05 a |
| RNAi against 25-nt hnRNP-E1 mRNA | 0.32 ± 0.02 b | 0.35 ± 0.02 b |

The results are presented as mean ± SD, n = 3 (means of triplicates). Labeled means without a common letter differ, P < 0.05.

Table 8:
Effect of the introduction of equivalent amounts of various purified recombinant wild-type- or mutant-GST-hnRNP-E1 proteins into placental 1584-HF cells on the biosynthetic rate of newly synthesized [$^{35}$S]cysteine-hnRNP-E1 and [$^{35}$S]cysteine-folate receptor proteins. The results are presented as mean±SD, n=3 (means of triplicates). Labeled means without a common letter differ, P<0.05.

TABLE 8

Effect of the introduction of equivalent amounts of various purified recombinent wild-type- or mutant-GST-hnRNP-E1 proteins into placental 1584-HF cells on the biosynthetic rate of newly synthesized [$^{35}$S]cysteine-hnRNP-E1 and [$^{35}$S]cysteine-folate receptor proteins.

| Protein transfected in placental 1584-HF cells | [$^{35}$S]cysteine-hnRNP-E1 (fmol/mg protein/h) | [$^{35}$S]cysteine-folate receptor (fmol/mg protein/h) |
|---|---|---|
| No-transfection | 0.53 ± 0.17 a | 0.95 ± 0.12 a |
| GST-hnRNP-E1 | 1.12 ± 0.23 b | 1.62 ± 0.11 b |
| GST-hnRNP-E1(G292A) | 1.03 ± 0.21 b | 1.79 ± 0.13 b |
| GST-hnRNP-E1(C293S) | 6.70 ± 1.74 c | 6.62 ± 0.74 c |

The results are presented as mean ± SD, n = 3 (means of triplicates). Labeled means without a common letter differ, P < 0.05.

Table 9:
Dose-dependent influence of Iron(II) on the dissociation constant ($K_D$) involving the L-homocysteine-triggered RNA-protein interaction between [$^{35}$S]25-nt hnRNP-E1 mRNA cis-element and purified recombinant GST-hnRNP-E1 protein. The results are presented as mean±SD, n=3 (means of triplicates). Labeled means without a common letter differ, P<0.05.

TABLE 9

Dose-dependent influence of Iron(II) on the dissociation constant ($K_D$) involving the L-homocysteine-triggered RNA-protein interaction between [$^{35}$S]25-nt hnRNP-E1 mRNA cis-element and purified recombinent GST-hnRNP-E1 protein.

| Protein | Iron(II) (µM) | L-Homocysteine (µM) | $K_D$ (nM) |
|---|---|---|---|
| GST-hnRNP-E1 | 0 | 25 | 2.74 ± 0.52 a |
| GST-hnRNP-E1 | 5 | 25 | 3.72 ± 0.34 b |
| GST-hnRNP-E1 | 25 | 25 | 6.50 ± 0.83 c |

The results are presented as mean ± SD, n = 3 (means of triplicates). Labeled means without a common letter differ, P < 0.05.

Table 10:
Nucleotide sequences of forward and reverse primers used to generate hnRNP-E1 mutants.

TABLE 10

Nucleotide sequences of forward and reverse primers used to generate hnRNP-E1 mutants.
Primer Sequences for Site-directed Mutagenesis of hnRNP-E1

| Description | Sequence | |
|---|---|---|
| pE1C54S-FWD: | 5'-CATCTCGGAGGGGAATTCTCCGGAGAGAATCATC-3' | (SEQ ID NO: 33) |
| pE1C54S-RVS: | 3'-GTAGAGCCTCCCCTTAAGAGGCCTCTCTTAGTAG-5' | (SEQ ID NO: 34) |
| pE1C109S-FWD: | 5'-GCTCCCCAGTCATCTCCGCGGGCGGCCAAGA-3' | (SEQ ID NO: 35) |
| pE1C109S-RVS: | 3'-CGAGGGGTCAGTAGAGGCGCCCGCCGGTTCT-5' | (SEQ ID NO: 36) |
| pE1C118S-FWD: | 5'-GATTGGGAAAGGCGGGTCTAAGATCAAAGAGATCCG-3' | (SEQ ID NO: 37) |
| pE1C118S-RVS: | 3'-CTAACCCTTTCCGCCCAGATTCTAGTTTCTCTAGGC-5' | (SEQ ID NO: 38) |
| pE1C158S-FWD: | 5'-AGTCTGTCACCGAGTCTGTCAAGCAGATTTG-3' | (SEQ ID NO: 39) |
| pE1C158S-RVS: | 3'-TCAGACAGTGGCTCAGACAGTTCGTCTAAAC-5' | (SEQ ID NO: 40) |
| pE1C163S-FWD: | 5'-GTGTCAAGCAGATTTCCCTGGTCATGCTGGA-3' | (SEQ ID NO: 41) |
| pE1C163S-RVS: | 3'-CACAGTTCGTCTAAAGGGACCAGTACGACCT-5' | (SEQ ID NO: 42) |
| pE1C194S-FWD: | 5'-GCTCCCCAGTCATCTCCGCGGGCGGCCAAGA-3' | (SEQ ID NO: 43) |
| pE1C194S-RVS: | 3'-CGAGGGGTCAGTAGAGGCGCCCGCCGGTTCT-5' | (SEQ ID NO: 44) |
| pE1C201S-FWD: | 5'-GCGGCCAAGATCGGTCCAGCGACGCTGTGGG-3' | (SEQ ID NO: 45) |
| pE1C201S-RVS: | 3'-CGCCGGTTCTAGCCAGGTCGCTGCGACACCC-5' | (SEQ ID NO: 46) |
| pE1C293S-FWD: | 5'-CCAAATAACTTAATTGGCTCCATAATCGGGCGCCAAGG-3' | (SEQ ID NO: 47) |
| pE1C293S-RVS: | 3'-GGTTTATTGAATTAACCGAGGTATTAGCCCGCGGTTCC-5' | (SEQ ID NO: 48) |

TABLE 10-continued

Nucleotide sequences of forward and reverse primers used to generate hnRNP-E1 mutants.
Primer Sequences for Site-directed Mutagenesis of hnRNP-E1

| Description | Sequence | |
|---|---|---|
| pE1C355S-FWD: | 5'-AGAAGGGCATGGGGTCCAGCTAGAACAGTGT-3' | (SEQ ID NO: 49) |
| pE1C355S-RVS: | 3'-TCTTCCCGTACCCCAGGTCGATCTTGTCACA-5' | (SEQ ID NO: 50) |
| pE1G52A-FWD: | 5'-TCAACATCTCGGAGGCGAATTGTCCGGAGAG-3' | (SEQ ID NO: 51) |
| pE1G52A-RVS: | 3'-AGTTGTAGAGCCTCCGCTTAACAGGCCTCTC-5' | (SEQ ID NO: 52) |
| pE1G292A-FWD: | 5'-CAAATAACTTAATTGCCTGCATAATCGGGCG-3' | (SEQ ID NO: 53) |
| pE1G292A-RVS: | 3'-GTTTATTGAATTAACGGACGTATTAGCCCGC-5' | (SEQ ID NO: 54) |

ABBREVIATIONS

The abbreviations used are: anti-hnRNP-E1 Ab, anti-hnRNP-E1 antiserum; ß-ME, ß-mercaptoethanol; CAT, chloramphenicol acetyltransferase; DFO, deferoxamine; FR, (human) folate receptor-α; GAPDH, glyceraldehyde-3-phosphate dehydrogenase; Fe(II)GS, glutathione-iron(II) complex; GST, glutathione S-transferase; hnRNP-E1, heterogeneous nuclear ribonucleoprotein E1; (HA)-hnRNP-E1 (C293 S)-mutant, highest affinity hnRNP-E1(C293 S)-mutant, -HF, high-folate; HPV16, Human Papillomavirus Type 16; Iron(II), ferrous sulfate heptahydrate [$FeSo_4.7H_2O$]; Iron(III), ferric chloride hexahydrate [$FeCl_3.6H_2O$]; KH, K-homology domain; -LF, low-folate; Neurofilament-M, Neuronal intermediate neurofilament-middle molecular mass; PCBP1, poly(rC)-binding protein 1; qRT-PCR, quantitative real-time reverse-transcriptase polymerase chain reaction. 5'-UTR, 5'-untranslated region

REFERENCES

Antony A C, Tang Y S, Khan R A, Biju M P, Xiao X, Li Q J, Sun X L, Jayaram H N, and Stabler S P. Translational upregulation of folate receptors is mediated by homocysteine via RNA-heterogeneous nuclear ribonucleoprotein E1 interactions. J Clin Invest 2004; 113:285-301.

Antony A C. In: Hoffman R, Benz (Jr) EJ, Silberstein L E, Heslop H E, Weitz J I, and Anastasi J eds. Hematology: Basic Principles and Practice Edition 6. Philadelphia: Elsevier Saunders; 2013:473-504.

Tang Y S, Khan R A, Zhang Y, Xiao S, Wang M, Hansen D K, Jayaram H N, and Antony A C. Incrimination of heterogeneous nuclear ribonucleoprotein E1 (hnRNP-E1) as a candidate sensor of physiological folate deficiency. J Biol Chem 2011; 286:39100-15.

Antony A C, Utley C, Van Home K C, and Kolhouse J F. Isolation and characterization of a folate receptor from human placenta. J Biol Chem 1981; 256:9684-92.

Xiao X, Tang Y S, Mackins J Y, Sun X L, Jayaram H N, Hansen D K, and Antony A C. Isolation and characterization of a folate receptor mRNA-binding trans-factor from human placenta. Evidence favoring identity with heterogeneous nuclear ribonucleoprotein E1. J Biol Chem 2001; 276:41510-7.

Pillai M R, Chacko P, Kesari L A, Jayaprakash P G, Jayaram H N, and Antony A C. Expression of folate receptors and heterogeneous nuclear ribonucleoprotein E1 in women with human papillomavirus mediated transformation of cervical tissue to cancer. J Clin Pathol 2003; 56:569-74.

Antony A C, Kincade R S, Verma R S, and Krishnan S R. Identification of high affinity folate binding proteins in human erythrocyte membranes. J Clin Invest 1987; 80:711-23.

Ostareck-Lederer A, Ostareck D H, Standart N, and Thiele B J. Translation of 15-lipoxygenase mRNA is inhibited by a protein that binds to a repeated sequence in the 3' untranslated region. EMBO J 1994; 13:1476-81.

Ostareck D H, Ostareck-Lederer A, Wilm M, Thiele B J, Mann M, and Hentze M W. mRNA silencing in erythroid differentiation: hnRNP K and hnRNP E1 regulate 15-lipoxygenase translation from the 3' end. Cell 1997; 89:597-606.

Antony A C, Bruno E, Briddell R A, Brandt J E, Verma R S, and Hoffman R. Effect of perturbation of specific folate receptors during in vitro erythropoiesis. J Clin Invest 1987; 80:1618-23.

Chkheidze A N, Lyakhov D L, Makeyev A V, Morales J, Kong J, and Liebhaber S A. Assembly of the alpha-globin mRNA stability complex reflects binary interaction between the pyrimidine-rich 3' untranslated region determinant and poly(C) binding protein alphaCP. Mol Cell Biol 1999; 19:4572-81.

Kiledjian M, Wang X, and Liebhaber S A. Identification of two KH domain proteins in the alpha-globin mRNP stability complex. EMBO J 1995; 14:4357-64.

Xiao S, Hansen D K, Horsley E T, Tang Y S, Khan R A, Stabler S P, Jayaram H N, and Antony A C. Maternal folate deficiency results in selective upregulation of folate receptors and heterogeneous nuclear ribonucleoprotein-E1 associated with multiple subtle aberrations in fetal tissues. Birth Defects Res A Clin Mol Teratol 2005; 73:6-28.

Ostareck-Lederer A, Ostareck D H, and Hentze M W. Cytoplasmic regulatory functions of the KH-domain proteins hnRNPs K and E1/E2. Trends Biochem Sci 1998; 23:409-11.

Makeyev A V, and Liebhaber S A. The poly(C)-binding proteins: a multiplicity of functions and a search for mechanisms. RNA 2002; 8:265-78.

Chaudhury A, Chander P, and Howe P H. Heterogeneous nuclear ribonucleoproteins (hnRNPs) in cellular processes: Focus on hnRNP E1's multifunctional regulatory roles. RNA 2010; 16:1449-62.

Xiao S, Tang Y S, Khan R A, Zhang Y, Kusumanchi P, Stabler S P, Jayaram H N, and Antony A C. Influence of physiologic folate deficiency on human papillomavirus type 16 (HPV16)-harboring human keratinocytes in vitro and in vivo. J Biol Chem 2012; 287:12559-77.

Sun X L, and Antony A C. Evidence that a specific interaction between an 18-nt cis-element in the 5'-untranslated region of human folate receptor-alpha mRNA and a 46-kDa cytosolic trans-factor is critical for translation. J Biol Chem 1996; 271:25539-47.

Wang X, Kiledjian M, Weiss I M, and Liebhaber S A. Detection and characterization of a 3' untranslated region ribonucleoprotein complex associated with human alpha-globin mRNA stability [published erratum appears in Mol Cell Biol 1995 April; 15(4):2331]. Mol Cell Biol 1995; 15:1769-77.

Antony A C. In: Goldman L, and Schafer A I eds. Goldman-Cecil Medicine, (Cecil's Textbook of Medicine) 25th Edition. New York: Elsevier Saunders; 2015:1104-14.

Stabler S P, Marcell P D, Podell E R, Allen R H, Savage D G, and Lindenbaum J. Elevation of total homocysteine in the serum of patients with cobalamin or folate deficiency detected by capillary gas chromatography-mass spectrometry. J Clin Invest 1988; 81:466-74.

Shi H, Bencze K Z, Stemmler T L, and Philpott C C. A cytosolic iron chaperone that delivers iron to ferritin. Science 2008; 320:1207-10.

Philpott C C. Coming into view: eukaryotic iron chaperones and intracellular iron delivery. J Biol Chem 2012; 287: 13518-23.

Hider R C, and Kong X. Iron speciation in the cytosol: an overview. Dalton Trans 2013; 42:3220-9.

Hider R C, and Kong X L. Glutathione: a key component of the cytoplasmic labile iron pool. Biometals 2011; 24:1179-87.

Sun X L, Murphy B R, Li Q J, Gullapalli S, Mackins J, Jayaram H N, Srivastava A, and Antony A C. Transduction of folate receptor cDNA into cervical carcinoma cells using recombinant adeno-associated virions delays cell proliferation in vitro and in vivo. J Clin Invest 1995; 96:1535-47.

Waggoner S A, and Liebhaber S A. Identification of mRNAs associated with alphaCP2-containing RNP complexes. Mol Cell Biol 2003; 237055-67.

Boshnjaku V, Shim K W, Tsurubuchi T, Ichi S, Szany E V, Xi G, Mania-Farnell B, McLone D G, Tomita T, and Mayanil C S. Nuclear localization of folate receptor alpha: a new role as a transcription factor. Sci Rep 2012; 2:980; DOI:10.1038/srep00980.

Stabler S P. Clinical practice. Vitamin B12 deficiency. N Engl J Med 2013; 368:149-60.

Leamon C P, Reddy J A, Dorton R, Bloomfield A, Emsweller K, Parker N, and Westrick E. Impact of high and low folate diets on tissue folate receptor levels and antitumor responses toward folate-drug conjugates. J Pharmacol Exp Ther 2008; 327:918-25.

Torheim L E, Ferguson E L, Penrose K, and Arimond M. Women in resource-poor settings are at risk of inadequate intakes of multiple micronutrients. J Nutr 2010; 140: 2051S-8S.

WHO. Micronutrient deficiencies: Iron deficiency anaemia. Available at who.int/nutrition/topics/ida/en/index on the world wide web. Accessed Sep. 10, 2010.

Czyzyk-Krzeska M F, Paulding W R, Beresh J E, and Kroll S L. Post-transcriptional regulation of tyrosine hydroxylase gene expression by oxygen in PC12 cells. Kidney Int 1997; 51:585-90.

Paulding W R, and Czyzyk-Krzeska M F. Regulation of tyrosine hydroxylase mRNA stability by protein-binding, pyrimidine-rich sequence in the 3'-untranslated region. J Biol Chem 1999; 274:2532-8.

Thyagarajan A, and Szaro B G. Phylogenetically conserved binding of specific K homology domain proteins to the 3'-untranslated region of the vertebrate middle neurofilament mRNA. J Biol Chem 2004; 279:49680-8.

Thyagarajan A, Strong M J, and Szaro B G. Post-transcriptional control of neurofilaments in development and disease. Exp Cell Res 2007; 313:2088-97.

Thyagarajan A, and Szaro B G. Dynamic endogenous association of neurofilament mRNAs with K-homology domain ribonucleoproteins in developing cerebral cortex. Brain Res 2008; 1189:33-42.

Kong J, Tung V W, Aghajanian J, and Xu Z. Antagonistic roles of neurofilament subunits NF-H and NF-M against NF-L in shaping dendritic arborization in spinal motor neurons. J Cell Biol 1998; 140:1167-76.

Wong P C, Marszalek J, Crawford T O, Xu Z, Hsieh S T, Griffin J W, and Cleveland D W. Increasing neurofilament subunit NF-M expression reduces axonal NF-H, inhibits radial growth, and results in neurofilamentous accumulation in motor neurons. J Cell Biol 1995; 130:1413-22.

Xu Z, Marszalek J R, Lee M K, Wong P C, Folmer J, Crawford T O, Hsieh S T, Griffin J W, and Cleveland D W. Subunit composition of neurofilaments specifies axonal diameter. J Cell Biol 1996; 133:1061-9.

Xu Z, and Tung V W. Overexpression of neurofilament subunit M accelerates axonal transport of neurofilaments. Brain Res 2000; 866:326-32.

Ferguson S A, Berry K J, Hansen D K, Wall K S, White G, and Antony A C. Behavioral effects of prenatal folate deficiency in mice. Birth Defects Res A Clin Mol Teratol 2005; 73:249-52.

Schlotz W, Jones A, Phillips D I, Gale C R, Robinson S M, and Godfrey K M. Lower maternal folate status in early pregnancy is associated with childhood hyperactivity and peer problems in offspring. J Child Psychol Psychiatry 2010; 51:594-602.

Steenweg-de Graaff J, Roza S J, Steegers E A, Hofman A, Verhulst F C, Jaddoe V W, and Tiemeier H. Maternal folate status in early pregnancy and child emotional and behavioral problems: the Generation R Study. Am J Clin Nutr 2012; 95:1413-21.

Suren P, Roth C, Bresnahan M, Haugen M, Hornig M, Hirtz D, Lie K K, Lipkin W I, Magnus P, Reichborn-Kjennerud T, et al. Association between maternal use of folic acid supplements and risk of autism spectrum disorders in children. JAMA 2013; 309:570-7.

Strand T A, Taneja S, Ueland P M, Refsum H, Bahl R, Schneede J, Sommerfelt H, and Bhandari N. Cobalamin and folate status predicts mental development scores in North Indian children 12-18 mo of age. Am J Clin Nutr 2013; 97:310-7.

Veena S R, Krishnaveni G V, Srinivasan K, Wills A K, Muthayya S, Kurpad A V, Yajnik C S, and Fall C H. Higher maternal plasma folate but not vitamin B-12 concentrations during pregnancy are associated with better cognitive function scores in 9- to 10-year-old children in South India. J Nut 2010; 140:1014-22.

Lozoff B, Jimenez E, and Wolf A W. Long-term developmental outcome of infants with iron deficiency. N Engl J Med 1991; 325:687-94.

Lozoff B, Jimenez E, Hagen J, Mollen E, and Wolf A W. Poorer behavioral and developmental outcome more than 10 years after treatment for iron deficiency in infancy. Pediatrics 2000; 105:E51.

Lozoff B, DeAndraca I, Castillo M, Smith J B, Walter T, and Pino P. Behavioral and developmental effects of preventing iron-deficiency anemia in healthy full-term infants. Pediatrics 2003; 112:846-54.

Chang S, Wang L, Wang Y, Brouwer I D, Kok F J, Lozoff B, and Chen C. Iron-deficiency anemia in infancy and social emotional development in preschool-aged Chinese children. Pediatrics 2011; 127:e927-33.

Monk C, Georgieff M K, and Osterholm E A. Research review: maternal prenatal distress and poor nutrition— mutually influencing risk factors affecting infant neurocognitive development. J Child Psychol Psychiatry 2013; 54:115-30.

Brunette K E, Tran P V, Wobken J D, Carlson E S, and Georgieff M K. Gestational and neonatal iron deficiency alters apical dendrite structure of CA1 pyramidal neurons in adult rat hippocampus. Dev Neurosci 2010; 32:238-48.

Georgieff M K. Long-term brain and behavioral consequences of early iron deficiency. Nutr Rev 2011; 69 Suppl 1:S43-8.

Tran P V, Dakoji S, Reise K H, Storey K K, and Georgieff M K. Fetal iron deficiency alters the proteome of adult rat hippocampal synaptosomes. Am J Physiol Regul Integr Comp Physiol 2013; 305:R1297-306.

Baker R D, and Greer F R. Diagnosis and prevention of iron deficiency and iron-deficiency anemia in infants and young children (0-3 years of age). Pediatrics 2010; 126:1040-50.

Christian P, Murray-Kolb L E, Khatry S K, Katz J, Schaefer B A, Cole P M, Leclerq S C, and Tielsch J M. Prenatal micronutrient supplementation and intellectual and motor function in early school-aged children in Nepal. JAMA 2010; 304:2716-23.

Meng Q, Rayala S K, Gururaj A E, Talukder A H, O'Malley B W, and Kumar R. Signaling-dependent and coordinated regulation of transcription, splicing, and translation resides in a single coregulator, PCBP1. Proc Natl Acad Sci USA 2007; 104:5866-71.

Dobbyn H C, Hill K, Hamilton T L, Spriggs K A, Pickering B M, Coldwell M J, de Moor C H, Bushell M, and Willis A E. Regulation of BAG-1 IRES-mediated translation following chemotoxic stress. Oncogene 2008; 27:1167-74.

Lewis S M, Veyrier A, Hosszu Ungureanu N, Bonnal S, Vagner S, and Holcik M. Subcellular relocalization of a trans-acting factor regulates XIAP IRES-dependent translation. Mol Biol Cell 2007; 18:1302-11.

Lewis S M, and Holcik M. For IRES trans-acting factors, it is all about location. Oncogene 2008; 27:1033-5.

Jiang Y, Xu X S, and Russell J E. A nucleolin-binding 3' untranslated region element stabilizes beta-globin mRNA in vivo. Mol Cell Biol 2006; 26:2419-29.

Czyzyk-Krzeska M F, and Bendixen A C. Identification of the poly(C) binding protein in the complex associated with the 3' untranslated region of erythropoietin messenger RNA. Blood 1999; 93:2111-20.

Pickering B M, Mitchell S A, Evans J R, and Willis A E. Polypyrimidine tract binding protein and poly r(C) binding protein 1 interact with the BAG-1 IRES and stimulate its activity in vitro and in vivo. Nucleic Acids Res 2003; 31:639-46.

Holcik M, and Korneluk R G. XIAP, the guardian angel. Nat Rev Mol Cell Biol 2001; 2:550-6.

Chappell S A, LeQuesne J P, Paulin F E, deSchoolmeester M L, Stoneley M, Soutar R L, Ralston S H, Helfrich M R, and Willis A E. A mutation in the c-myc-IRES leads to enhanced internal ribosome entry in multiple myeloma: a novel mechanism of oncogene de-regulation. Oncogene 2000; 19:4437-40.

Rondon I J, MacMillan L A, Beckman B S, Goldberg M A, Schneider T, Bunn H F, and Malter J S. Hypoxia up-regulates the activity of a novel erythropoietin mRNA binding protein. J Biol Chem 1991; 266:16594-8.

Giles K M, Daly J M, Beveridge D J, Thomson A M, Voon D C, Furneaux H M, Jazayeri J A, and Leedman P J. The 3'-untranslated region of p21WAF1 mRNA is a composite cis-acting sequence bound by RNA-binding proteins from breast cancer cells, including HuR and poly(C)-binding protein. J Biol Chem 2003; 278:2937-46.

Collier B, Goobar-Larsson L, Sokolowski M, and Schwartz S. Translational inhibition in vitro of human papillomavirus type 16 L2 mRNA mediated through interaction with heterogenous ribonucleoprotein K and poly(rC)-binding proteins 1 and 2. J Biol Chem 1998; 273:22648-56.

Czyzyk-Krzeska M F, and Beresh J E. Characterization of the hypoxia-inducible protein binding site within the pyrimidine-rich tract in the 3'-untranslated region of the tyrosine hydroxylase mRNA. J Biol Chem 1996; 271:3293-9.

Ule J, Jensen K B, Ruggiu M, Mele A, Ule A, and Darnell R B. CLIP identifies Nova-regulated RNA networks in the brain. Science 2003; 302:1212-5.

Darnell R B, and Posner J B. Paraneoplastic syndromes affecting the nervous system. Semin Oncol 2006; 33:270-98.

Darnell R B. Onconeural antigens and the paraneoplastic neurologic disorders: at the intersection of cancer, immunity, and the brain. Proc Natl Acad Sci USA 1996; 93:4529-36.

Waggoner S A, Johannes G J, and Liebhaber S A. Depletion of the poly(C)-binding proteins alphaCP1 and alphaCP2 from K562 cells leads to p53-independent induction of cyclin-dependent kinase inhibitor (CDKN1A) and G1 arrest. J Biol Chem 2009; 284:9039-49.

Musunuru K, and Darnell R B. Determination and augmentation of RNA sequence specificity of the Nova K-homology domains. Nucleic Acids Res 2004; 32:4852-61.

Keene J D. RNA regulons: coordination of post-transcriptional events. Nat Rev Genet 2007; 8:533-43.

Tang Y S, Khan R A, Zhang Y, Xiao S, Wang M, Hansen D K, Jayaram H N, and Antony A C. Incrimination of heterogeneous nuclear ribonucleoprotein E1 (hnRNP-E1) as a candidate sensor of physiological folate deficiency. J Biol Chem 2011; 286:39100-15.

Xiao X, Tang Y S, Mackins J Y, Sun X L, Jayaram H N, Hansen D K, and Antony A C. Isolation and characterization of a folate receptor mRNA-binding trans-factor from human placenta. Evidence favoring identity with heterogeneous nuclear ribonucleoprotein E1. J Biol Chem 2001; 276:41510-7.

Dejgaard K, and Leffers H. Characterisation of the nucleic-acid-binding activity of KH domains. Different properties of different domains. Eur J Biochem 1996; 241:425-31.

Leffers H, Dejgaard K, and Celis J E. Characterisation of two major cellular poly(rC)-binding human proteins, each containing three K-homologous (KH) domains. Eur J Biochem 1995; 230:447-53.

Xiao S, Tang Y S, Khan R A, Zhang Y, Kusumanchi P, Stabler S P, Jayaram H N, and Antony A C. Influence of physiologic folate deficiency on human papillomavirus type 16 (HPV16)-harboring human keratinocytes in vitro and in vivo. J Biol Chem 2012; 287:12559-77.

Antony A C, Tang Y S, Khan R A, Biju M P, Xiao X, Li Q J, Sun X L, Jayaram H N, and Stabler S P. Translational upregulation of folate receptors is mediated by homocysteine via RNA-heterogeneous nuclear ribonucleoprotein E1 interactions. J Clin Invest 2004; 113:285-301.

Xiao S, Hansen D K, Horsley E T, Tang Y S, Khan R A, Stabler S P, Jayaram H N, and Antony A C. Maternal folate deficiency results in selective upregulation of folate receptors and heterogeneous nuclear ribonucleoprotein- E1 associated with multiple subtle aberrations in fetal tissues. Birth Defects Res A Clin Mol Teratol 2005; 73:6-28.

Sun X L, Murphy B R, Li Q J, Gullapalli S, Mackins J, Jayaram H N, Srivastava A, and Antony A C. Transduction of folate receptor cDNA into cervical carcinoma cells using recombinant adeno-associated virions delays cell proliferation in vitro and in vivo. J Clin Invest 1995; 96:1535-47.

Kaufman M H. The atlas of mouse development. San Diego: Academic Press; 1992.

Chaudhury A, Chander P, and Howe P H. Heterogeneous nuclear ribonucleoproteins (hnRNPs) in cellular processes: Focus on hnRNP E1's multifunctional regulatory roles. RNA 2010; 16:1449-62.

Ghanem L R, Chatterji P, and Liebhaber S A. Specific enrichment of the RNA-binding proteins PCBP1 and PCBP2 in chief cells of the murine gastric mucosa. Gene Expr Patterns 2014; 14:78-87.

Antony A C. In: Hoffman R, Benz (Jr) EJ, Silberstein L E, Heslop H E, Weitz J I, and Anastasi J eds. Hematology: Basic Principles and Practice Edition 6. Philadelphia: Elsevier Saunders; 2013:473-504.

Antony A C, and Hansen D K. Hypothesis: folate-responsive neural tube defects and neurocristopathies. Teratology 2000; 62:42-50.

Pillai M R, Chacko P, Kesari L A, Jayaprakash P G, Jayaram H N, and Antony A C. Expression of folate receptors and heterogeneous nuclear ribonucleoprotein E1 in women with human papillomavirus mediated transformation of cervical tissue to cancer. J Clin Pathol 2003; 56:569-74.

Antony A C. In: Goldman L, and Schafer A I eds. Goldman-Cecil Medicine, (Cecil's Textbook of Medicine) 25th Edition. New York: Elsevier Saunders; 2015:1104-14.

Stabler S P, Marcell P D, Podell E R, Allen R H, Savage D G, and Lindenbaum J. Elevation of total homocysteine in the serum of patients with cobalamin or folate deficiency detected by capillary gas chromatography-mass spectrometry. J Clin Invest 1988; 81:466-74.

Olsen J V, Ong S E, and Mann M. Trypsin cleaves exclusively C-terminal to arginine and lysine residues. Mol Cell Proteomics 2004; 3:608-14.

Sidiqi M, Wilce J A, Vivian J P, Porter C J, Barker A, Leedman P J, and Wilce M C. Structure and RNA binding of the third KH domain of poly(C)-binding protein 1. Nucleic Acids Res 2005; 33:1213-21.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

What is claimed is:

1. An isolated variant of a native hnRNP-E1 polypeptide, wherein the variant hnRNP-E1 polypeptide comprises (i) at least one amino acid substitution at an amino acid residue selected from C293, C54, C158, and C201 of SEQ ID NO:1, wherein the amino acid substitution replaces a native cysteine residues with a serine residue and (ii) an RNA binding portion that binds a single-stranded RNA that comprises SEQ ID NO:6 in the absence of homocysteine and is optionally linked to a protein transduction domain.

2. The variant hnRNP-E1 polypeptide of claim 1, wherein the variant hnRNP-E1 polypeptide binds the single-stranded RNA comprising SEQ ID NO:6 independent of homocysteine concentration.

3. The variant hnRNP-E1 polypeptide of claim 1, wherein the variant hnRNP-E1 polypeptide comprises an amino acid sequence at least 95% identical to any one of SEQ ID NOs:2-5.

4. The variant hnRNP-E1 polypeptide of claim 1, wherein the variant hnRNP-E1 polypeptide comprises an amino acid sequence selected from the group consisting of SEQ ID NOs:2-5.

5. The variant hnRNP-E1 polypeptide of claim 4, wherein the amino acid sequence is SEQ ID NO:2.

6. The variant hnRNP-E1 polypeptide of claim 1, wherein the is linked to the protein transduction domain.

7. The variant hnRNP-E1 polypeptide of claim 6, wherein the protein transduction domain comprises any of SEQ ID NOs:7-11.

8. A pharmaceutical composition comprising the variant hnRNP-E1 polypeptide of claim 1 and a pharmaceutically acceptable carrier.

9. A method for increasing translation of a target mRNA in a mammalian cell, the method comprising the step of:
providing in the mammalian cell the polypeptide of claim 1, wherein the target mRNA comprises a poly(rC)- and poly(U)-rich 5' UTR, thereby increasing translation of the target mRNA in the mammalian cell.

10. The method of claim 9, wherein the polypeptide comprises an RNA binding portion comprising SEQ ID NO: 2.

11. The method of claim 9, wherein the providing step is selected from the group consisting of administering the polypeptide to the cell and expressing the polypeptide within the cell.

12. The method of claim 11, wherein the expressing step includes delivering into the mammalian cell a nucleic acid encoding the polypeptide whereby the polypeptide is expressed.

13. The method of claim 9, wherein the target mRNA is selected from the group consisting of folate receptor mRNA, hnRNP-E1 mRNA, collagen alpha (I) mRNA, human papillomavirus type 16 L2 mRNA, human herpesvirus 8 mRNA, erythropoietin mRNA, human alpha-globin mRNA, human beta-globin mRNA, μ-opioid receptor mRNA, androgen receptor mRNA, p21waf mRNA, tyrosine hydroxylase mRNA, and neurofilament M mRNA.

* * * * *

UNITED STATES PATENT AND TRADEMARK OFFICE
CERTIFICATE OF CORRECTION

PATENT NO. : 10,093,706 B2
APPLICATION NO. : 15/419655
DATED : October 9, 2018
INVENTOR(S) : Asok C. Antony et al.

Page 1 of 1

It is certified that error appears in the above-identified patent and that said Letters Patent is hereby corrected as shown below:

On the Title Page

Item (54), "HNRNP" should be --hnRNP--.

In the Specification

Column 5, Line 44, "20-lag" should be --20-µg--.

Column 19, Line 24, "Pst1" should be --PstI--.

Column 19, Line 29, "Pst1" should be --PstI--.

Column 19, Line 31, "Pst1" should be --PstI--.

Column 19, Line 40, "Nhe1" should be --NheI--.

Column 20, Line 5, "Pst1" should be --PstI--.

Column 28, Line 54, "32-11M" should be --32-µM--.

Column 47, Line 50, "Van Home" should be --Van Horne--.

Column 50, Line 50, "Nut" should be --Nutr--.

In the Claims

Column 87, Line 53, "the is" should be --the RNA binding portion is--.

Signed and Sealed this
Twentieth Day of November, 2018

Andrei Iancu
*Director of the United States Patent and Trademark Office*

SEQUENCE LISTING

```
<160> NUMBER OF SEQ ID NOS: 75

<210> SEQ ID NO 1
<211> LENGTH: 356
<212> TYPE: PRT
<213> ORGANISM: Homo sapiens

<400> SEQUENCE: 1

Met Asp Ala Gly Val Thr Glu Ser Gly Leu Asn Val Thr Leu Thr Ile
1               5                   10                  15

Arg Leu Leu Met His Gly Lys Glu Val Gly Ser Ile Ile Gly Lys Lys
            20                  25                  30

Gly Glu Ser Val Lys Arg Ile Arg Glu Glu Ser Gly Ala Arg Ile Asn
        35                  40                  45

Ile Ser Glu Gly Asn Cys Pro Glu Arg Ile Ile Thr Leu Thr Gly Pro
    50                  55                  60

Thr Asn Ala Ile Phe Lys Ala Phe Ala Met Ile Ile Asp Lys Leu Glu
65                  70                  75                  80

Glu Asp Ile Asn Ser Ser Met Thr Asn Ser Thr Ala Ala Ser Arg Pro
                85                  90                  95

Pro Val Thr Leu Arg Leu Val Val Pro Ala Thr Gln Cys Gly Ser Leu
            100                 105                 110

Ile Gly Lys Gly Gly Cys Lys Ile Lys Glu Ile Arg Glu Ser Thr Gly
        115                 120                 125

Ala Gln Val Gln Val Ala Gly Asp Met Leu Pro Asn Ser Thr Glu Arg
    130                 135                 140

Ala Ile Thr Ile Ala Gly Val Pro Gln Ser Val Thr Glu Cys Val Lys
145                 150                 155                 160

Gln Ile Cys Leu Val Met Leu Glu Thr Leu Ser Gln Ser Pro Gln Gly
                165                 170                 175
```

-continued

```
Arg Val Met Thr Ile Pro Tyr Gln Pro Met Pro Ala Ser Ser Pro Val
            180                 185                 190

Ile Cys Ala Gly Gly Gln Asp Arg Cys Ser Asp Ala Val Gly Tyr Pro
        195                 200                 205

His Ala Thr His Asp Leu Glu Gly Pro Pro Leu Asp Ala Tyr Ser Ile
    210                 215                 220

Gln Gly Gln His Thr Ile Ser Pro Leu Asp Leu Ala Lys Leu Asn Gln
225                 230                 235                 240

Val Ala Arg Gln Gln Ser His Phe Ala Met Met His Gly Gly Thr Gly
                245                 250                 255

Phe Ala Gly Ile Asp Ser Ser Pro Glu Val Lys Gly Tyr Trp Ala
            260                 265                 270

Ser Leu Asp Ala Ser Thr Gln Thr Thr His Glu Leu Thr Ile Pro Asn
        275                 280                 285

Asn Leu Ile Gly Cys Ile Ile Gly Arg Gln Gly Ala Asn Ile Asn Glu
    290                 295                 300

Ile Arg Gln Met Ser Gly Ala Gln Ile Lys Ile Ala Asn Pro Val Glu
305                 310                 315                 320

Gly Ser Ser Gly Arg Gln Val Thr Ile Thr Gly Ser Ala Ala Ser Ile
                325                 330                 335

Ser Leu Ala Gln Tyr Leu Ile Asn Ala Arg Leu Ser Ser Glu Lys Gly
        340                 345                 350

Met Gly Cys Ser
        355

<210> SEQ ID NO 2
<211> LENGTH: 356
<212> TYPE: PRT
<213> ORGANISM: Artificial Sequence
<220> FEATURE:
<223> OTHER INFORMATION: synthetic

<400> SEQUENCE: 2

Met Asp Ala Gly Val Thr Glu Ser Gly Leu Asn Val Thr Leu Thr Ile
1               5                   10                  15

Arg Leu Leu Met His Gly Lys Glu Val Gly Ser Ile Ile Gly Lys Lys
            20                  25                  30

Gly Glu Ser Val Lys Arg Ile Arg Glu Glu Ser Gly Ala Arg Ile Asn
        35                  40                  45

Ile Ser Glu Gly Asn Cys Pro Glu Arg Ile Ile Thr Leu Thr Gly Pro
    50                  55                  60

Thr Asn Ala Ile Phe Lys Ala Phe Ala Met Ile Ile Asp Lys Leu Glu
65                  70                  75                  80

Glu Asp Ile Asn Ser Ser Met Thr Asn Ser Thr Ala Ala Ser Arg Pro
                85                  90                  95

Pro Val Thr Leu Arg Leu Val Val Pro Ala Thr Gln Cys Gly Ser Leu
            100                 105                 110

Ile Gly Lys Gly Gly Cys Lys Ile Lys Glu Ile Arg Glu Ser Thr Gly
        115                 120                 125

Ala Gln Val Gln Val Ala Gly Asp Met Leu Pro Asn Ser Thr Glu Arg
    130                 135                 140

Ala Ile Thr Ile Ala Gly Val Pro Gln Ser Val Thr Glu Cys Val Lys
145                 150                 155                 160

Gln Ile Cys Leu Val Met Leu Glu Thr Leu Ser Gln Ser Pro Gln Gly
                165                 170                 175
```

-continued

```
Arg Val Met Thr Ile Pro Tyr Gln Pro Met Pro Ala Ser Ser Pro Val
            180                 185                 190

Ile Cys Ala Gly Gly Gln Asp Arg Cys Ser Asp Ala Val Gly Tyr Pro
        195                 200                 205

His Ala Thr His Asp Leu Glu Gly Pro Pro Leu Asp Ala Tyr Ser Ile
    210                 215                 220

Gln Gly Gln His Thr Ile Ser Pro Leu Asp Leu Ala Lys Leu Asn Gln
225                 230                 235                 240

Val Ala Arg Gln Gln Ser His Phe Ala Met Met His Gly Gly Thr Gly
                245                 250                 255

Phe Ala Gly Ile Asp Ser Ser Pro Glu Val Lys Gly Tyr Trp Ala
            260                 265                 270

Ser Leu Asp Ala Ser Thr Gln Thr Thr His Glu Leu Thr Ile Pro Asn
        275                 280                 285

Asn Leu Ile Gly Ser Ile Ile Gly Arg Gln Gly Ala Asn Ile Asn Glu
    290                 295                 300

Ile Arg Gln Met Ser Gly Ala Gln Ile Lys Ile Ala Asn Pro Val Glu
305                 310                 315                 320

Gly Ser Ser Gly Arg Gln Val Thr Ile Thr Gly Ser Ala Ala Ser Ile
                325                 330                 335

Ser Leu Ala Gln Tyr Leu Ile Asn Ala Arg Leu Ser Ser Glu Lys Gly
            340                 345                 350

Met Gly Cys Ser
        355
```

<210> SEQ ID NO 3
<211> LENGTH: 356
<212> TYPE: PRT
<213> ORGANISM: Artificial Sequence
<220> FEATURE:
<223> OTHER INFORMATION: synthetic

<400> SEQUENCE: 3

```
Met Asp Ala Gly Val Thr Glu Ser Gly Leu Asn Val Thr Leu Thr Ile
1               5                   10                  15

Arg Leu Leu Met His Gly Lys Glu Val Gly Ser Ile Ile Gly Lys Lys
            20                  25                  30

Gly Glu Ser Val Lys Arg Ile Arg Glu Glu Ser Gly Ala Arg Ile Asn
        35                  40                  45

Ile Ser Glu Gly Asn Ser Pro Glu Arg Ile Ile Thr Leu Thr Gly Pro
    50                  55                  60

Thr Asn Ala Ile Phe Lys Ala Phe Ala Met Ile Ile Asp Lys Leu Glu
65                  70                  75                  80

Glu Asp Ile Asn Ser Ser Met Thr Asn Ser Thr Ala Ala Ser Arg Pro
                85                  90                  95

Pro Val Thr Leu Arg Leu Val Val Pro Ala Thr Gln Cys Gly Ser Leu
            100                 105                 110

Ile Gly Lys Gly Gly Cys Lys Ile Lys Glu Ile Arg Glu Ser Thr Gly
        115                 120                 125

Ala Gln Val Gln Val Ala Gly Asp Met Leu Pro Asn Ser Thr Glu Arg
    130                 135                 140

Ala Ile Thr Ile Ala Gly Val Pro Gln Ser Val Thr Glu Cys Val Lys
145                 150                 155                 160

Gln Ile Cys Leu Val Met Leu Glu Thr Leu Ser Gln Ser Pro Gln Gly
                165                 170                 175
```

```
Arg Val Met Thr Ile Pro Tyr Gln Pro Met Pro Ala Ser Ser Pro Val
            180                 185                 190

Ile Cys Ala Gly Gly Gln Asp Arg Cys Ser Asp Ala Val Gly Tyr Pro
            195                 200                 205

His Ala Thr His Asp Leu Glu Gly Pro Pro Leu Asp Ala Tyr Ser Ile
            210                 215                 220

Gln Gly Gln His Thr Ile Ser Pro Leu Asp Leu Ala Lys Leu Asn Gln
225                 230                 235                 240

Val Ala Arg Gln Gln Ser His Phe Ala Met Met His Gly Gly Thr Gly
            245                 250                 255

Phe Ala Gly Ile Asp Ser Ser Pro Glu Val Lys Gly Tyr Trp Ala
            260                 265                 270

Ser Leu Asp Ala Ser Thr Gln Thr Thr His Glu Leu Thr Ile Pro Asn
            275                 280                 285

Asn Leu Ile Gly Cys Ile Ile Gly Arg Gln Gly Ala Asn Ile Asn Glu
            290                 295                 300

Ile Arg Gln Met Ser Gly Ala Gln Ile Lys Ile Ala Asn Pro Val Glu
305                 310                 315                 320

Gly Ser Ser Gly Arg Gln Val Thr Ile Thr Gly Ser Ala Ala Ser Ile
            325                 330                 335

Ser Leu Ala Gln Tyr Leu Ile Asn Ala Arg Leu Ser Ser Glu Lys Gly
            340                 345                 350

Met Gly Cys Ser
        355

<210> SEQ ID NO 4
<211> LENGTH: 356
<212> TYPE: PRT
<213> ORGANISM: Artificial Sequence
<220> FEATURE:
<223> OTHER INFORMATION: synthetic

<400> SEQUENCE: 4

Met Asp Ala Gly Val Thr Glu Ser Gly Leu Asn Val Thr Leu Thr Ile
1               5                   10                  15

Arg Leu Leu Met His Gly Lys Glu Val Gly Ser Ile Ile Gly Lys Lys
            20                  25                  30

Gly Glu Ser Val Lys Arg Ile Arg Glu Glu Ser Gly Ala Arg Ile Asn
            35                  40                  45

Ile Ser Glu Gly Asn Cys Pro Glu Arg Ile Ile Thr Leu Thr Gly Pro
        50                  55                  60

Thr Asn Ala Ile Phe Lys Ala Phe Ala Met Ile Ile Asp Lys Leu Glu
65                  70                  75                  80

Glu Asp Ile Asn Ser Ser Met Thr Asn Ser Thr Ala Ala Ser Arg Pro
            85                  90                  95

Pro Val Thr Leu Arg Leu Val Val Pro Ala Thr Gln Cys Gly Ser Leu
            100                 105                 110

Ile Gly Lys Gly Gly Cys Lys Ile Lys Glu Ile Arg Glu Ser Thr Gly
            115                 120                 125

Ala Gln Val Gln Val Ala Gly Asp Met Leu Pro Asn Ser Thr Glu Arg
            130                 135                 140

Ala Ile Thr Ile Ala Gly Val Pro Gln Ser Val Thr Glu Ser Val Lys
145                 150                 155                 160

Gln Ile Cys Leu Val Met Leu Glu Thr Leu Ser Gln Ser Pro Gln Gly
            165                 170                 175
```

```
Arg Val Met Thr Ile Pro Tyr Gln Pro Met Pro Ala Ser Ser Pro Val
            180                 185                 190

Ile Cys Ala Gly Gly Gln Asp Arg Cys Ser Asp Ala Val Gly Tyr Pro
        195                 200                 205

His Ala Thr His Asp Leu Glu Gly Pro Pro Leu Asp Ala Tyr Ser Ile
    210                 215                 220

Gln Gly Gln His Thr Ile Ser Pro Leu Asp Leu Ala Lys Leu Asn Gln
225                 230                 235                 240

Val Ala Arg Gln Gln Ser His Phe Ala Met Met His Gly Gly Thr Gly
                245                 250                 255

Phe Ala Gly Ile Asp Ser Ser Pro Glu Val Lys Gly Tyr Trp Ala
        260                 265                 270

Ser Leu Asp Ala Ser Thr Gln Thr Thr His Glu Leu Thr Ile Pro Asn
    275                 280                 285

Asn Leu Ile Gly Cys Ile Ile Gly Arg Gln Gly Ala Asn Ile Asn Glu
    290                 295                 300

Ile Arg Gln Met Ser Gly Ala Gln Ile Lys Ile Ala Asn Pro Val Glu
305                 310                 315                 320

Gly Ser Ser Gly Arg Gln Val Thr Ile Thr Gly Ser Ala Ala Ser Ile
                325                 330                 335

Ser Leu Ala Gln Tyr Leu Ile Asn Ala Arg Leu Ser Ser Glu Lys Gly
                340                 345                 350

Met Gly Cys Ser
        355

<210> SEQ ID NO 5
<211> LENGTH: 356
<212> TYPE: PRT
<213> ORGANISM: Artificial Sequence
<220> FEATURE:
<223> OTHER INFORMATION: synthetic

<400> SEQUENCE: 5

Met Asp Ala Gly Val Thr Glu Ser Gly Leu Asn Val Thr Leu Thr Ile
1               5                   10                  15

Arg Leu Leu Met His Gly Lys Glu Val Gly Ser Ile Ile Gly Lys Lys
                20                  25                  30

Gly Glu Ser Val Lys Arg Ile Arg Glu Ser Gly Ala Arg Ile Asn
            35                  40                  45

Ile Ser Glu Gly Asn Cys Pro Glu Arg Ile Ile Thr Leu Thr Gly Pro
    50                  55                  60

Thr Asn Ala Ile Phe Lys Ala Phe Ala Met Ile Ile Asp Lys Leu Glu
65                  70                  75                  80

Glu Asp Ile Asn Ser Ser Met Thr Asn Ser Thr Ala Ala Ser Arg Pro
                85                  90                  95

Pro Val Thr Leu Arg Leu Val Val Pro Ala Thr Gln Cys Gly Ser Leu
            100                 105                 110

Ile Gly Lys Gly Gly Cys Lys Ile Lys Glu Ile Arg Glu Ser Thr Gly
            115                 120                 125

Ala Gln Val Gln Val Ala Gly Asp Met Leu Pro Asn Ser Thr Glu Arg
        130                 135                 140

Ala Ile Thr Ile Ala Gly Val Pro Gln Ser Val Thr Glu Cys Val Lys
145                 150                 155                 160

Gln Ile Cys Leu Val Met Leu Glu Thr Leu Ser Gln Ser Pro Gln Gly
                165                 170                 175
```

```
Arg Val Met Thr Ile Pro Tyr Gln Pro Met Pro Ala Ser Ser Pro Val
            180                 185                 190

Ile Cys Ala Gly Gly Gln Asp Arg Ser Ser Asp Ala Val Gly Tyr Pro
        195                 200                 205

His Ala Thr His Asp Leu Glu Gly Pro Pro Leu Asp Ala Tyr Ser Ile
    210                 215                 220

Gln Gly Gln His Thr Ile Ser Pro Leu Asp Leu Ala Lys Leu Asn Gln
225                 230                 235                 240

Val Ala Arg Gln Gln Ser His Phe Ala Met Met His Gly Gly Thr Gly
                245                 250                 255

Phe Ala Gly Ile Asp Ser Ser Pro Glu Val Lys Gly Tyr Trp Ala
            260                 265                 270

Ser Leu Asp Ala Ser Thr Gln Thr Thr His Glu Leu Thr Ile Pro Asn
        275                 280                 285

Asn Leu Ile Gly Cys Ile Ile Gly Arg Gln Gly Ala Asn Ile Asn Glu
    290                 295                 300

Ile Arg Gln Met Ser Gly Ala Gln Ile Lys Ile Ala Asn Pro Val Glu
305                 310                 315                 320

Gly Ser Ser Gly Arg Gln Val Thr Ile Thr Gly Ser Ala Ala Ser Ile
                325                 330                 335

Ser Leu Ala Gln Tyr Leu Ile Asn Ala Arg Leu Ser Ser Glu Lys Gly
            340                 345                 350

Met Gly Cys Ser
        355

<210> SEQ ID NO 6
<211> LENGTH: 25
<212> TYPE: RNA
<213> ORGANISM: Homo sapiens

<400> SEQUENCE: 6
cucccgcccg cucccgcucg cuccc                                              25

<210> SEQ ID NO 7
<211> LENGTH: 11
<212> TYPE: PRT
<213> ORGANISM: Artificial Sequence
<220> FEATURE:
<223> OTHER INFORMATION: synthetic

<400> SEQUENCE: 7

Tyr Gly Arg Lys Lys Arg Arg Gln Arg Arg
1               5                   10

<210> SEQ ID NO 8
<211> LENGTH: 8
<212> TYPE: PRT
<213> ORGANISM: Artificial Sequence
<220> FEATURE:
<223> OTHER INFORMATION: synthetic

<400> SEQUENCE: 8

Arg Lys Lys Arg Arg Gln Arg Arg
1               5

<210> SEQ ID NO 9
<211> LENGTH: 11
<212> TYPE: PRT
<213> ORGANISM: Artificial Sequence
<220> FEATURE:
<223> OTHER INFORMATION: synthetic
```

<400> SEQUENCE: 9

Tyr Ala Arg Ala Ala Ala Arg Gln Ala Arg Ala
1               5                   10

<210> SEQ ID NO 10
<211> LENGTH: 11
<212> TYPE: PRT
<213> ORGANISM: Artificial Sequence
<220> FEATURE:
<223> OTHER INFORMATION: synthetic

<400> SEQUENCE: 10

Thr His Arg Leu Pro Arg Arg Arg Arg Arg Arg
1               5                   10

<210> SEQ ID NO 11
<211> LENGTH: 11
<212> TYPE: PRT
<213> ORGANISM: Artificial Sequence
<220> FEATURE:
<223> OTHER INFORMATION: synthetic

<400> SEQUENCE: 11

Gly Gly Arg Arg Ala Arg Arg Arg Arg Arg Arg
1               5                   10

<210> SEQ ID NO 12
<211> LENGTH: 27
<212> TYPE: DNA
<213> ORGANISM: Artificial Sequence
<220> FEATURE:
<223> OTHER INFORMATION: synthetic

<400> SEQUENCE: 12
gctcccgccc gctcccgctc gctcccg                                      27

<210> SEQ ID NO 13
<211> LENGTH: 35
<212> TYPE: DNA
<213> ORGANISM: Artificial Sequence
<220> FEATURE:
<223> OTHER INFORMATION: synthetic

<400> SEQUENCE: 13
aattcgggag cgagcgggag cgggcgggag ctgct                             35

<210> SEQ ID NO 14
<211> LENGTH: 25
<212> TYPE: DNA
<213> ORGANISM: Artificial Sequence
<220> FEATURE:
<223> OTHER INFORMATION: synthetic

<400> SEQUENCE: 14
tgacctgcag gactcccgcc cgctc                                        25

<210> SEQ ID NO 15
<211> LENGTH: 27
<212> TYPE: DNA
<213> ORGANISM: Artificial Sequence
<220> FEATURE:
<223> OTHER INFORMATION: synthetic

<400> SEQUENCE: 15
tgacgaattc ctagctgcag ggcatgc                                      27

<210> SEQ ID NO 16
<211> LENGTH: 31
<212> TYPE: DNA
<213> ORGANISM: Artificial Sequence
<220> FEATURE:
<223> OTHER INFORMATION: synthetic

<400> SEQUENCE: 16
ctagcctccc gcccgctccc gctcgctccc a                              31

<210> SEQ ID NO 17
<211> LENGTH: 31
<212> TYPE: DNA
<213> ORGANISM: Artificial Sequence
<220> FEATURE:
<223> OTHER INFORMATION: synthetic

<400> SEQUENCE: 17
gatctgggag cgagcgggag cgggcgggag g                              31

<210> SEQ ID NO 18
<211> LENGTH: 31
<212> TYPE: DNA
<213> ORGANISM: Artificial Sequence
<220> FEATURE:
<223> OTHER INFORMATION: synthetic

<400> SEQUENCE: 18
ctagcgcgtc gctcgcttcg cacgtgcgcc a                              31

<210> SEQ ID NO 19
<211> LENGTH: 31
<212> TYPE: DNA
<213> ORGANISM: Artificial Sequence
<220> FEATURE:
<223> OTHER INFORMATION: synthetic

<400> SEQUENCE: 19
gatctggcgc acgtgcgaag cgagcgacgc g                              31

<210> SEQ ID NO 20
<211> LENGTH: 25
<212> TYPE: DNA
<213> ORGANISM: Artificial Sequence
<220> FEATURE:
<223> OTHER INFORMATION: synthetic

<400> SEQUENCE: 20
gcgtcgctcg cttcgcacgt gcgcc                                     25

<210> SEQ ID NO 21
<211> LENGTH: 19
<212> TYPE: DNA
<213> ORGANISM: Artificial Sequence
<220> FEATURE:
<223> OTHER INFORMATION: synthetic

<400> SEQUENCE: 21
gggagcgagc gggcgggag                                            19

<210> SEQ ID NO 22
<211> LENGTH: 57
<212> TYPE: DNA
<213> ORGANISM: Artificial Sequence
<220> FEATURE:

<223> OTHER INFORMATION: synthetic

<400> SEQUENCE: 22
tagcaggtac aagcttctcc cgcccgctcc cgctcgctcc ccatggtgta actagct    57

<210> SEQ ID NO 23
<211> LENGTH: 57
<212> TYPE: DNA
<213> ORGANISM: Artificial Sequence
<220> FEATURE:
<223> OTHER INFORMATION: synthetic

<400> SEQUENCE: 23
agctagttac accatgggga gcgagcggga gcgggcggga gaagcttgta cctgcta    57

<210> SEQ ID NO 24
<211> LENGTH: 57
<212> TYPE: DNA
<213> ORGANISM: Artificial Sequence
<220> FEATURE:
<223> OTHER INFORMATION: synthetic

<400> SEQUENCE: 24
tagcaggtac aagcttcttc cgcccgctcc cgctcgcttc ccatggtgta actagct    57

<210> SEQ ID NO 25
<211> LENGTH: 57
<212> TYPE: DNA
<213> ORGANISM: Artificial Sequence
<220> FEATURE:
<223> OTHER INFORMATION: synthetic

<400> SEQUENCE: 25
agctagttac accatgggga gcgagcggga gcgggcggga gaagcttgta cctgcta    57

<210> SEQ ID NO 26
<211> LENGTH: 24
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (23)..(23)
<223> OTHER INFORMATION: 6-carboxy-fluorescein

<400> SEQUENCE: 26
gacgccggag actgggagag cgnc    24

<210> SEQ ID NO 27
<211> LENGTH: 20
<212> TYPE: DNA
<213> ORGANISM: Artificial Sequence
<220> FEATURE:
<223> OTHER INFORMATION: synthetic

<400> SEQUENCE: 27
ggatatgctg cccaactcca    20

<210> SEQ ID NO 28
<211> LENGTH: 26
<212> TYPE: DNA
<213> ORGANISM: Artificial Sequence
<220> FEATURE:
<223> OTHER INFORMATION: synthetic
<220> FEATURE:
<221> NAME/KEY: misc_feature

```
<222> LOCATION: (24)..(24)
<223> OTHER INFORMATION: 6-carboxy-fluorescein

<400> SEQUENCE: 28
gaacctatga ggaggtggcg aggntc                                          26

<210> SEQ ID NO 29
<211> LENGTH: 20
<212> TYPE: DNA
<213> ORGANISM: Artificial Sequence
<220> FEATURE:
<223> OTHER INFORMATION: synthetic

<400> SEQUENCE: 29
tagggccagg ctaagcagga                                                 20

<210> SEQ ID NO 30
<211> LENGTH: 27
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (25)..(25)
<223> OTHER INFORMATION: 6-carboxy-4',5'-dichloro-2',7'-dimethoxy-
      fluorescein

<400> SEQUENCE: 30
caacaggagg agtgggtgtc gctgntg                                         27

<210> SEQ ID NO 31
<211> LENGTH: 20
<212> TYPE: DNA
<213> ORGANISM: Artificial Sequence
<220> FEATURE:
<223> OTHER INFORMATION: synthetic

<400> SEQUENCE: 31
ggcatcctgg gctacactga                                                 20

<210> SEQ ID NO 32
<211> LENGTH: 16
<212> TYPE: PRT
<213> ORGANISM: Homo sapiens

<400> SEQUENCE: 32

Ile Gly Cys Ile Ile Gly Arg Gln Gly Ala Asn Ile Asn Glu Ile Arg
1               5                   10                  15

<210> SEQ ID NO 33
<211> LENGTH: 34
<212> TYPE: DNA
<213> ORGANISM: Artificial Sequence
<220> FEATURE:
<223> OTHER INFORMATION: synthetic

<400> SEQUENCE: 33
catctcggag gggaattctc cggagagaat catc                                 34

<210> SEQ ID NO 34
<211> LENGTH: 34
<212> TYPE: DNA
<213> ORGANISM: Artificial Sequence
<220> FEATURE:
<223> OTHER INFORMATION: synthetic
```

<400> SEQUENCE: 34
gtagagcctc cccttaagag gcctctctta gtag    34

<210> SEQ ID NO 35
<211> LENGTH: 31
<212> TYPE: DNA
<213> ORGANISM: Artificial Sequence
<220> FEATURE:
<223> OTHER INFORMATION: synthetic

<400> SEQUENCE: 35
gctccccagt catctccgcg ggcggccaag a    31

<210> SEQ ID NO 36
<211> LENGTH: 31
<212> TYPE: DNA
<213> ORGANISM: Artificial Sequence
<220> FEATURE:
<223> OTHER INFORMATION: synthetic

<400> SEQUENCE: 36
cgaggggtca gtagaggcgc ccgccggttc t    31

<210> SEQ ID NO 37
<211> LENGTH: 36
<212> TYPE: DNA
<213> ORGANISM: Artificial Sequence
<220> FEATURE:
<223> OTHER INFORMATION: synthetic

<400> SEQUENCE: 37
gattgggaaa ggcgggtcta agatcaaaga gatccg    36

<210> SEQ ID NO 38
<211> LENGTH: 36
<212> TYPE: DNA
<213> ORGANISM: Artificial Sequence
<220> FEATURE:
<223> OTHER INFORMATION: synthetic

<400> SEQUENCE: 38
ctaacccttt ccgcccagat tctagttct ctaggc    36

<210> SEQ ID NO 39
<211> LENGTH: 31
<212> TYPE: DNA
<213> ORGANISM: Artificial Sequence
<220> FEATURE:
<223> OTHER INFORMATION: synthetic

<400> SEQUENCE: 39
agtctgtcac cgagtctgtc aagcagattt g    31

<210> SEQ ID NO 40
<211> LENGTH: 31
<212> TYPE: DNA
<213> ORGANISM: Artificial Sequence
<220> FEATURE:
<223> OTHER INFORMATION: synthetic

<400> SEQUENCE: 40
tcagacagtg gctcagacag ttcgtctaaa c    31

<210> SEQ ID NO 41
<211> LENGTH: 31

<212> TYPE: DNA
<213> ORGANISM: Artificial Sequence
<220> FEATURE:
<223> OTHER INFORMATION: synthetic

<400> SEQUENCE: 41
gtgtcaagca gatttccctg gtcatgctgg a                                31

<210> SEQ ID NO 42
<211> LENGTH: 31
<212> TYPE: DNA
<213> ORGANISM: Artificial Sequence
<220> FEATURE:
<223> OTHER INFORMATION: synthetic

<400> SEQUENCE: 42
cacagttcgt ctaaagggac cagtacgacc t                                31

<210> SEQ ID NO 43
<211> LENGTH: 31
<212> TYPE: DNA
<213> ORGANISM: Artificial Sequence
<220> FEATURE:
<223> OTHER INFORMATION: synthetic

<400> SEQUENCE: 43
gctccccagt catctccgcg ggcggccaag a                                31

<210> SEQ ID NO 44
<211> LENGTH: 31
<212> TYPE: DNA
<213> ORGANISM: Artificial Sequence
<220> FEATURE:
<223> OTHER INFORMATION: synthetic

<400> SEQUENCE: 44 cgagggtca gtagaggcgc ccgccggttc t                                 31

<210> SEQ ID NO 45
<211> LENGTH: 31
<212> TYPE: DNA
<213> ORGANISM: Artificial Sequence
<220> FEATURE:
<223> OTHER INFORMATION: synthetic

<400> SEQUENCE: 45
gcggccaaga tcggtccagc gacgctgtgg g                                31

<210> SEQ ID NO 46
<211> LENGTH: 31
<212> TYPE: DNA
<213> ORGANISM: Artificial Sequence
<220> FEATURE:
<223> OTHER INFORMATION: synthetic

<400> SEQUENCE: 46
cgccggttct agccaggtcg ctgcgacacc c                                31

<210> SEQ ID NO 47
<211> LENGTH: 38
<212> TYPE: DNA
<213> ORGANISM: Artificial Sequence
<220> FEATURE:
<223> OTHER INFORMATION: synthetic

<400> SEQUENCE: 47

```
ccaaataact taattggctc cataatcggg cgccaagg                    38
```

<210> SEQ ID NO 48
<211> LENGTH: 38
<212> TYPE: DNA
<213> ORGANISM: Artificial Sequence
<220> FEATURE:
<223> OTHER INFORMATION: synthetic

<400> SEQUENCE: 48

```
ggtttattga attaaccgag gtattagccc gcggttcc                    38
```

<210> SEQ ID NO 49
<211> LENGTH: 31
<212> TYPE: DNA
<213> ORGANISM: Artificial Sequence
<220> FEATURE:
<223> OTHER INFORMATION: synthetic

<400> SEQUENCE: 49

```
agaagggcat ggggtccagc tagaacagtg t                           31
```

<210> SEQ ID NO 50
<211> LENGTH: 31
<212> TYPE: DNA
<213> ORGANISM: Artificial Sequence
<220> FEATURE:
<223> OTHER INFORMATION: synthetic

<400> SEQUENCE: 50

```
tcttcccgta ccccaggtcg atcttgtcac a                           31
```

<210> SEQ ID NO 51
<211> LENGTH: 31
<212> TYPE: DNA
<213> ORGANISM: Artificial Sequence
<220> FEATURE:
<223> OTHER INFORMATION: synthetic

<400> SEQUENCE: 51

```
tcaacatctc ggaggcgaat tgtccggaga g                           31
```

<210> SEQ ID NO 52
<211> LENGTH: 30
<212> TYPE: DNA
<213> ORGANISM: Artificial Sequence
<220> FEATURE:
<223> OTHER INFORMATION: synthetic

<400> SEQUENCE: 52

```
agttgtagag cctccgctta acaggcctct                             30
```

<210> SEQ ID NO 53
<211> LENGTH: 31
<212> TYPE: DNA
<213> ORGANISM: Artificial Sequence
<220> FEATURE:
<223> OTHER INFORMATION: synthetic

<400> SEQUENCE: 53

```
caaataactt aattgcctgc ataatcgggc g                           31
```

<210> SEQ ID NO 54
<211> LENGTH: 31
<212> TYPE: DNA
<213> ORGANISM: Artificial Sequence
<220> FEATURE:
<223> OTHER INFORMATION: synthetic

<400> SEQUENCE: 54
gtttattgaa ttaacggacg tattagcccg c                               31

<210> SEQ ID NO 55
<211> LENGTH: 159
<212> TYPE: DNA
<213> ORGANISM: Homo sapiens

<400> SEQUENCE: 55
gactcccgcc cgctcccgct cgctcccgcg gtcctcgctc gcctcgcgcc ggtagttttg    60
ggcctacacc tcccctcccc ccgccaccgc caaagacttg accacgtaac gagcccaact   120
cccccgaacg ccgcccgccg ctcgccatgg atgccggtg                         159

<210> SEQ ID NO 56
<211> LENGTH: 44
<212> TYPE: DNA
<213> ORGANISM: Artificial Sequence
<220> FEATURE:
<223> OTHER INFORMATION: synthetic

<400> SEQUENCE: 56
cacggaattc tcccgcccgc tcccgctcgc tcccaagctt gggt                   44

<210> SEQ ID NO 57
<211> LENGTH: 44
<212> TYPE: DNA
<213> ORGANISM: Artificial Sequence
<220> FEATURE:
<223> OTHER INFORMATION: synthetic

<400> SEQUENCE: 57
acccaagctt gggagcgagc gggagcgggc gggagaattc cgtg                   44

<210> SEQ ID NO 58
<211> LENGTH: 44
<212> TYPE: DNA
<213> ORGANISM: Artificial Sequence
<220> FEATURE:
<223> OTHER INFORMATION: synthetic

<400> SEQUENCE: 58
cacggaattc ttccgcccgc tcccgctcgc tcccaagctt gggt                   44

<210> SEQ ID NO 59
<211> LENGTH: 44
<212> TYPE: DNA
<213> ORGANISM: Artificial Sequence
<220> FEATURE:
<223> OTHER INFORMATION: synthetic

<400> SEQUENCE: 59
acccaagctt gggagcgagc gggagcgggc ggaagaattc cgtg                   44

<210> SEQ ID NO 60
<211> LENGTH: 44
<212> TYPE: DNA
<213> ORGANISM: Artificial Sequence
<220> FEATURE:
<223> OTHER INFORMATION: synthetic

<400> SEQUENCE: 60
cacggaattc tcccgcccgc ttccgctcgc tcccaagctt gggt            44

<210> SEQ ID NO 61
<211> LENGTH: 44
<212> TYPE: DNA
<213> ORGANISM: Artificial Sequence
<220> FEATURE:
<223> OTHER INFORMATION: synthetic

<400> SEQUENCE: 61
acccaagctt gggagcgagc ggaagcgggc gggagaattc cgtg            44

<210> SEQ ID NO 62
<211> LENGTH: 44
<212> TYPE: DNA
<213> ORGANISM: Artificial Sequence
<220> FEATURE:
<223> OTHER INFORMATION: synthetic

<400> SEQUENCE: 62
cacggaattc tcccgcccgc tcccgctcgc ttccaagctt gggt            44

<210> SEQ ID NO 63
<211> LENGTH: 44
<212> TYPE: DNA
<213> ORGANISM: Artificial Sequence
<220> FEATURE:
<223> OTHER INFORMATION: synthetic

<400> SEQUENCE: 63
acccaagctt ggaagcgagc gggagcgggc gggagaattc cgtg            44

<210> SEQ ID NO 64
<211> LENGTH: 44
<212> TYPE: DNA
<213> ORGANISM: Artificial Sequence
<220> FEATURE:
<223> OTHER INFORMATION: synthetic

<400> SEQUENCE: 64
cacggaattc ttccgcccgc ttccgctcgc tcccaagctt gggt            44

<210> SEQ ID NO 65
<211> LENGTH: 44
<212> TYPE: DNA
<213> ORGANISM: Artificial Sequence
<220> FEATURE:
<223> OTHER INFORMATION: synthetic

<400> SEQUENCE: 65
acccaagctt gggagcgagc ggaagcgggc ggaagaattc cgtg            44

<210> SEQ ID NO 66
<211> LENGTH: 44
<212> TYPE: DNA
<213> ORGANISM: Artificial Sequence
<220> FEATURE:
<223> OTHER INFORMATION: synthetic

<400> SEQUENCE: 66
cacggaattc tcccgcccgc ttccgctcgc ttccaagctt gggt            44

<210> SEQ ID NO 67
<211> LENGTH: 44
<212> TYPE: DNA
<213> ORGANISM: Artificial Sequence

```
<220> FEATURE:
<223> OTHER INFORMATION: synthetic

<400> SEQUENCE: 67
acccaagctt ggaagcgagc ggaagcgggc gggagaattc cgtg            44

<210> SEQ ID NO 68
<211> LENGTH: 44
<212> TYPE: DNA
<213> ORGANISM: Artificial Sequence
<220> FEATURE:
<223> OTHER INFORMATION: synthetic

<400> SEQUENCE: 68
cacggaattc ttccgcccgc tcccgctcgc ttccaagctt gggt            44

<210> SEQ ID NO 69
<211> LENGTH: 44
<212> TYPE: DNA
<213> ORGANISM: Artificial Sequence
<220> FEATURE:
<223> OTHER INFORMATION: synthetic

<400> SEQUENCE: 69
acccaagctt ggaagcgagc gggagcgggc ggaagaattc cgtg            44

<210> SEQ ID NO 70
<211> LENGTH: 44
<212> TYPE: DNA
<213> ORGANISM: Artificial Sequence
<220> FEATURE:
<223> OTHER INFORMATION: synthetic

<400> SEQUENCE: 70
cacggaattc ttccgcccgc ttccgctcgc ttccaagctt gggt            44

<210> SEQ ID NO 71
<211> LENGTH: 44
<212> TYPE: DNA
<213> ORGANISM: Artificial Sequence
<220> FEATURE:
<223> OTHER INFORMATION: syntehtic

<400> SEQUENCE: 71
acccaagctt ggaagcgagc ggaagcgggc ggaagaattc cgtg            44

<210> SEQ ID NO 72
<211> LENGTH: 19
<212> TYPE: PRT
<213> ORGANISM: Homo sapiens

<400> SEQUENCE: 72

Ser Leu Ala Gln Tyr Leu Ile Asn Ala Arg Leu Ser Ser Glu Lys Gly
1               5                   10                  15

Met Gly Cys

<210> SEQ ID NO 73
<211> LENGTH: 19
<212> TYPE: PRT
<213> ORGANISM: Artificial Sequence
<220> FEATURE:
<223> OTHER INFORMATION: analytical consensus sequence
<220> FEATURE:
<221> NAME/KEY: misc_feature
<222> LOCATION: (9)..(9)
<223> OTHER INFORMATION: Xaa can be any naturally occurring amino acid
```

```
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(19)
<223> OTHER INFORMATION: Xaa can be any naturally occurring amino acid

<400> SEQUENCE: 73

Ser Leu Ala Gln Tyr Leu Ile Asn Xaa Arg Leu Ser Ser Glu Xaa Gly
1               5                   10                  15

Xaa Xaa Xaa

<210> SEQ ID NO 74
<211> LENGTH: 19
<212> TYPE: PRT
<213> ORGANISM: Homo sapiens

<400> SEQUENCE: 74

Ser Leu Ala Gln Tyr Leu Ile Asn Val Arg Leu Ser Ser Glu Thr Gly
1               5                   10                  15

Gly Met Gly

<210> SEQ ID NO 75
<211> LENGTH: 356
<212> TYPE: PRT
<213> ORGANISM: Artificial Sequence
<220> FEATURE:
<223> OTHER INFORMATION: synthetic

<400> SEQUENCE: 75

Met Asp Ala Gly Val Thr Glu Ser Gly Leu Asn Val Thr Leu Thr Ile
1               5                   10                  15

Arg Leu Leu Met His Gly Lys Glu Val Gly Ser Ile Ile Gly Lys Lys
                20                  25                  30

Gly Glu Ser Val Lys Arg Ile Arg Glu Glu Ser Gly Ala Arg Ile Asn
            35                  40                  45

Ile Ser Glu Gly Asn Cys Pro Glu Arg Ile Ile Thr Leu Thr Gly Pro
        50                  55                  60

Thr Asn Ala Ile Phe Lys Ala Phe Ala Met Ile Ile Asp Lys Leu Glu
65                  70                  75                  80

Glu Asp Ile Asn Ser Ser Met Thr Asn Ser Thr Ala Ala Ser Arg Pro
                85                  90                  95

Pro Val Thr Leu Arg Leu Val Val Pro Ala Thr Gln Cys Gly Ser Leu
            100                 105                 110

Ile Gly Lys Gly Gly Cys Lys Ile Lys Glu Ile Arg Glu Ser Thr Gly
        115                 120                 125

Ala Gln Val Gln Val Ala Gly Asp Met Leu Pro Asn Ser Thr Glu Arg
    130                 135                 140

Ala Ile Thr Ile Ala Gly Val Pro Gln Ser Val Thr Glu Cys Val Lys
145                 150                 155                 160

Gln Ile Cys Leu Val Met Leu Glu Thr Leu Ser Gln Ser Pro Gln Gly
                165                 170                 175

Arg Val Met Thr Ile Pro Tyr Gln Pro Met Pro Ala Ser Ser Pro Val
            180                 185                 190

Ile Cys Ala Gly Gly Gln Asp Arg Cys Ser Asp Ala Val Gly Tyr Pro
        195                 200                 205

His Ala Thr His Asp Leu Glu Gly Pro Pro Leu Asp Ala Tyr Ser Ile
```

|  | 210 |  |  |  | 215 |  |  |  |  | 220 |  |  |  |  |
|---|---|---|---|---|---|---|---|---|---|---|---|---|---|---|
| Gln | Gly | Gln | His | Thr | Ile | Ser | Pro | Leu | Asp | Leu | Ala | Lys | Leu | Asn | Gln |
| 225 |  |  |  |  | 230 |  |  |  |  | 235 |  |  |  |  | 240 |
| Val | Ala | Arg | Gln | Gln | Ser | His | Phe | Ala | Met | Met | His | Gly | Gly | Thr | Gly |
|  |  |  |  | 245 |  |  |  |  | 250 |  |  |  |  | 255 |  |
| Phe | Ala | Gly | Ile | Asp | Ser | Ser | Ser | Pro | Glu | Val | Lys | Gly | Tyr | Trp | Ala |
|  |  |  | 260 |  |  |  |  | 265 |  |  |  |  | 270 |  |  |
| Ser | Leu | Asp | Ala | Ser | Thr | Gln | Thr | Thr | His | Glu | Leu | Thr | Ile | Pro | Asn |
|  |  | 275 |  |  |  |  | 280 |  |  |  |  | 285 |  |  |  |
| Asn | Leu | Ile | Gly | Cys | Ile | Ile | Gly | Arg | Gln | Gly | Ala | Asn | Ile | Asn | Glu |
|  |  | 290 |  |  |  | 295 |  |  |  |  | 300 |  |  |  |  |
| Ile | Arg | Gln | Met | Ser | Gly | Ala | Gln | Ile | Lys | Ile | Ala | Asn | Pro | Val | Glu |
| 305 |  |  |  |  | 310 |  |  |  |  | 315 |  |  |  |  | 320 |
| Gly | Ser | Ser | Gly | Arg | Gln | Val | Thr | Ile | Thr | Gly | Ser | Ala | Ala | Ser | Ile |
|  |  |  |  | 325 |  |  |  |  | 330 |  |  |  |  | 335 |  |
| Ser | Leu | Ala | Gln | Tyr | Leu | Ile | Asn | Ala | Arg | Leu | Ser | Ser | Glu | Lys | Gly |
|  |  |  | 340 |  |  |  |  | 345 |  |  |  |  | 350 |  |  |
| Met | Gly | Cys | Ser |
|  |  | 355 |  |